United States Patent
Shen et al.

(10) Patent No.: US 8,513,233 B2
(45) Date of Patent: Aug. 20, 2013

(54) PYRIMIDINYL-PROPIONIC ACID DERIVATIVES AND THEIR USE AS PPAR AGONISTS

(75) Inventors: Jianhua Shen, Shanghai (CN); Changlin Mei, Shanghai (CN); Hualiang Jiang, Shanghai (CN); Bin Dai, Shanghai (CN); Yangliang Ye, Shanghai (CN); Xishan Xiong, Shanghai (CN); Jing Tang, Shanghai (CN); Lili Fu, Shanghai (CN)

(73) Assignee: Shanghai Institute of Materia Medica, CAS, Shanghai (CN)

( * ) Notice: Subject to any disclaimer, the term of this patent is extended or adjusted under 35 U.S.C. 154(b) by 356 days.

(21) Appl. No.: 12/682,530

(22) PCT Filed: Oct. 11, 2007

(86) PCT No.: PCT/CN2007/070874
§ 371 (c)(1),
(2), (4) Date: May 26, 2010

(87) PCT Pub. No.: WO2009/046606
PCT Pub. Date: Apr. 16, 2009

(65) Prior Publication Data
US 2010/0240636 A1  Sep. 23, 2010

(51) Int. Cl.
*A61K 31/55* (2006.01)
*A61K 31/506* (2006.01)
*A61K 31/5377* (2006.01)
*C07D 403/04* (2006.01)
*C07D 403/14* (2006.01)
*C07D 413/14* (2006.01)

(52) U.S. Cl.
USPC ............ 514/212.07; 514/252.14; 514/252.2; 514/252.18; 514/235.8; 514/252.19; 514/252.11; 544/295; 544/296; 544/121

(58) Field of Classification Search
USPC ............ 514/212.07, 252.14, 252.2, 252.18, 514/235.8, 252.19, 252.11; 544/295, 296, 544/121
See application file for complete search history.

(56) References Cited

FOREIGN PATENT DOCUMENTS

| CN | 1271349 A | 10/2000 |
|---|---|---|
| CN | 1739521 A | 3/2006 |
| CN | 101002940 A | 7/2007 |
| CN | 101054372 A | 10/2007 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Vippagunta et al., Crystalline solids, 2001, Advanced Drug Delivery Reviews, 48, pp. 3 and 18.*
The State Intellectual Property Office, The Peoples Republic of China, International Search Report for International Application No. PCT/CN2007/070874, mailed Jul. 24, 2008.
The State Intellectual Property Office, The Peoples Republic of China, Written Opinion of the International Searching Authority for International Application No. PCT/CN/2007/070874, mailed Jul. 24, 2008.
Satoru Muto et al., "Pioglitazone improves the phenotype and molecular defects of a targeted Pkd1 mutant," Human Molecular Genetics, Oxford University Press 2002, vol. 11, No. 15, pp. 1731-1742 (received Mar. 28, 2002; Accepted May 24, 2002).

* cited by examiner

*Primary Examiner* — Kristin Bianchi
(74) *Attorney, Agent, or Firm* — Baker Botts L.L.P.

(57) ABSTRACT

The present invention disclosed compounds of Structural Formula (I), and enantiomer, racemic body, pharmaceutically acceptable salts, solvates or hydrates thereof, wherein variable groups are as defined within, as well as methods for preparing such compounds. The compounds are useful as PPARγ agonist, through activating PPAR-RXR heterodimers that interacts with specific DNA response elements within promoter regions of target gene, particularly in the treatment and prevention of polycystic kidney and cancer.

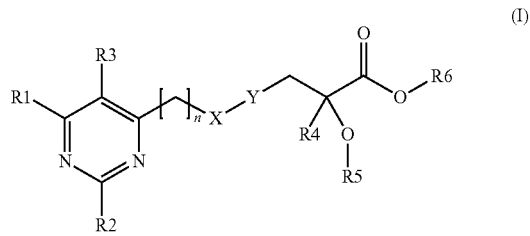

25 Claims, 1 Drawing Sheet

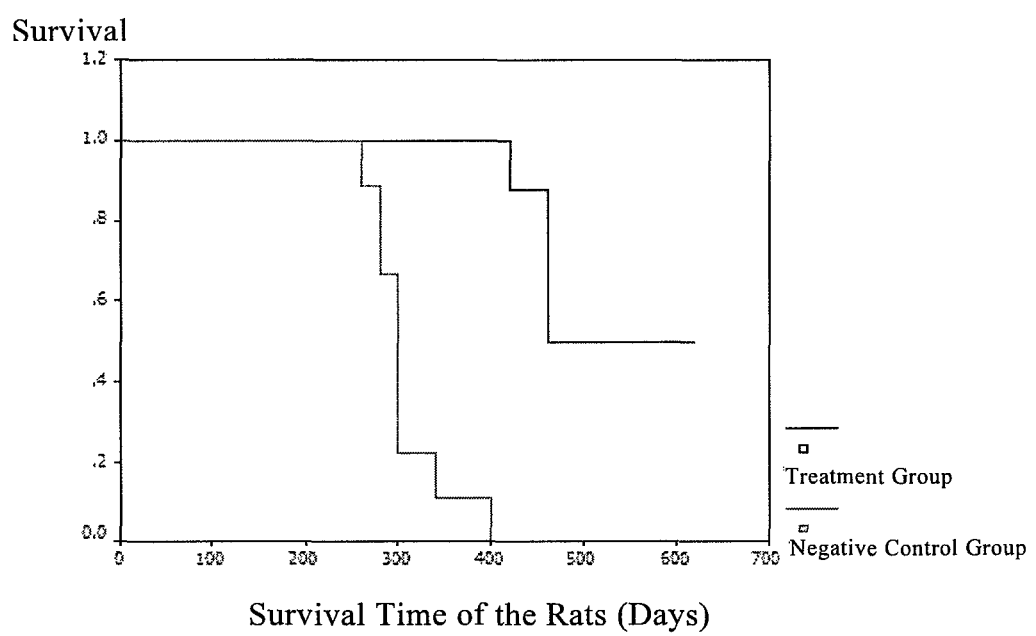
Survival Time of the Rats (Days)

PYRIMIDINYL-PROPIONIC ACID DERIVATIVES AND THEIR USE AS PPAR AGONISTS

CROSS-REFERENCE TO RELATED APPLICATION

This application is a national stage application of International Patent Application No. PCT/CN2007/070874, filed Oct. 11, 2007, the disclosure of which is incorporated herein by reference in its entirety.

BACKGROUND OF THE INVENTION

Peroxisome proliferators-activated receptors (PPARs) are members of the nuclear hormone receptor superfamily. There are three PPAR subtypes, which are the products of distinct genes and are commonly designated PPARα, PPARγ and PPARδ. Among them, PPARγ is the most extensively studied. Through heterodimerization with retinoid X receptors (RXRs), PPAR-RXR heterodimers bind to DNA-specific sequences called peroxisome proliferator response elements (PPREs), regulating the transcription of genes whose products are involved in lipid homeostasis, cell growth, and differentiation. Recent studies have shown that PPAR-γ is not only correlated to diseases such as obesity, insulin resistance, diabetes, hypertension, artherosclerosis, inflammation, but also potential target for treatment of ADPKD and cancer.

Hereditary forms of polycystic kidney disease (PKD) in humans are transmitted in either an autosomal recessive (ARPKD) or an autosomal dominant pattern (ADPKD), ADPKD, one of the most common, potentially lethal single-gene disorders, is the leading form of inherited kidney disorders. It is characterized by the accumulation of fluid-filled cysts in the cortex and medulla of bilateral kidneys and other organs like liver, seminal vesicles, pancreas and arachnoid membrane, causing extrarenal abnormalities such as intracranial aneurysms and dolichoectasias, dilatation of the aortic root, dissection of the thoracic aorta, mitral valve prolapse and abdominal wall hernias. It affects about 1:500 to 1:1000 people in all ethnic groups worldwide. In China, about 1,500,000 people have ADPKD, approximately 50% of people with it develop renal failure at the age of 60.

Since the genes responsible for ADPKD have been cloned and gene diagnosis, imaging detecting technologies have been developed quickly, prenatal/presymptomatic diagnosis has been possible clinically at present, more and more ADPKD sufferers could be diagnosed earlier without any clinical symptom or imageological changes. Currently, no effective treatment can prevent the cysts from forming or enlarging. Finding novel therapeutic interventions to delay the progression of PKD is an urgent task, researchers across the world are seeking novel drug targets all the time for treatment and prevention of ADPKD.

Muto et al have found that a PPAR-γ agonist pioglitazone, could prolong the lifespan of Pkd1−/− mices with ADPKD which usually die at the foetal period.

In vitro we firstly prove that PPAR-γ agonists 15d-PGJ2, rosiglitazone or pioglitazone could inhibit the proliferation and induce apoptosis of ADPKD cyst-lining epithelia in a dose-dependent and time-dependent manner, while the effect on human renal epithelial cells (HKC) is relatively weak. After administration of rosiglitazone on the Han:SPRD rats, the well documented animal model of ADPKD, treatment group had lesser proteinuria, kidney weight/body weight, blood urea nitrogen (BUN), cyst index, fibrosis score and inflammatory cells infiltration compared with control group by serological and histomorphometric analysis. The therapeutic mechanism seems not depend on it's metabolism regulation effect on serum glucose and lipid, but through inhibition of abnormal proliferation, apoptosis, interstitial inflammation and fibrosis. Long-term treatment shows rosiglitazone can prolong the survival of Han:SPRD rats (patent application number 200610023398.6). Considering the safety and efficacy of thiazolidinediones in treatment of animal model of ADPKD and type 2 diabetes patients clinically, PPAR-γ agonists may be effective in the treatment of ADPKD.

Thiazolidinediones are now widely used in the treatment of type 2 diabetes as PPAR-γ agonists, these include rosiglitazone, pioglitazone, troglitazone, et. Troglitazone was withdrawn in Europe and USA not long after it went on sale because of severe liver toxicity. Although rosiglitazone and pioglitazone show potent activity with less hepatotoxicity than troglitazone, they also have long-term side effects, such as hepatotoxicity, water-sodium retention, weight gain and possible exacerbation of congestive heart failure. In vivo, we also found that rosiglitazone-treated Han:SPRD rats demonstrated heart and liver weight gain with increased volume when they died, indicating that TZDs, administered chronically at high dose, could aggravate water-sodium retention and cardiac load, resulting in chronic congestive heart failure and hepatic congestion. Because multiple ADPKD patients merge with hyperpiesia and myocardial hypertrophy in midanaphase, the side effects of this kind of drugs, like aggravating congestive heart failure, challenges the clinical application in dealing with ADPKD. Since ADPKD sufferers generally need long-term administration or even lifelong medication, the drug safety is especially important and urgent in these patients.

Recently, researcher also have found that PPAR-γ is expressed in many cancers including the colon, breast, lung and prostate, and PPAR-γ ligands are generally antiproliferative in these settings. Specifically, PPAR-γ ligands inhibit the proliferation of human breast, prostate, colon and pituitary cancer cells in vitro. Thus PPAR-γ is considered to have potential antineoplastic effects both in solid cancers and in leukemia through inhibition of cell proliferation, induction of apoptosis and terminal differentiation or through inhibition of angiogenesis. Therefore, PPAR-γ ligands may represent a promising, novel therapeutic approach for certain human malignancies. On the other hand, it's evidenced by the fact that many people in the world are currently taking drug as PPAR-γ agonists for long-term control of type 2 diabetes. Thus, in the context of human cancer, it is important to note that PPAR-γ agonists are relatively nontoxic and well tolerated.

In sum, it is urgent to synthesize novel effective PPAR-γ agonists with less side effects in ADPKD and cancer treatment.

SUMMARY OF THE INVENTION

In a first aspect of the present invention, the present invention is directed to compounds represented by Structural Formula I and pharmaceutically acceptable salts, solvates and hydrates thereof:

Structural Formula I

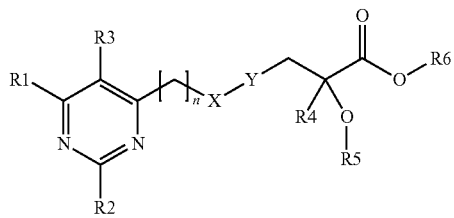

wherein:

X is $CH_2$, $CH(OH)$, $C(O)O$, $NH$, $S$, or $SO_2$;

Y is an unsubstituted or substituted phenyl (optionally substituted by one or more of the following groups: $C_1$-$C_6$ straight-chain or branched-chain alkyl, halogen, $C_1$-$C_6$ haloalkyl, amino, mercapto, cyano, nitro, hydroxyl, trifluoromethyl, and trifluoromethoxy);

n is 0, 2, 3, or 4;

$R_1$ is hydro or $C_1$-$C_6$ alkyl, $C_1$-$C_8$ alkoxyl, mercapto, cyano, nitro, hydroxyl, trifluoromethyl, trifluoromethoxy, phenoxy; unsubstituted or substituted $C_3$-$C_6$ heterocycloalkyl [optionally substituted by one or more of the following groups: $C_1$-$C_8$ alkyl, halogen, $C_3$-$C_6$ cycloalkyl, ($C_3$-$C_6$) cycloalkyl($C_1$-$C_6$)alkyl, $C_1$-$C_6$ haloalkyl, amino, mercapto, cyano, nitro, hydroxyl, trifluoromethyl, trifluoromethoxy, unsubstituted or substituted groups selected from: $C_6$-$C_{12}$ heteroaryl containing one or two oxygen or nitrogen, $C_3$-$C_6$ heterocycloalkyl containing one or two oxygen or nitrogen, ($C_6$-$C_{12}$)heterocycloalkyl($C_1$-$C_6$)alkyl containing one or two oxygen or nitrogen, phenyl, ($C_5$-$C_{12}$)aryl($C_1$-$C_6$)alkyl (including: benzyl, phenethyl, naphthalen-1-ylmethyl), phenoxy, or carbobenzoxy(optionally substituted by one or more of the following groups: halogen, oxo, $C_1$-$C_6$ alkyl, $C_1$-$C_8$ alkoxyl, $C_1$-$C_6$ haloalkyl, amino, mercapto, cyano, nitro, hydroxyl, trifluoromethyl, trifluoromethoxy; unsubstituted or substituted phenyl or phenoxy which is substituted by one or more of the following substituents: halogen, $C_1$-$C_6$ haloalkyl, amino, mercapto, cyano, nitro, hydroxyl, trifluoromethyl, or trifluoromethoxy)].

$R_2$ is H, phenyl, $C_1$-$C_6$ alkyl, $C_1$-$C_8$ alkoxyl, amino, mercapto, cyano, nitro, hydroxyl, trifluoromethyl, trifluoromethoxy, unsubstituted or substituted amino [(optionally substituted by one or more of the following groups: $C_1$-$C_6$ alkyl, $C_3$-$C_7$ carbocyclyl, phenyl, benzyl, aralkyl, sulfanilamino, pyridyl, $C_1$-$C_4$ acyl), unsubstituted or substituted $C_3$-$C_6$ heterocycloalkyl which contains one or two oxygen or nitrogen, (optionally substituted by one or more of the following groups: halogen, $C_1$-$C_6$ haloalkyl, amino, mercapto, cyano, nitro, hydroxyl, trifluoromethyl, trifluoromethoxy, benzyl), unsubstituted or substituted phenoxy (optionally substituted by one or more of the following groups: halogen, $C_1$-$C_6$ haloalkyl, amino, mercapto, cyano, nitro, hydroxyl, trifluoromethyl, trifluoromethoxy);

$R_3$ is H, $C_1$-$C_8$ alkoxyl, halogen, mercapto, cyano, nitro, hydroxyl, trifluoromethyl, trifluoromethoxy, $C_1$-$C_6$ straight-chain or branched-chain alkyl, phenyl, aralkyl, thioureido, unsubstituted or substituted amino (optionally substituted by one or more of the following groups: $C_1$-$C_6$ straight-chain or branched-chain alkyl, $C_3$-$C_6$ heterocycloalkyl, phenyl, aralkyl, sulfanilamino, pyridyl, and $C_1$-$C_4$ acyl);

$R_4$ is H, $C_1$-$C_6$ straight-chain or branched-chain alkyl, $C_1$-$C_8$ alkoxyl, mercapto, hydroxyl, trifluoromethyl, trifluoromethoxy or unsubstituted or substituted phenoxy (optionally substituted by one or more of the following groups: halogen, $C_1$-$C_6$ haloalkyl, amino, mercapto, hydroxyl, trifluoromethyl, and trifluoromethoxy);

$R_5$ is H, $C_1$-$C_6$ straight-chain or branched-chain alkyl, unsubstituted or substituted phenyl [optionally substituted by one or more of the following groups: halogen, $C_1$-$C_6$ haloalkyl, $C_1$-$C_6$ straight-chain or branched-chain alkyl, $C_1$-$C_8$ alkoxyl, amino, mercapto, cyano, hydroxyl, trifluoromethyl, trifluoromethoxy, unsubstituted or substituted phenyl (optionally substituted by one or more of the following groups: halogen, $C_1$-$C_4$ haloalkyl, amino, mercapto, hydroxyl, trifluoromethyl, and trifluoromethoxy)];

$R_6$ is H, $C_1$-$C_6$ straight-chain or branched-chain alkyl.

Preferably, the compounds of the present invention, and with their respective pharmaceutical compositions, have a structure represented by Structural Formula II Structural Formula II

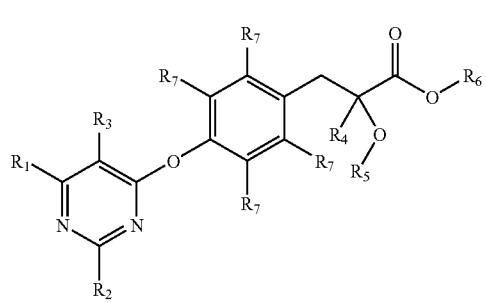

In Structural Formula II, $R_1$, $R_2$, $R_3$, $R_4$, $R_5$ and $R_6$ is defined for Structural Formula I, while $R_7$ are each, independently, H, $C_1$-$C_6$ straight-chain or branched-chain alkyl, halo, $C_1$-$C_6$ haloalkyl, amino, mercapto, cyano, nitro, hydroxyl, trifluoromethyl, or trifluoromethoxy;

More preferably, the compounds of the present invention, and with their respective pharmaceutical compositions, have a structure represented by Structural Formula III Structural Formula III

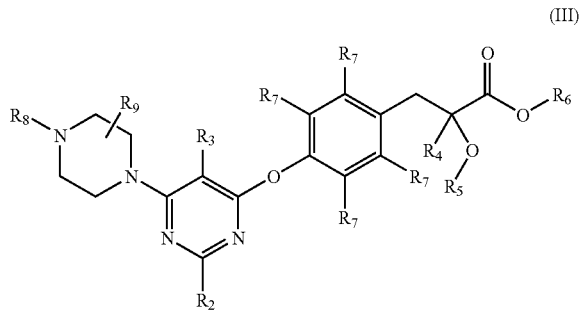

In Structural Formula III, $R_2$, $R_3$, $R_4$, $R_5$, $R_6$ and $R_7$ are as defined for Structural Formula II, while $R_8$ are each, independently, H, $C_1$-$C_6$ straight-chain or branched-chain alkyl, $C_3$-$C_6$ cycloalkyl, $C_1$-$C_6$ haloalkyl; unsubstituted or substituted groups selected from: $C_6$-$C_{12}$ heteroaryl containing one or two oxygen or nitrogen, $C_3$-$C_6$ heterocycloalkyl containing one or two oxygen or nitrogen, ($C_6$-$C_{12}$)heterocycloalkyl($C_1$-$C_6$)alkyl containing one or two oxygen or nitrogen, phenyl, ($C_5$-$C_{12}$)aryl($C_1$-$C_6$)alkyl (including: benzyl, phenethyl, naphthalen-1-ylmethyl), phenoxy, carbobenzoxy, phenyl, benzyl, phenethyl, or carbobenzoxy [optionally substituted by one or more of the following groups: halogen, $C_1$-$C_6$ haloalkyl, $C_1$-$C_6$ alkyl, $C_1$-$C_8$ alkoxyl, amino, mercapto, cyano, nitro, hydroxyl, trifluoromethyl, trifluoromethoxy, unsubstituted or substituted phenyl or phenoxy (optionally substituted by one or more of the following groups: halogen, $C_1$-$C_6$ haloalkyl, amino, mercapto, cyano, hydroxyl, trifluoromethyl, and trifluoromethoxy)];

$R_9$ is H, $C_1$-$C_8$ straight-chain or branched-chain alkyl, halogen, $C_1$-$C_4$ haloalkyl, amino, mercapto, cyano, hydroxyl, trifluoromethyl, or trifluoromethoxy.

More preferably, the compounds of the present invention, and with their respective pharmaceutical compositions, have a structure represented by Structural Formula IV Structural Formula IV

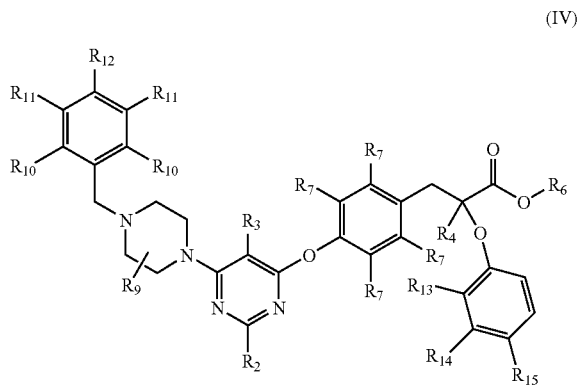

(IV)

In Structural Formula IV, $R_2$, $R_3$, $R_4$, $R_6$, $R_7$ and $R_9$ are as defined for Structural Formula III;

While $R_{10}$, $R_{11}$, $R_{12}$ is H, halogen, $C_1$-$C_6$ haloalkyl, $C_1$-$C_6$ straight-chain or branched-chain alkyl, $C_1$-$C_8$ alkoxyl, amino, mercapto, cyano, nitro, hydroxyl, trifluoromethyl, trifluoromethoxy, unsubstituted or substituted phenyl or phenoxy (optionally substituted by one or more of the following groups: halogen, $C_1$-$C_6$ haloalkyl, amino, mercapto, cyano, hydroxyl, trifluoromethyl, and trifluoromethoxy);

Further, $R_{13}$, $R_{14}$, $R_{15}$ is halogen, $C_1$-$C_6$ haloalkyl, amino, mercapto, cyano, hydroxyl, trifluoromethyl, trifluoromethoxy, unsubstituted or substituted phenyl (optionally substituted by one or more of the following groups: halogen, $C_1$-$C_6$ haloalkyl, amino, mercapto, hydroxyl, trifluoromethyl, and trifluoromethoxy);

Even more preferable, the compounds of the present invention, and with their respective pharmaceutical compositions, have a structure represented by Structural Formula V, Structural Formula V

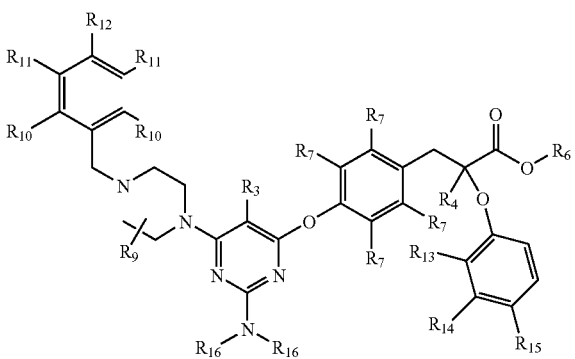

(V)

$R_3$, $R_4$, $R_6$, $R_7$, $R_9$, $R_{10}$, $R_{11}$, $R_{12}$, $R_{13}$, $R_{14}$, and $R_{15}$ are as defined for Structural Formula IV;

While $R_{16}$ optionally and independently substituted one or two times with $C_1$-$C_6$ straight-chain or branched-chain alkyl, $C_3$-$C_7$ cycloalkyl, phenyl, aralkyl, sulfanilamino, pyridyl, acyl, unsubstituted or substituted $C_3$-$C_6$ heterocycloalkyl (optionally substituted by one or more of the following groups: halogen, $C_1$-$C_6$ haloalkyl, amino, mercapto, cyano, hydroxyl, trifluoromethyl, and trifluoromethoxy);

In a second aspect of the present invention, the present invention provides a process for preparing a compound of Formula (I) or a pharmaceutically acceptable salt thereof, which process (wherein variable groups are, unless otherwise specified, as defined in formula (I)) comprises of:

In the presence of cesium carbonate, compound (Ia) is treated with compound (Ib) in a polar solvent at a temperature of about 60° C. to about 100° C., to form compound (I):

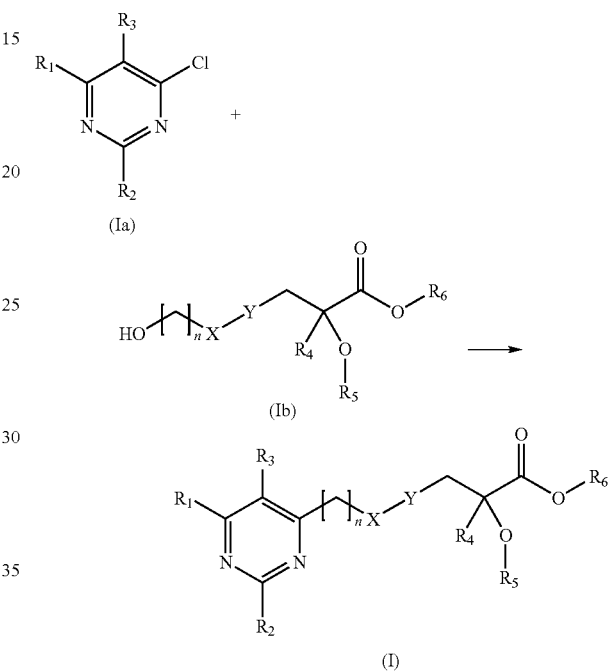

while, $R_1$~$R_6$ are as defined for Structural Formula I;

In one embodiment, the customary organic solvents which do not change under the reaction conditions are selected from: 1,2-dimethoxyethane, THF, DMF, dichloromethane, acetone, EA, methanol, ethanol, water, or mixed solvent such as THF, water, methanol or the mixture thereof.

In another embodiment of the present invention, the reaction temperature is between 60° C. and 100° C., preferably between 70° C. to 90° C.; the reaction time is 15 minutes to 2 days, preferable is 30 minutes to 1 day.

Compounds of Structural Formula (II) have been formed by the procedures herein:

In the presence of cesium carbonate, compound (Ia) is treated with compound (IIa) in a polar solvent at a temperature of about 60° C. to about 100° C., to form compound (II):

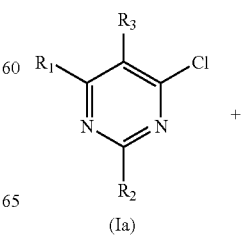

(Ia)

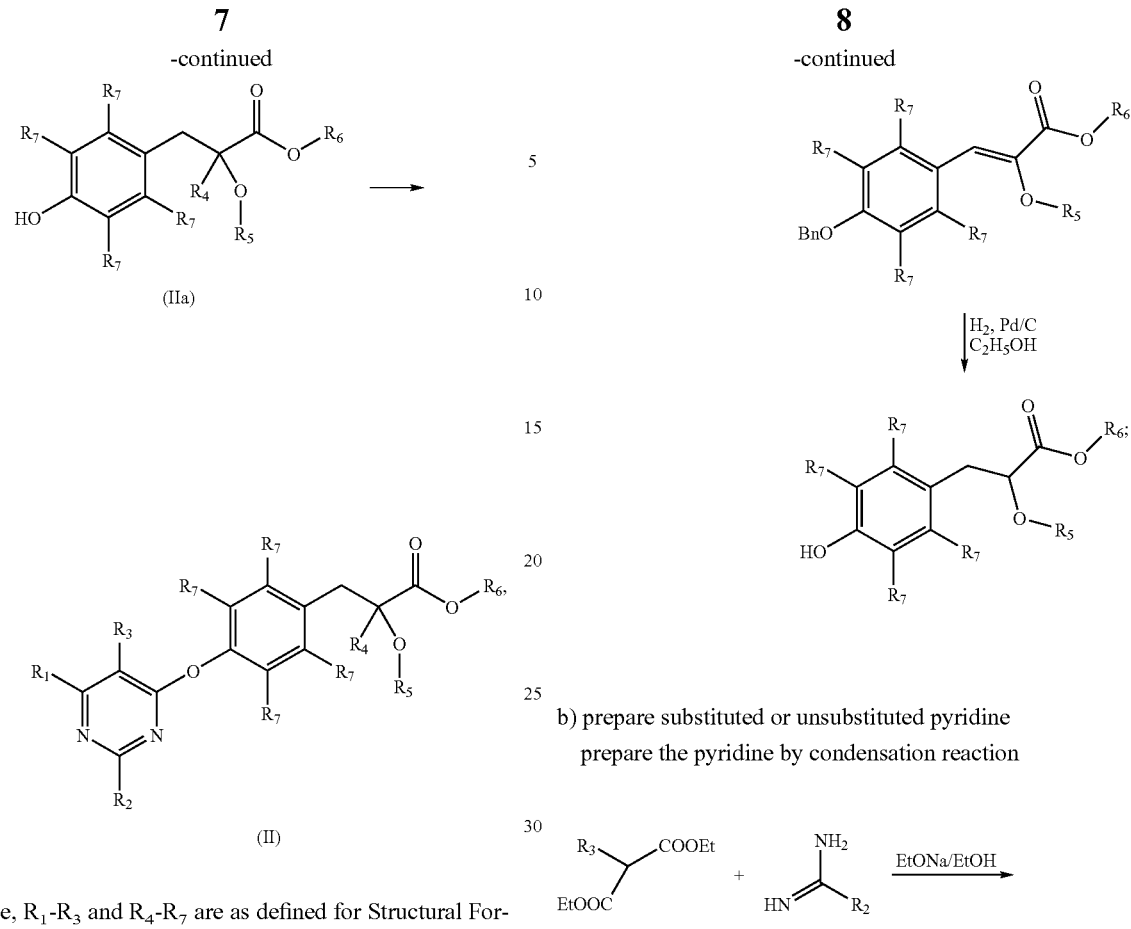

while, $R_1$-$R_3$ and $R_4$-$R_7$ are as defined for Structural Formula II;

While $R_4$ is H, Compounds of Structural Formula (II) have been formed by the procedures herein:

a) synthesize α-substituted phenylpropionate ester:

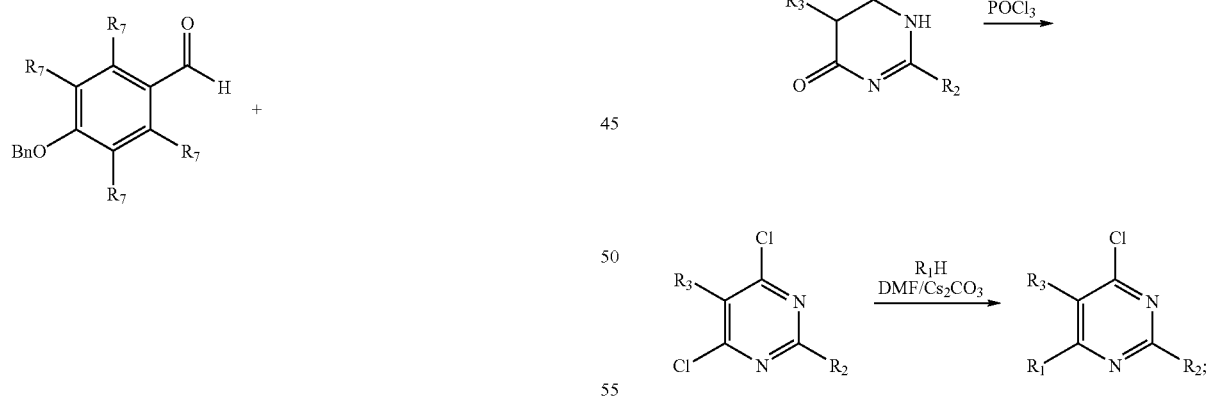

b) prepare substituted or unsubstituted pyridine
prepare the pyridine by condensation reaction While $R_2$ is substituted amino, $R_3$ is H, $R_{16}$ is as defined in Structural Formula IV;

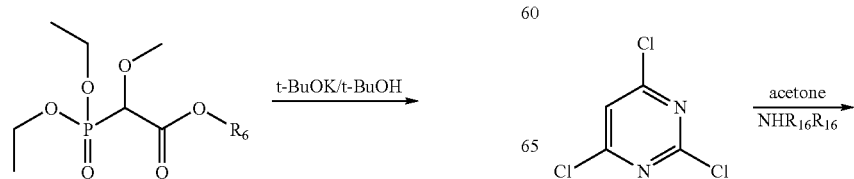

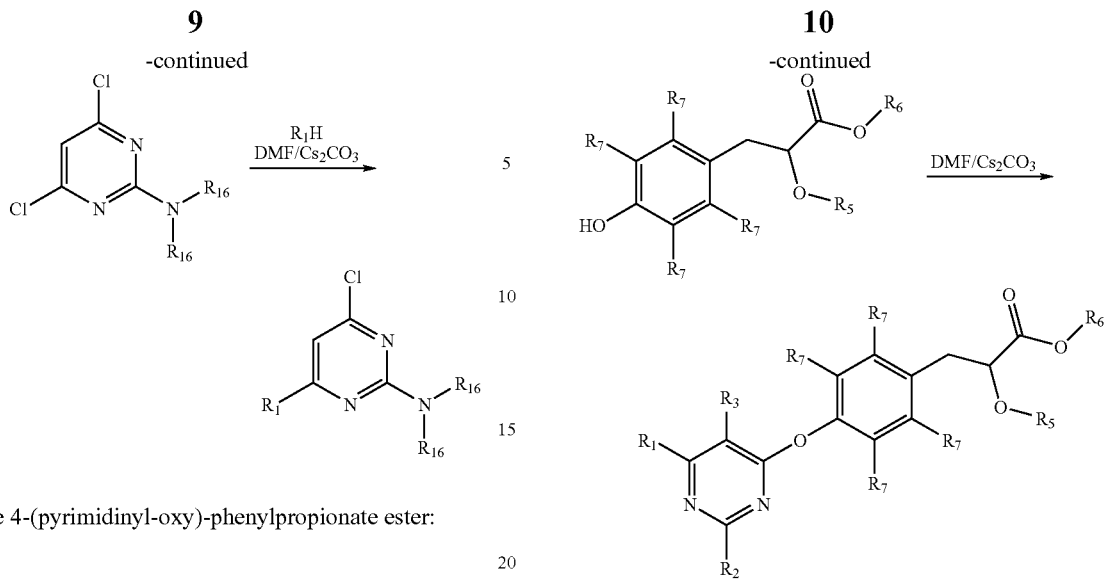
c) prepare 4-(pyrimidinyl-oxy)-phenylpropionate ester:
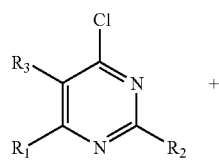
While all substitutes in the reaction are defined for Structural Formulas above beside $R_4$;
While $R_4$ is methyl, Compounds of the Structural Formula (II) have been formed by the procedures herein:
a) prepare the α,α-substituted phenylpropionate ester:
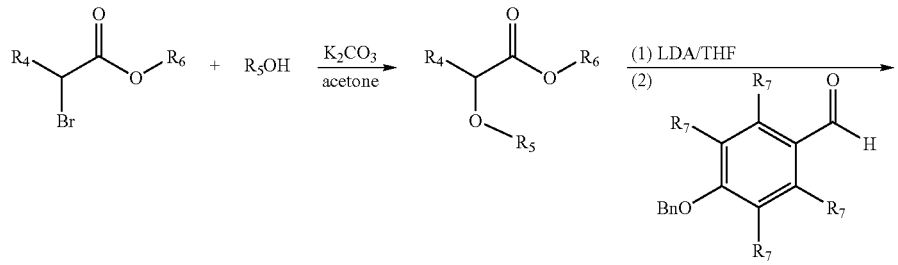
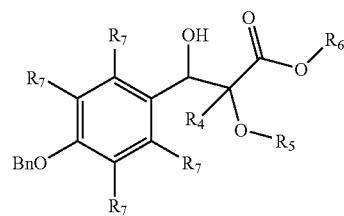

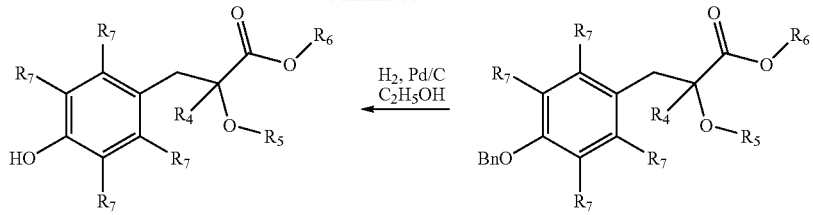

b) prepare substituted or unsubstituted pyridine:
prepare the pyridine by condensation reaction

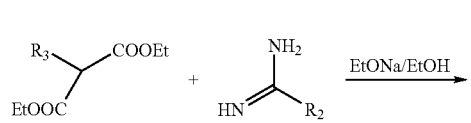

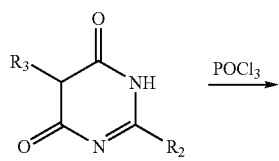

While $R_2$ is substituted amino, $R_3$ is H, $R_{16}$ is as defined in Structural Formula IV;

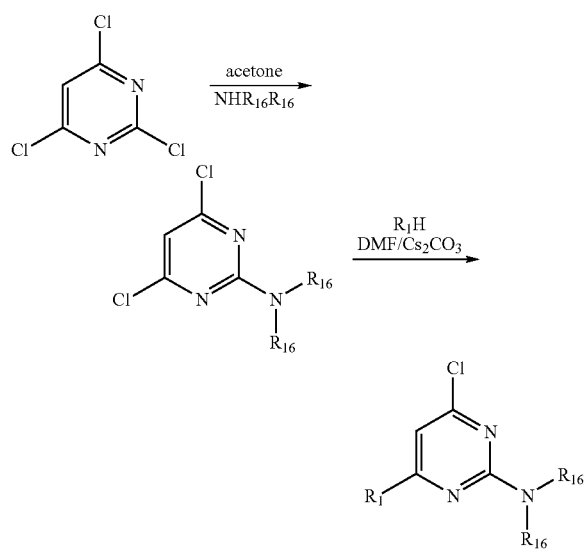

c) prepare 4-(pyrimidinyl-oxy)-phenylpropionate ester:

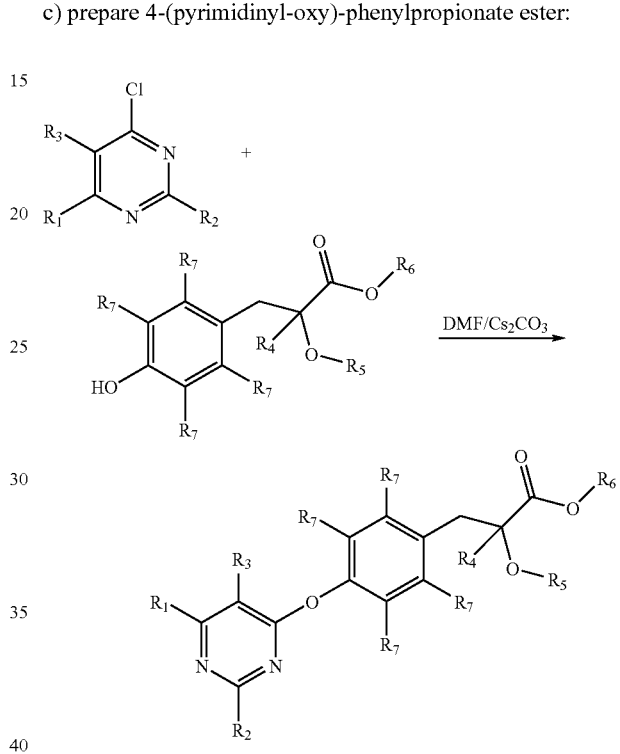

While all substitutes in the reaction are defined for Structural Formulas above;

In a third aspect of the present invention, the present invention also relates to pharmaceutical compositions which comprising: at least one compound selected from the compound of the present invention, enantiomer, racemic body, pharmaceutically acceptable salts, solvates and hydrates thereof; and pharmaceutically acceptable carrier, excipient or retarder.

In another embodiment, pharmaceutical compositions of the present invention could be in many forms, such as troche, capsule, powder, sirup, solution, suspending agent or aerosol.

In another embodiment, most suitably the composition will be formulated in unit dose form. Such unit dose will normally contain an amount of the compound of formula (I), enantiomer, racemic body, pharmaceutically acceptable salts, solvates and/or hydrates thereof in the range from 0.05 to 500 mg, more usually 0.5 to 200 mg, and more especially 0.1 to 100 mg.

In another embodiment, pharmaceutical compositions according to the present invention, may comprise typically the active ingredient comprising the formula (I) enantiomer, racemic body, pharmaceutically acceptable salts, solvates and/or hydrates thereof in an amount of at least 0.001-99.9 weight percent, more usually 0.01-99 weight percent, and more especially 0.1-90 weight percent. A weight percent is a ratio by weight of total by weight of total composition.

In further embodiment, pharmaceutical compositions could contain one or more other medicine in the treatment and prevention of polycystic kidney and cancer: ACE inhibitor, PPAR-γ agonist, for example, Enalapril, Benazepril, and Rosiglitazone. In another embodiment, pharmaceutical compositions contains: (a) as the active ingredient of compound of Formula Ienantiomer, racemic body, pharmaceutically acceptable salts, solvates and hydrates; (b) pharmaceutically acceptable carrier, excipient or retarder.

In further embodiment, pharmaceutical compositions according to the present invention, may comprise typically the active ingredient comprising the formula (I) enantiomer, racemic body, pharmaceutically acceptable salts, solvates and hydrates of which an amount of at least 0.001-99.9 weight percent, more usually 0.01-99 weight percent, and more especially 0.1-90 weight percent. A weight percent is a ratio by weight of total by weight of total composition.

In further embodiment, pharmaceutical compositions could contain one or more other medicine in the treatment and prevention of polycystic kidney and cancer: ACE inhibitor, PPAR-γ agonist, for example, Enalapril, Benazepril, Rosiglitazone.

In a fourth aspect of the present invention, the present invention provides a method for the preparation of a pharmaceutical composition, which comprises the step of mixing an amount of the compounds of the present invention, enantiomer, racemic body, pharmaceutically acceptable salts, solvates and/or hydrates thereof with pharmaceutically acceptable carrier, excipient or retarder and form a pharmaceutical composition. The amount of the compounds of the present invention, enantiomer, racemic body, pharmaceutically acceptable salts, solvates and/or hydrates thereof is at least 0.001-99.9 weight percent, more usually 0.01-99 weight percent, and more especially 0.1-90 weight percent, based on the total weight of the pharmaceutical composition.

The compounds of the present invention and pharmaceutically acceptable salts, solvates and hydrates thereof are believed to be effective in autosomal dominant polycystic kidney disease (ADPKD), autosomal recessive polycystic kidney disease (ARPKD), and cancer.

Therefore, in a fifth aspect of the present invention, the present invention provides a use of the compounds of the present invention in the preparation of a pharmaceutical composition for the treatment of polycystic kidney and/or cancer.

In some embodiments, said polycystic kidney is selected from autosomal recessive polycystic kidney disease or autosomal dominant pattern polycystic kidney disease. In other embodiments, said cancer is selected from colon, breast, lung and prostate, pituitary cancer, or leukemia.

In a sixth aspect of the present invention, the present invention provides a method for the treatment of the subject suffering from polycystic kidney and/or cancer, which comprising administrating an effective amount of the pharmaceutical composition of the present invention to the subject in need of such treatment.

In some embodiments, said polycystic kidney is selected from autosomal recessive polycystic kidney disease or autosomal dominant pattern polycystic kidney disease. In other embodiments, said cancer is selected from colon, breast, lung and prostate, pituitary cancer, or leukemia.

In further aspect of the present invention, the present invention provides a pharmaceutical composition for treating polycystic kidney and/or cancer, which comprising:
(i) at least one compound selected from the compound, pharmaceutically acceptable salts, solvates, or hydrates thereof of the invention; and
(ii) pharmaceutically acceptable carrier, excipient or retarder.

In some embodiments, said polycystic kidney is selected from autosomal recessive polycystic kidney disease or autosomal dominant pattern polycystic kidney disease. In other embodiments, said cancer is selected from colon, breast, lung and prostate, pituitary cancer, or leukemia.

BRIEF DESCRIPTION OF THE FIGURE

FIG. 1 is the Kaplan-Meier plot of Han: SPRD long-term treatment with the compound 2.

DETAILED DESCRIPTION OF THE INVENTION

We have found that the compounds defined in the present invention, or a pharmaceutically acceptable salt thereof, are effective PPARγ agonist, and accordingly have value in the treatment of polycystic kidney.

Active Ingredient

In the present invention, the technical terms "Active ingredient", "Active compound", "the compounds of the invention", "a new PPAR agonist" can be used interchangeably, these technical terms, are the Structural Formula I pyrimidinyl-aryl propionic acid and their enantiomer, racemic body, pharmaceutically acceptable salts, solvates and hydrates thereof.

Pharmaceutical Composition

The present invention also includes pharmaceutical compositions treating or preventing polycystic kidney, which contain: (a) as the active ingredient of compound of Formula I in treatment and prevention of polycystic kidney; (b) pharmaceutically acceptable carrier, excipient or retarder.

The term "contain" refers to one or more of the compounds of the invention above in combination with one or more pharmaceutically acceptable carriers. Thus, the term "main comprise of" and "comprise of" include the term "contain".

The term "pharmaceutically acceptable" means in the present description being useful in preparing a pharmaceutical composition that is generally safe, non-toxic and neither biologically nor otherwise undesirable and includes being useful for veterinary use as well as human pharmaceutical use.

As use herein, "pharmaceutically acceptable carrier" refers to solvent, suspending agent or excipient that transmit active ingredient or pharmaceutically acceptable salts to human or veterinary. The carrier could be liquid or solid.

As use herein, Pharmaceutical compositions according to the present invention, may comprise typically the active ingredient comprising the formula (I) or pharmaceutically acceptable carrier or excipient or retarder of which an amount of at least 0.001-99.9 weight percent, more usually 0.01-99 weight percent, and more especially 0.1-90 weight percent. A weight percent is a ratio by weight of total by weight of total composition.

In another embodiment, a typical pure compounds of the formula (I) or pharmaceutically acceptable carrier or excipient or retarder comprises greater than 65% by weight of total weight, the others comprise 0.5-40%, or more preferably 1-20%, or even more preferably 1-10%.

As use herein, most suitably the composition will be formulated in unit dose form. Such unit dose will normally contain an amount of the compound of formula (I), enantiomer, racemic body, pharmaceutically acceptable salts, solvates and hydrates in the range from 0.05 to 500 mg, more usually 0.5 to 200 mg, and more especially 0.1 to 100 mg.

Further, as used herein, pharmaceutical compositions could contain one or more other medicine in the treatment and prevention of polycystic kidney: ACE inhibitor, PPAR-γ agonist and so on, for example, Enalapril, Benazepril, and Rosiglitazone.

When combination treatment or prevention of polycystic kidney comprises the compound of Formula (I), dosage of the active ingredient is used as usually, or even lower.

Form of Medication and Dose

Pharmaceutical compositions of the present invention could be in many forms, such as troche, capsule, powder, sirup, solution, suspending agent or aerosol, compound of formula (I) could be maintained in suitable solid, liquid carrier or dilution. Pharmaceutical compositions of the present invention could also be deposited in suitable disinfector of injection or drop.

The compounds of formula (I) or pharmaceutical compositions of the invention can also be administered in a targeted drug delivery system, such as, for example, ora, nose, skin, lung or gastrointestinal tract. Oral is optional route of administration, usually 0.5 mg-200 mg/kg once or several times a day. In spite of administration, the suitable dosage is decided according to treatment. The amount of compound or composition administered to a patient will vary depending upon the compound used, the manner of administration and the state of the patient.

On the other hand, the active ingredient may be administered in an amount in the range of about 1-300 mg/kg per day, typically administered 1 to 3 times per day, or administered by the technique of delayed release. Especially most mammal, the unit dosage per day contain from 5-1000 mg, more preferably 10-500 mg. For oral administration, a dosage of the pharmaceutically acceptable carrier contain from 1-200 mg of the active ingredient. In therapeutic applications, the desired dose may conveniently be presented as divied doses administered at appropriate intervals.

The compounds of formula (I) or pharmaceutical compositions of the invention can also be administered in a targeted drug delivery system by oral, intravenous, intramuscularly, subcutaneously. According to be prone to prepare and administration, the more preferable pharmaceutical compositions is solid, especially troche and capsule. Oral administration is more preferable.

A solid carrier can be starch, lactose, calcium phosphate, fibrin, sucrose and bolus alba, and a liquid carrier can be aqua sterilisata, polyethylene glycol, surface active agent and edible oil (corn oil, arachis oil and benne oil) and so on. Adjuvant could also be used, for example, flavoring agent, pigment, antiseptic and antioxidant such as vitamin E, vitamin C, BHT and BHA.

The compounds of formula (I) or pharmaceutical compositions of the invention can also be administered in a targeted drug delivery system by intestines and stomach or abdominal cavity. Solution or suspension of the active ingredient can also be prepared in water containing suitable surfactant (such as hydroxypropyl cellulose). Its dispersed liquid can also be prepared in glycerin, polyethylene glycol, or mixture of them. Under ordinary conditions of storage and use, these preparations contain a preservative to prevent the growth of microorganisms.

The injectable solutions prepared in this manner can then be administered intravenously, intraperitoneally, subcutaneously, or intramuscularly, with intramuscular administration being preferred in humans. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each svringability exists. It must be stable under the conditions of manufacture and storage and must be preserved against any contamination. The carrier can be solvent or dispersion medium containing, for example, eater, preferably in physiologically compatible buffers such as Hank's solution, Ringer's solution, or physiological saline buffer, ethanol, polyol (e.g. glycerol, propylene glycol and liquid polyethylene glycol), propylene glycol and suitable mixtures thereof, and vegetable oils.

The compounds of formula (I) and their pharmaceutically acceptable salts, solvates can be used in combination with other medicine of treatment or prevention of polycystic kidney. When two or more medicine is used, the effect of drug combination is generally better than that of signal drug.

Synthesis and Processes

General Procedures of Compound (I):

In the presence of cesium carbonate, compound (Ia) is treated with compound (Ib) in a polar solvent at a temperature of about 60° C. to about 100° C., to form compound (I):

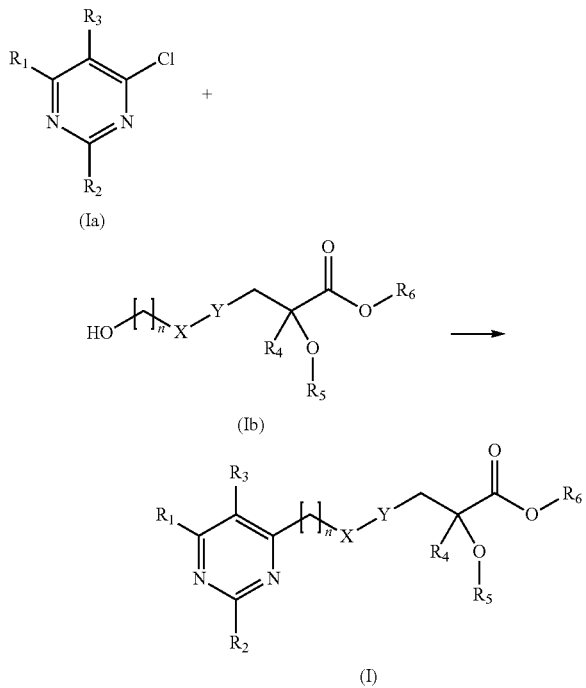

While, all substitutes in the reaction are defined above.

In one embodiment, the customary organic solvents which not change under the reaction conditions: 1,2-dimethoxyethane, THF, DMF, dichloromethane, acetone, EA, methanol, ethanol, water, or mixed solvent such as THF, water and methanol.

In another embodiment, the reaction temperature is between 60° C. and 100° C., preferably between 70° C. to 90° C.; the reaction time is 15 minutes to 2 days, preferable is 30 minutes to 1 day.

General Procedures of Compound (II):

1. while $R_4$ is H, the Compounds have been formed by the procedures herein:
   a) α-substituted phenylpropionate ester:
      a1) Form the enol by potassium tert-butoxide in a tert-butyl alcohol solvent,
      a2) Form the phenol by treated with hydrogen in the presence of palladium on carbon (Pd/C) catalyst,

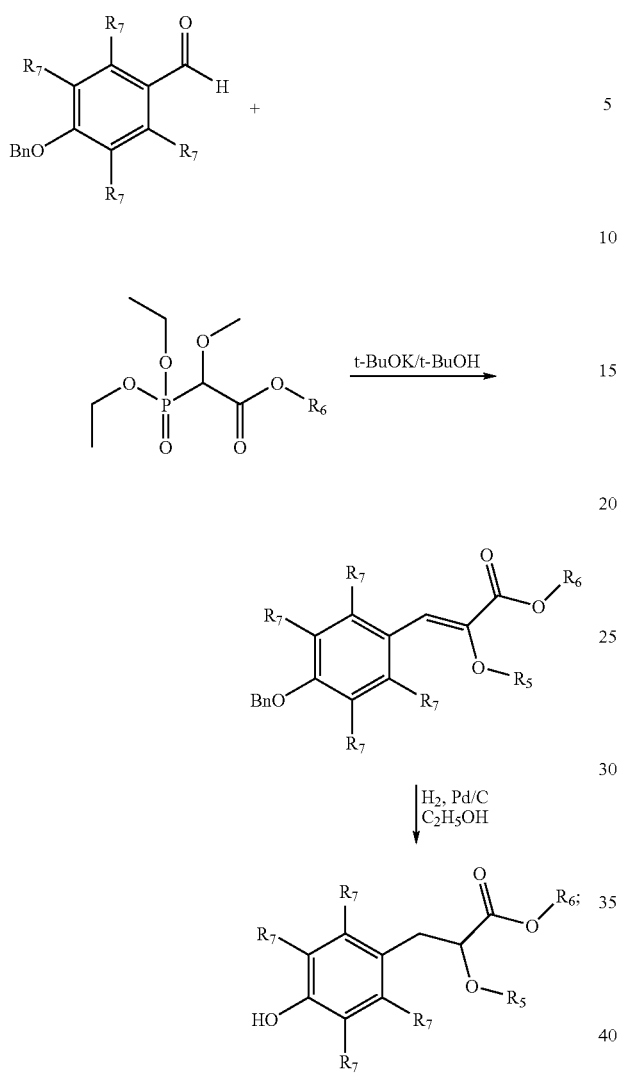

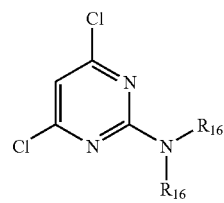

Or prepare the pyridine by condensation reaction b1') the diethyl malonate and amidine was heated to cyclize in the present of b2') use hot $POCl_3$ to chloridate, b3') In the presence of cesium carbonate/DMF, to form the pyrimidine,

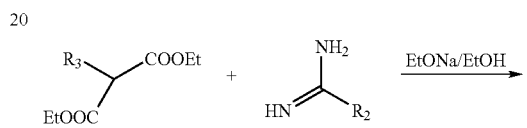

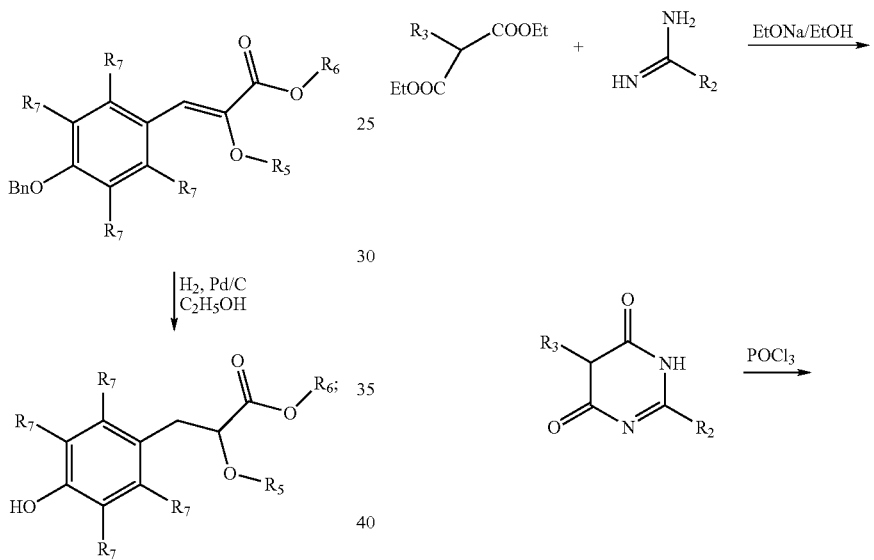

b) prepare substituted or unsubstituted pyridine:

b1) At a temperature of 0° C., the 2,4,6-Trichloro-pyrimidine was dissolved in an anhydrous aprotic solvent such as acetone or THF, added the amino, to form the 2-amino-pyrimidine, b2) In the presence of cesium carbonate/DMF, to form the pyrimidine,

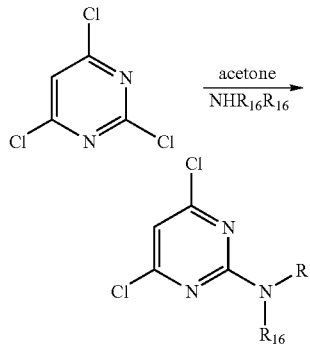

c) prepare 4-(pyrimidinyl-oxy)-phenylpropionate ester:

c1) In the presence of cesium carbonate/DMF, to form the pyrimidine, c2) In the presence of THF/$CH_3OH$/$H_2O$/KOH, hydrolyze to form the acid,

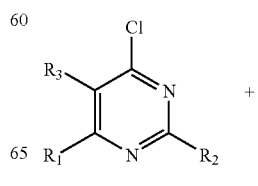 +

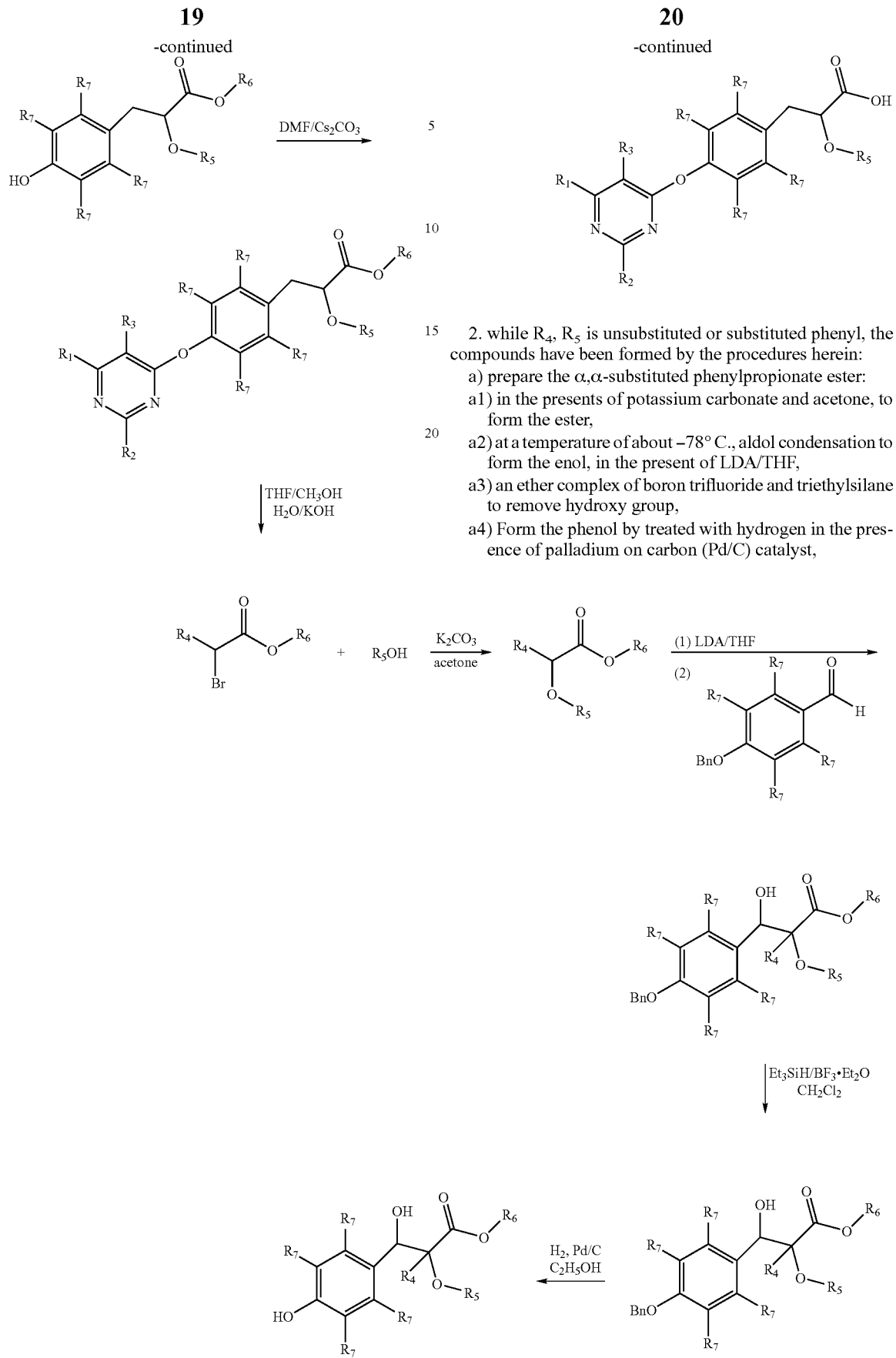

2. while $R_4$, $R_5$ is unsubstituted or substituted phenyl, the compounds have been formed by the procedures herein:
   a) prepare the α,α-substituted phenylpropionate ester:
   a1) in the presents of potassium carbonate and acetone, to form the ester,
   a2) at a temperature of about −78° C., aldol condensation to form the enol, in the present of LDA/THF,
   a3) an ether complex of boron trifluoride and triethylsilane to remove hydroxy group,
   a4) Form the phenol by treated with hydrogen in the presence of palladium on carbon (Pd/C) catalyst, b) prepare substituted or unsubstituted pyridine:
b1) At a temperature of 0° C., the 2,4,6-Trichloro-pyrimidine was dissolved in an anhydrous aprotic solvent such as acetone or THF, added the amino, to form the 2-amino-pyrimidine,
b2) In the presence of cesium carbonate/DMF, to form the pyrimidine,

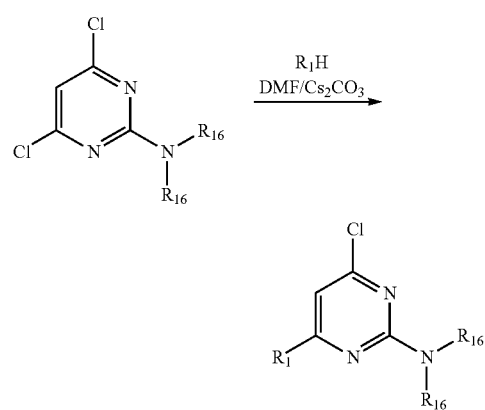

Or prepare the pyridine by condensation reaction
b1') the diethyl malonate and amidine was heated to cyclize in the present of EtONa/EtOH
b2') use hot POCl₃ to chloridate,
b3') In the presence of cesium carbonate/DMF, to form the pyrimidine,

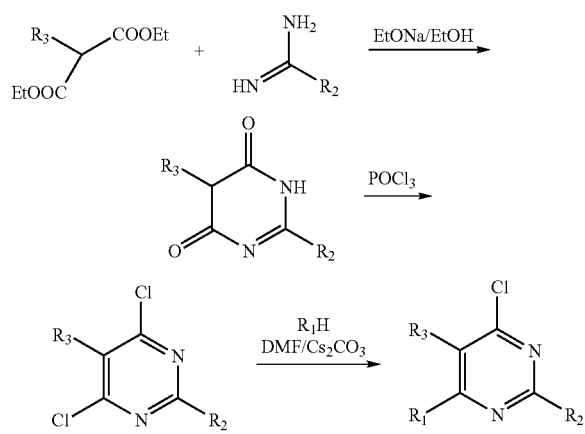

c) prepare 4-(pyrimidinyl-oxy)-phenylpropionate ester:
c1) In the presence of cesium carbonate/DMF, to form the pyrimidine,
c2) In the presence of THF/CH₃OH/H₂O/KOH, hydrolyze to form the acid,

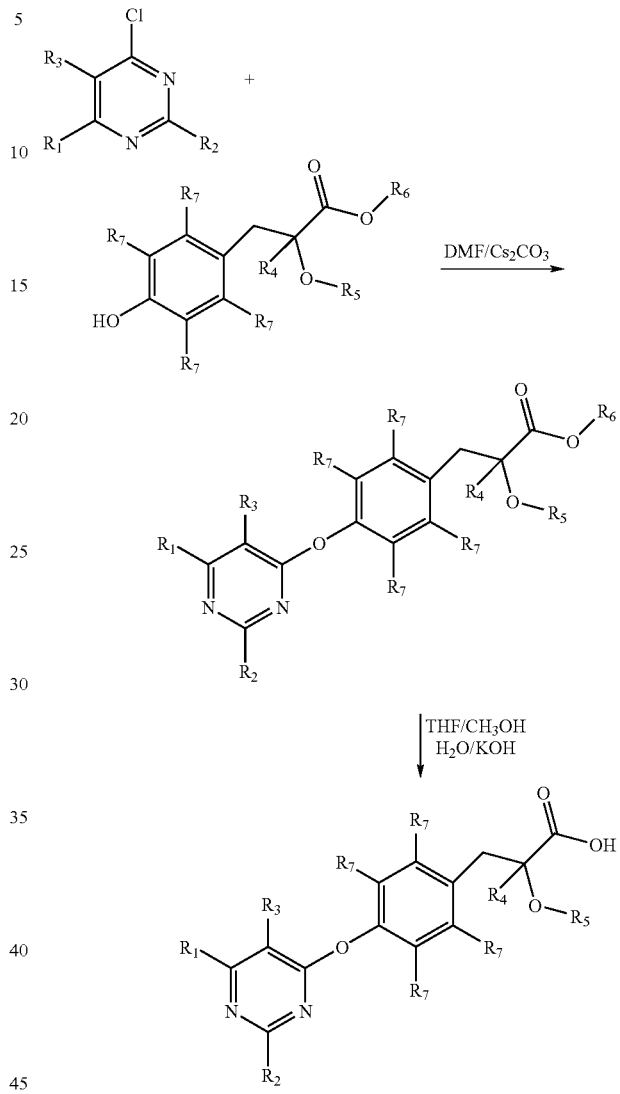

As used herein, the reaction described above may be performed under standard conditions. For example, the solvent generally is inert solvent: 1,2-dimethoxyethane, THF, DMF or mixed solvent and so on. The reaction temperature is carried out between room temperature and refluence temperature; and the reaction time is half an hour to 1 day, which can be change according to the material, solvent and reaction temperature.

As used herein, the term "room temperature" is environmental temperature, generally is 25°.

The terms used to describe the instant invention have the following meanings herein.

As used herein, "alkenyl" is straight-chain or branched-chain alkenyl having from two to six carbon atoms, such as ethylene, allyl, acryl, isopropenyl, 1-butenyl, 2-butenyl and so on;

The term "cycloalkyl groups", as used herein, include cyclopropyl, cyclobutyl, cyclopentyl, cyclohexyl, or cycloheptyl;

As used herein, "$C_{1-6}$ alkyl" is straight-chain or branched-chain alkyl having from one to four carbon atoms, such as methyl, ethyl, propyl, isopropyl, butyl, isobutyl, Sec-butyl, Tert-butyl, pentyl, hexyland so on;

The term "$C_{1-8}$ alkoxyl" is straight-chain or branched-chain alkoxyl having from one to four carbon atoms, such as methoxyl, ethoxyl, propoxyl, isopropoxyl, butoxyl, isobutoxyl, Sec-butoxyl, Tert-butoxyl, pentyl, hexyl, heptyl, octyl and so on;

As used herein, "halogen" include fluoro, chloro, bromo or iodo;

The term "$C_1$-$C_6$ haloalkyl", as used herein, is $C_{1-6}$ alkyl substituent by one to six same or different halogen, such as trifluoromethyl, pentafluoroethyl, and so on;

The term "$C_{1-4}$ acyl", as used herein, is straight-chain or branched-chain acyl having from one to four carbon atoms, such as formyl, acetyl, propionyl, butyryl, isobutyryl, and so on;

The term "aryl", as used herein, include aralkyl having simple to three rings, such as phenyl, naphthyl, and so on;

The term "aralkyl", as used herein, is $C_{1-6}$ alkyl substituent by aryl;

As used herein, "unsubstituted or substituted heteroaryl which contains one or two oxygen or nitrogen" include furyl, pyridyl, pyrimidinyl, pyrrolyl, pyrazinyl, pyridazinyl, and so on;

As used herein, "$C_3$-$C_6$ heterocycloalkyl" include pyrrolidinyl, piperidinyl, morpholinyl, piperazidinyl, and so on;

In the instant invention, Compounds of the Structural Formula (I) could be unsubstituted or substituted by one to three group described above, which usually is selected from halogen, $C_{1-4}$ alkyl, amino, hydroxyl, trifluoromethyl, trifluoromethoxy and so on.

Main advantages of the invention are:

(1) Compounds of the invention are new PPAR-γ agonists, by transient transfection and transcription assay;

(2) According to experiments in vivo and vitro, compounds of the invention are the same as or even more therapeutic efficacy in treatment of polycystic kidney and cancrer, meanwhile decreasing side-effect, compared to current medicine. Thus, compounds of the invention are especially practical importance in treatment of polycystic kidney and cancer.

EXEMPLIFICATION

Exemplified Compounds

Example 1 rac-3-{4-[2-Amino-6-(4-benzyl-piperazin-1-yl)-pyrimidin-4-yloxy]-phenyl}-2-ethoxy-propionic acid

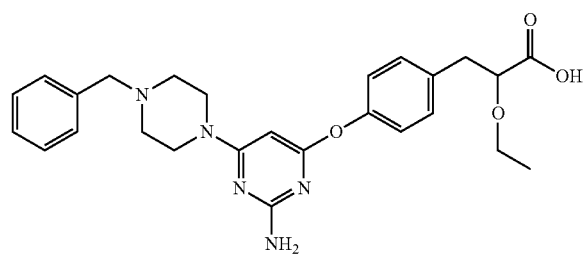 [SMILES: CCOC(Cc1ccc(Oc2cc(N3CCN(Cc4ccccc4)CC3)nc(N)n2)cc1)C(=O)O]

The tile compound, shown above, was made as described below.

Step A 3-(4-Benzyloxy-phenyl)-2-ethoxy-acrylic acid ethyl ester

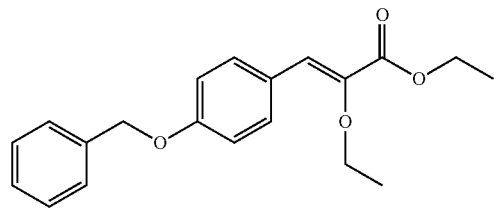 [SMILES: CCOC(=O)/C(=C/c1ccc(OCc2ccccc2)cc1)OCC]

P(OEt)$_3$ was added dropwise to a mixture of tent-butyl methyl ether 55 mL) and potassium tert-butoxide (4.65 g, 41.4 mmol) under a nitrogen atmosphere at 20-30° C. 4-Benzyloxybenzaldehyde (4.61 g, 21.7 mmol) was added in portions to this mixture at 5° C. followed by the addition of tert-butyl alcohol (6.70 g). The reaction mixture was allowed to reach 15° C. and stirred at this temperature for approximately 30 min, after which the reaction was completed (as judged by TLC). Water (30 mL) was added at 5-10° C., and the phases were allowed to separate. The organic phase was concentrated in vacuo, and ethanol (30 mL) was added to the stirred solution. After crystallization had occurred, water (18 mL) was added to the suspension. The light-yellow title compound was filtered off, washed with ethanol/water (1:1 v/v), and dried in vacuo to yield 6.52 g (92% yield).

$^1$H NMR, 400 MHz (acetone-d6): δ 1.12 (t, J=7 Hz), 1.32 (t, J=7 Hz), 1.33 (t, J=7 Hz), 3.91 (q, J=7 Hz), 4.00 (q, J=7 Hz), 4.12 (q, J=7 Hz), 4.24 (q, J=7 Hz), 5.12 (s), 5.17 (s), 6.10 (s), 6.93 (s), 6.94 (d, J=9 Hz), 7.05 (d, J=9 Hz), 7.15 (d, J=9 Hz), 7.32-7.42 (m), 7.46-7.50 (m), 7.81 (d, J=9 Hz).

Step B

2-Ethoxy-3-(4-hydroxy-phenyl)-propionic acid ethyl ester

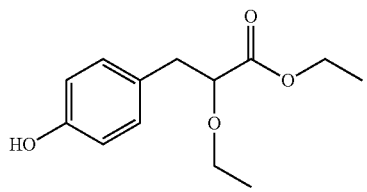 [SMILES: CCOC(=O)C(Cc1ccc(O)cc1)OCC]

Ethyl E/Z-3-(4-benzyloxyphenyl)-2-ethoxyacrylate (20.0 g, 61.3 mmol) dissolved in tert-butyl methyl ether (40 mL) charged with palladium on carbon (5%) (1.0 g, Engelhard Tech code no. 4531) was hydrogenated with vigorous stirring at atmospheric pressure at room temperature for 2-3 days.

The catalyst was filtered off and washed with a few milliliters of tent-butyl methyl ether. The combined filtrates were concentrated in vacuo to yield 14.5 g (99% yield) of the title compound as a viscous oil, which crystallizes upon standin.

$^1$H NMR, 400 MHz (acetone-d6): δ 1.09 (t, 3H, J=7 Hz), 1.17 (t, 3H, J=7 Hz), 2.83-2.91 (m, 2H), 3.35 (d, q, 1H, J=7 and 14 Hz), 3.55 (d, q, 1H, J=7 and 14 Hz), 3.98 (d, d, 1H, J=4, 7 Hz), 4.10 (q, 2H, J=7 Hz), 6.74 (d, 2H, J=9 Hz), 7.06 (d, 2H, J=9 Hz), 8.08 (s, 1H). $^{13}$C NMR (acetone-d6), 100 MHz: δ 4.9, 15.9, 39.5, 61.3, 66.6, 81.5, 116.2, 129.3, 131.6, 157.3, 173.0.

Step C rac-3-{4-[2-Amino-6-(4-benzyl-piperazin-1-yl)-pyrimidin-4-yloxy]-phenyl}-2-ethoxy-propionic acid ethyl ester

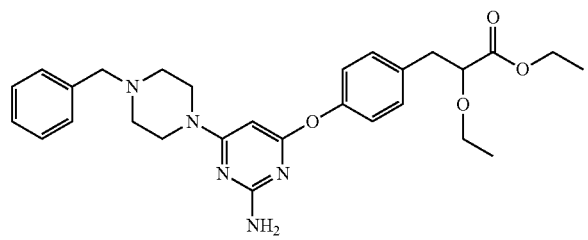 [SMILES: CCOC(=O)C(Cc1ccc(Oc2cc(N3CCN(Cc4ccccc4)CC3)nc(N)n2)cc1)OCC]

Phenol (33.3 mmol), 4-(4-Benzyl-piperazin-1-yl)-6-chloro-pyrimidin-2-ylamine (33.3 mmol) and Cs$_2$CO$_3$ (36.6 mmol) were combined in anhydrous N,N-dimethylformamide (DMF) (40 mL) and stirred at 90° C. in dry atmosphere over night. The DMF was removed in vacuo, the residue was dissolved in acetone, and rac-3-{4-[2-Amino-6-(4-benzyl-piperazin-1-yl)-pyrimidin-4-yloxy]-phenyl}-2-ethoxy-propionic acid ethyl ester (13.2 g, 70%) is crystallized form acetone.

Step D rac-3-{4-[2-Amino-6-(4-benzyl-piperazin-1-yl)-pyrimidin-4-yloxy]-phenyl}-2-ethoxy-propionic acid

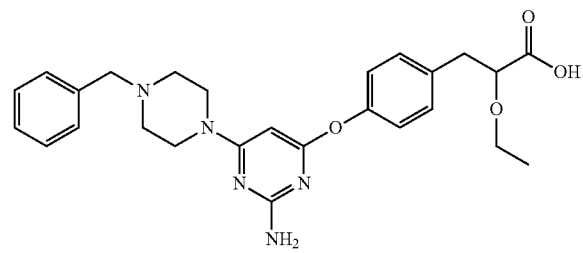 [SMILES: CCOC(Cc1ccc(Oc2cc(N3CCN(Cc4ccccc4)CC3)nc(N)n2)cc1)C(=O)O]

rac-3-{4-[2-Amino-6-(4-benzyl-piperazin-1-yl)-pyrimidin-4-yloxy]-phenyl}-2-ethoxy-propionic acid ethyl ester was dissolved in tetrahydrofuran (THF)/alcohol solvent in the presence of an excess of aqueous potassium hydrate, the reaction is allowed to proceed for about 20 h. After most of the solve was removed in vacuo, the aqueous solution was acidified to pH 6, the white product was precipitated, then filtered through celite, rac-3-{4-[2-Amino-6-(4-benzyl-piperazin-1-yl)-pyrimidin-4-yloxy]-phenyl}-2-ethoxy-propionic acid (95%) was collected.

Example 2 rac-3-{4-[2-Amino-6-(4-benzyl-piperazin-1-yl)-pyrimidin-4-yloxy]-phenyl}-2-methyl-2-phenoxy-propionic acid

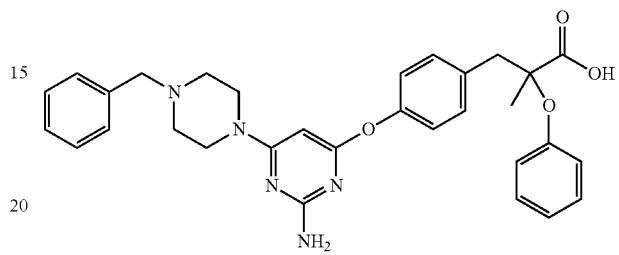

The tile compound, shown above, was made as described below.

Step A

2-Phenoxypropionic acid ethyl ester

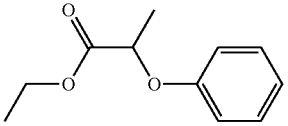

Phenol (24.28 g, 0.25 mol), potassium carbonate (39.2 g 0.28 mol), and ethyl 2-bromoproionate (46.7 g, 0.25 mol) were combined in acetone (200 mL) and stirred at room temperature over night. The acetone was removed in vacuo, the residue was purified in silica to provide a golden oil (50 g, 90%), R$_f$=0.80 in 10:1 ethyl acetate: petroleum ether.

$^1$H NMR (250 MHz, CDCl$_3$): δ 1.24 (t, 3H, J=7.2 Hz), 1.66 (d, 3H, J=6.1 Hz), 4.26 (q, 2H, J=7.2 Hz), 4.79 (q, 1H, J=6.1 Hz), 6.93 (d, 2H, J=7.8 Hz), 7.02 (t, 1H, J=7.9 Hz), 7.31 (d, 2H, J=7.8 Hz); MS [EI$^+$] 195 (M+H)$^+$.

Step B

4-Benzyloxy-benzaldehyde

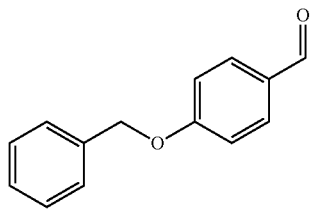 [SMILES: O=Cc1ccc(OCc2ccccc2)cc1]

4-hydroxy-benzaldehyde (57.64 g, 0.47 mol) and potassium carbonate (71.6 g, 0.51 mol), which were combined in acetone (200 mL), were reacted with benzyl bromine (80.73 g, 0.51 mol) and stirred at room temperature over night. The acetone was removed in vacuo, and the 4-Benzyloxy-benzaldehyde (71.6 g), as a white solid, is crystallized form ethyl acetate.

Step C

2-Phenoxy-3-(4-benzyloxyphenyl)-3-hydroxy-2-methyl-propionic acid ethyl ester

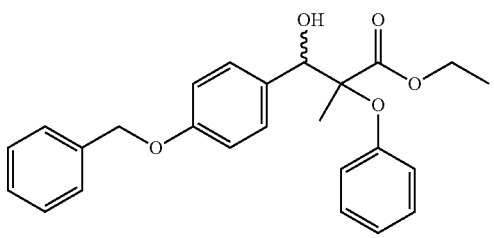 [SMILES: CCOC(=O)C(C)(Oc1ccccc1)C(O)c1ccc(OCc2ccccc2)cc1]

A solution of lithium diisopropylamide (LDA) (26 mL, 52 mmol, 2 M in tetrahydrofuran) was cooled to −78° C. and then added to a solution of 2-Phenoxypropionic acid ethyl ester (10 g, 51 mmol) in anhydrous tetrahydrofuran (THF) (80 mL) also cooled to −78° C. under an atmosphere of nitrogen. After 30 min, 4-benzyloxybenzaldehyde (10 g, 47 mmol) was added in one portion. After stirring over night, the reaction mixture was quenched with saturated solution of aqueous NH$_4$Cl (10 mL) and the mixture allowed to warm to ambient temperature. The biphasic mixture was diluted with dichloromethane and partitioned, and the organic layer was washed with brine, dried over MgSO$_4$ and concentrated in vacuo. The residue was purified in silica to provide colorless oil (8.9 g, 47%), R$_f$=0.30 in 10:1 ethyl acetate: petroleum ether.

Step D

2-Phenoxy-3-(4-benzyloxyphenyl)-2-methyl-propionic acid ethyl ester

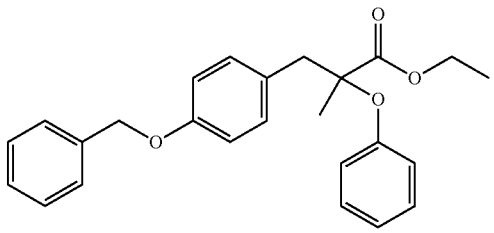 [SMILES: CCOC(=O)C(C)(Cc1ccc(OCc2ccccc2)cc1)Oc1ccccc1]

2-Phenoxy-3-(4-benzyloxyphenyl)-3-hydroxy-2-methyl-propionic acid ethyl ester (20.4 g, 50 mmol) in anhydrous CH$_2$Cl$_2$ (200 mL) was cooled to 0° C. and treated with BF$_3$-Et$_2$O (6.12 mL, 50 mmol) and triethylsilane (8.16 mL, 9.5 mmol). The mixture was stirred over night. Saturated aqueous Na$_2$CO$_3$ (75 mL) was added and the mixture was stirred vigorously. The solution was partitioned and the organic layer was washed twice with water and brine, dried over MgSO$_4$ and concentrated in vacuo, then purified in silica to provide a colorless oil (9.9 g, 51%)

$^1$HNMR (300 MHz, CDCl$_3$) δ1.22 (t, 3H, J=7.1 Hz), 1.40 (s, 3H), 3.13 (d, 1H, J=13.8 Hz), 3.26 (d, 1H, J=13.8 Hz), 4.22 (q, 2H, J=7.1 Hz), 5.05 (s, 2H), 6.83 (d, 2H), 6.91 (d, 2H), 6.98 (t, 1H), 7.17~7.24 (m, 5H), 7.34 (t, 1H), 7.36~7.42 (m, 3H).

Step E 3-(4-Hydroxyphenyl)-2-methyl-2-phenoxypropionic acid ethyl ester

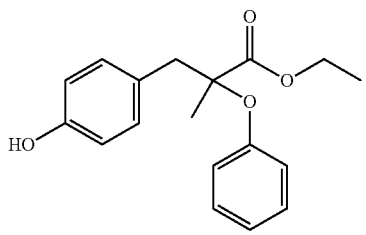 [SMILES: CCOC(=O)C(C)(Cc1ccc(O)cc1)Oc1ccccc1]

2-Phenoxy-3-(4-benzyloxyphenyl)-2-methyl-propionic acid ethyl ester (24.1 g, 59.3 mmol) was dissolved in ethanol (200 mL) and treated with 10% palladium on carbon (2.41 g), and then stirred under an atmosphere of hydrogen for 20 h. The suspension was filtered through celite and concentrated in vacuo to produce 3-(4-hydroxyphenyl)-2-methyl-2-phenoxypropionic acid ethyl ester colorless oil (16.9 g, 95%).

$^1$H NMR δ1.22 (t, 3H, J=7.1 Hz), 1.40 (s, 3H), 3.09 (d, 1H, J=13.5 Hz), 3.26 (d, 1H, J=13.5 Hz), 4.02 (q, 2H, J=7.1 Hz), 5.01 (s, 2H), 6.81~6.93 (m, 3H), 7.14-7.22 (m, 2H), 7.27~7.40 (m, 31-1).

Step F 4-(4-Benzyl-piperazin-1-yl)-6-chloro-pyrimidin-2-ylamine

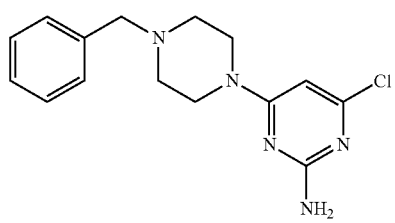 [SMILES: Nc1nc(Cl)cc(N2CCN(Cc3ccccc3)CC2)n1]

1-Benzyl-piperazine (5.86 g, 33.3 mmol), 2-amino-4,6-dichloro-pyrimidine (5.46 g, 33.3 mmol) and Cs$_2$CO$_3$ (10.8 g, 36.6 mmol) were combined in anhydrous N,N-dimethylformamide (DMF) (50 mL) and stirred at 90° C. in dry atmosphere for 5 h. The DMF was removed in vacuo, the residue was dissolved in acetone, and 4-(4-Benzyl-piperazin-1-yl)-6-chloro-pyrimidin-2-ylamine (8.5 g, 86%) was is crystallized form acetone.

Step G rac-3-{4-[2-Amino-6-(4-benzyl-piperazin-1-yl)-pyrimidin-4-yloxy]-phenyl}-2-methyl-2-phenoxy-propionic acid ethyl ester

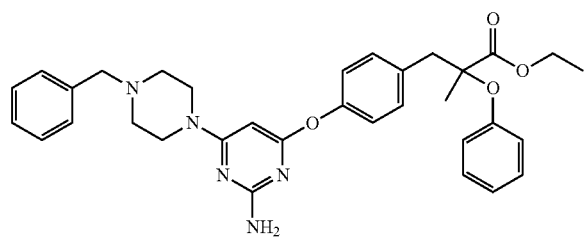 [SMILES: CCOC(=O)C(C)(Cc1ccc(Oc2cc(N3CCN(Cc4ccccc4)CC3)nc(N)n2)cc1)Oc1ccccc1]

Phenol (10 g, 33.3 mmol), 4-(4-Benzyl-piperazin-1-yl)-6-chloro-pyrimidin-2-ylamine (10 g, 33.3 mmol) and $Cs_2CO_3$ (10.8 g, 36.6 mmol) were combined in anhydrous N,N-dimethylformamide (DMF) (40 mL) and stirred at 90° C. in dry atmosphere over night. The DMF was removed in vacuo, the residue was dissolved in acetone, and 3-{4-[2-Amino-6-(4-benzyl-piperazin-1-yl)-pyrimidin-4-yloxy]-phenyl}-2-methyl-2-phenoxy-propionic acid ethyl ester. (13.2 g, 70%) is crystallized form acetone.

Step H rac-3-{4-[2-Amino-6-(4-benzyl-piperazin-1-yl)-pyrimidin-4-yloxy]-phenyl}-2-methyl-2-phenoxy-propionic acid

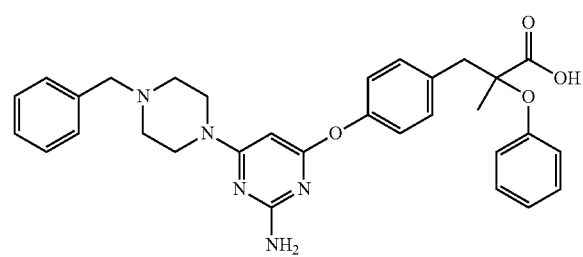 [SMILES: CC(Cc1ccc(Oc2cc(N3CCN(Cc4ccccc4)CC3)nc(N)n2)cc1)(Oc1ccccc1)C(=O)O]

3-{4-[2-Amino-6-(4-benzyl-piperazin-1-yl)-pyrimidin-4-yloxy]-phenyl}-2-methyl-2-phenoxy-propionic acid ethyl ester was dissolved in tetrahydrofuran (THF)/alcohol solvent in the presence of an excess of aqueous potassium hydrate, the reaction is allowed to proceed for about 20 h. After most of the solve was removed in vacuo, the aqueous solution was acidified to pH 6, the white product was precipitated, then filtered through celite, rac-3-{4-[2-Amino-6-(4-benzyl-piperazin-1-yl)-pyrimidin-4-yloxy]-phenyl}-2-methyl-2-phenoxy-propionic acid (11 g, 95%) was collected.

$^1$HNMR (300 MHz, $CD_3OD$): δ 1.40 (s, 3H), 3.00 (d, d, 4H), 3.20 (q, 2H), 3.70 (d, d, 4H), 4.05 (s, 2H), 5.19 (s, 1H), 6.88~7.06 (m, 5H), 7.20~7.37 (m, 4H), 7.46~7.55 (m, 5H), EI-MS: m/e 539 ($M^+$).

Example 3

S-3-{4-[2-Amino-6-(4-benzyl-piperazin-1-yl)-pyrimidin-4-yloxy]-phenyl}-2-methyl-2-phenoxy-propionic acid

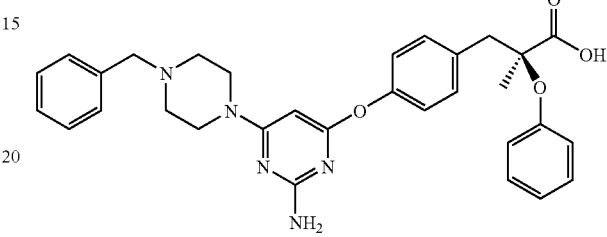

3-{4-[2-Amino-6-(4-benzyl-piperazin-1-yl)-pyrimidin-4-yloxy]-phenyl}-2-methyl-2-phenoxy-propionic acid ethyl ester were separated by chiral chromatography using a Chiralpak AD 4.6 mm×250 mm column.

S-3-{4-[2-Amino-6-(4-benzyl-piperazin-1-yl)-pyrimidin-4-yloxy]phenyl}-2-methyl-2-phenoxy-propionic acid ethyl ester was dissolved in tetrahydrofuran (THF)/alcohol solvent in the presence of an excess of aqueous potassium hydrate, the reaction is allowed to proceed for about 20 h. After most of the solve was removed in vacuo, the aqueous solution was acidified to pH 6, the white product was precipitated, then filtered through celite, S-3-{4-[2-Amino-6-(4-benzyl-piperazin-1-yl)-pyrimidin-4-yloxy]-phenyl}-2-methyl-2-phenoxy-propionic acid (10 mg) was collected. ee: 99% (AD-H, 0.46 cm I.D.×25 cm)

$^1$HNMR (300 MHz, $CD_3OD$): δ 1.40 (s, 3H), 3.00 (d, d, 4H), 3.20 (q, 2H), 3.70 (d, d, 4H), 4.05 (s, 2H), 5.19 (s, 1H), 6.88~7.06 (m, 5H), 7.20~7.37 (m, 4H), 7.46~7.55 (m, 5H), EI-MS: m/e 539 ($M^+$).

Example 4

R-3-{4-[2-Amino-6-(4-benzyl-piperazin-1-yl)-pyrimidin-4-yloxy]-phenyl}-2-methyl-2-phenoxy-propionic acid

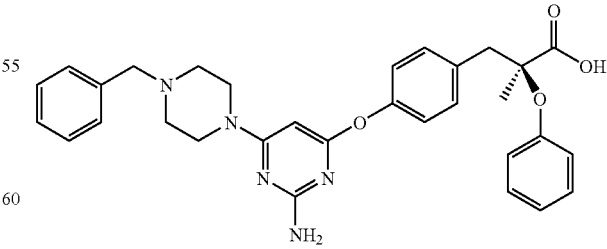

3-{4-[2-Amino-6-(4-benzyl-piperazin-1-yl)-pyrimidin-4-yloxy]-phenyl}-2-methyl-2-phenoxy-propionic acid ethyl ester were separated by chiral chromatography using a Chiralpak AD 4.6 mm×250 mm column.

R-3-{4-[2-Amino-6-(4-benzyl-piperazin-1-yl)-pyrimidin-4-yloxy]-phenyl}-2-methyl-2-phenoxy-propionic acid ethyl ester was dissolved in tetrahydrofuran (THF)/alcohol solvent in the presence of an excess of aqueous potassium hydrate, the reaction is allowed to proceed for about 20 h. After most of the solve was removed in vacuo, the aqueous solution was acidified to pH 6, the white product was precipitated, then filtered through celite, R-3-{4-[2-Amino-6-(4-benzyl-piperazin-1-yl)-pyrimidin-4-yloxy]-phenyl}-2-methyl-2-phenoxy-propionic acid (10 mg, 95%) was collected. ee: 99% (AD-H, 0.46 cm I.D.×25 cm)

$^1$HNMR (300 MHz, CD$_3$OD): δ 1.40 (s, 3H), 3.00 (d, d, 4H), 3.20 (q, 2H), 3.70 (d, d, 4H), 4.05 (s, 2H), 5.19 (s, 1H), 6.88~7.06 (m, 5H), 7.20~7.37 (m, 4H), 7.46~7.55 (m, 5H), EI-MS: m/e 539 (M$^+$).

Example 5

3-{4-{2-Amino-6-[4-(1,3-dihydro-isobenzofuran-5-ylmethyl)-piperazin-1-yl]-pyrimidin-4-yloxy}-phenyl}-2-methyl-2-phenoxy-propionic acid

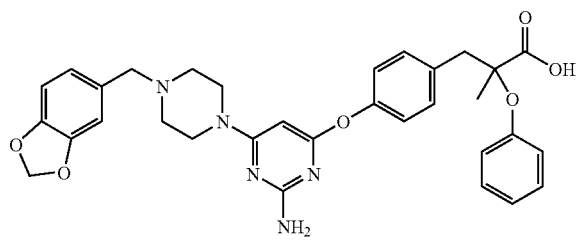 [SMILES: CC(Cc1ccc(Oc2cc(N3CCN(Cc4ccc5c(c4)OCO5)CC3)nc(N)n2)cc1)(Oc1ccccc1)C(=O)O]

This compound was prepared by means of a procedure similar to that used for Example 2.

mp 190-192° C.; $^1$HNMR (300 MHz, CD$_3$OD): δ 1.40 (s, 3H), 3.00 (t, 4H), 3.20 (m, 2H), 3.70 (t, 4H), 4.05 (s, 2H), 5.19 (s, 1H), 5.90 (d, 2H), 6.88~7.06 (m, 5H), 7.20~7.37 (m, 4H), 7.46~7.55 (m, 3H); EI-MS: m/e 583 (M$^+$), 135 (100%).

Example 6

3-{4-[2-Amino-6-(4-(naphthalen-1-ylmethyl)-piperazin-1-yl)-pyrimidin-4-yloxy]-phenyl}-2-methyl-2-phenoxy-propionic acid

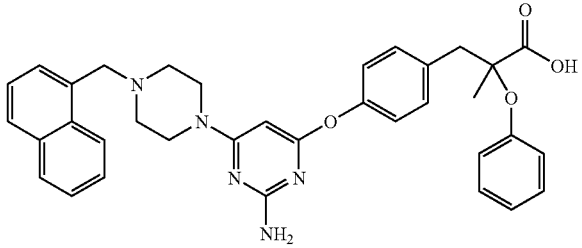 [SMILES: CC(Cc1ccc(Oc2cc(N3CCN(Cc4cccc5ccccc45)CC3)nc(N)n2)cc1)(Oc1ccccc1)C(=O)O]

This compound was prepared by means of a procedure similar to that used for Example 2.

mp 93-94° C.; $^1$HNMR (300 MHz, CD$_3$OD): δ 1.34 (s, 3H), 2.50 (t, 4H, J=5.1 Hz), 3.09 (d, 1H, J=13.5 Hz), 3.21 (d, 1H, J=13.5 Hz), 3.27 (t, 4H, J=5.1 Hz), 3.93 (s, 2H), 5.47 (s, 1H), 6.82 (d, 1H, J=8.1 Hz), 6.95~7.01 (m, 2H), 7.23~7.28 (m, 3H), 7.46~7.58 (m, 6H), 7.87~7.96 (m, 3H), 8.28 (d, 1H, J=7.5 Hz); EI-MS: m/e 589 (M$^+$), 141 (100%).

Example 7

3-{4-{2-Amino-6-[4-(4-fluoro-benzyl)-piperazin-1-yl]-pyrimidin-4-yloxy}-phenyl}-2-methyl-2-phenoxy-propionic acid

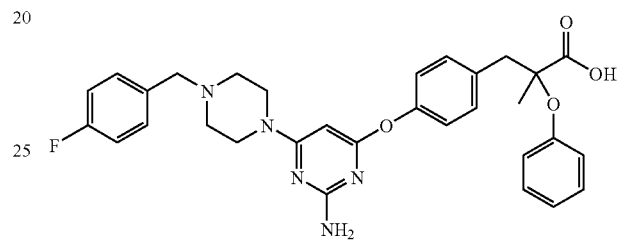

This compound was prepared by means of a procedure similar to that used for Example 2.

mp 107-109° C.; $^1$HNMR (300 MHz, CD$_3$OD): δ 1.40 (s, 3H), 2.58 (t, 4H), 3.15 (q, 2H), 3.53 (t, 4H), 3.65 (s, 2H), 5.15 (s, 1H), 6.9 (t, 3H), 7.00 (d, 2H), 7.18 (t, 2H), 7.35 (d, 2H), 7.60 (q, 4H).

EI-MS: m/e 557 (M$^+$), 94 (100%).

Example 8

3-{4-{2-Amino-6-[4-(4-trifluoromethyl-benzyl)-piperazin-1-yl]-pyrimidin-4-yloxy}-phenyl}-2-methyl-2-phenoxy-propionic acid

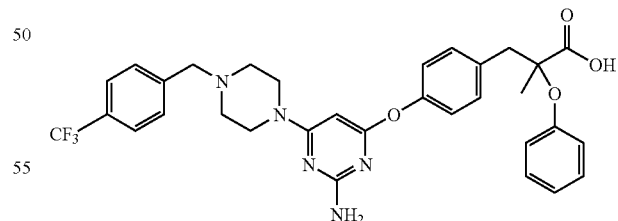

This compound was prepared by means of a procedure similar to that used for Example 2.

mp 114-115° C.; $^1$HNMR (300 MHz, CD$_3$OD): δ 1.38 (s, 3H), 2.50 (t, 4H, J=5.1 Hz), 3.17 (d, 1H, J=13.5 Hz), 3.35 (d, 1H, J=13.5 Hz), 3.53 (t, 4H, J=5.1 Hz), 3.65 (s, 2H), 5.25 (s, 1H), 6.9 (m, 3H), 7.00 (d, 2H, J=8.4 Hz), 7.18 (t, 2H, J=7.8

Hz), 7.35 (d, 2H, J=8.4 Hz), 7.58 (d, 2H, J=8.1 Hz), 7.62 (d, 2H, J=8.1 Hz); EI-MS: m/e 607 (M+), 94 (100%).

Example 9

3-{4-{2-Amino-6-[4-(3-methyl-benzyl)-piperazin-1-yl]-pyrimidin-4-yloxy}-phenyl}-2-methyl-2-phenoxy-propionic acid

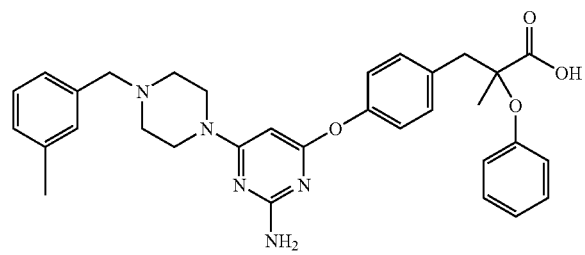 [SMILES: Cc1cccc(CN2CCN(c3cc(Oc4ccc(CC(C)(Oc5ccccc5)C(=O)O)cc4)nc(N)n3)CC2)c1]

This compound was prepared by means of a procedure similar to that used for Example 2.

mp 115-116° C.; $^1$HNMR (300 MHz, CD$_3$OD): δ 1.38 (s, 3H), 2.34 (s, 3H), 2.50 (t, 4H, J=5.1 Hz), 3.17 (d, 1H, J=13.5 Hz), 3.35 (d, 1H, J=13.5 Hz), 3.60 (t, 4H, J=5.1 Hz), 3.94 (s, 2H), 5.32 (s, 1H), 6.9 (m, 4H), 7.00 (d, 2H, J=8.4 Hz), 7.16~7.25 (m, 5H), 7.33 (d, 2H, J=8.4 Hz); EI-MS: m/e 553 (M+), 94 (100%).

Example 10

3-{4-{2-Amino-6-[4-(3-trifluoromethyl-benzyl)-piperazin-1-yl]-pyrimidin-4-yloxy}-phenyl}-2-methyl-2-phenoxy-propionic acid

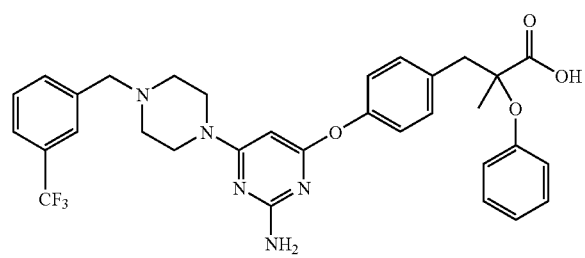 [SMILES: CC(Cc1ccc(Oc2cc(N3CCN(Cc4cccc(C(F)(F)F)c4)CC3)nc(N)n2)cc1)(Oc1ccccc1)C(=O)O]

This compound was prepared by means of a procedure similar to that used for Example 2.

mp 97-98° C.; $^1$HNMR (300 MHz, CD$_3$OD): δ 1.38 (s, 3H), 2.53 (t, 4H, J=5.1 Hz), 3.17 (d, 1H, J=13.5 Hz), 3.35 (d, 1H, J=13.5 Hz), 3.53 (t, 4H, J=5.1 Hz), 3.70 (s, 2H), 5.25 (s, 1H), 6.9 (m, 3H), 7.00 (d, 2H, J=8.4 Hz), 7.18 (t, 2H, J=7.8 Hz), 7.35 (d, 2H, J=8.4 Hz), 7.55~7.69 (m, 4H); EI-MS: m/e 607 (M+), 94 (100%).

Example 11

3-{4-{2-Amino-6-[4-(3-chloro-benzyl)-piperazin-1-yl]-pyrimidin-4-yloxy}-phenyl}-2-methyl-2-phenoxy-propionic acid

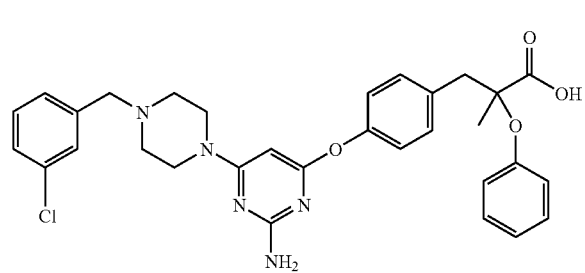 [SMILES: CC(Cc1ccc(Oc2cc(N3CCN(Cc4cccc(Cl)c4)CC3)nc(N)n2)cc1)(Oc1ccccc1)C(=O)O]

This compound was prepared by means of a procedure similar to that used for Example 2.

mp 87-89° C.; $^1$HNMR (300 MHz, d$_6$-DMSO): δ 1.30 (s, 3H), 2.50 (t, 4H, J=5.1 Hz), 3.13 (d, 1H, J=13.5 Hz), 3.22 (d, 1H, J=13.5 Hz), 3.18 (q, 2H, J=13.5 Hz), 3.63 (t, 4H, J=5.1 Hz), 4.41 (s, 2H), 5.46 (s, 1H), 6.83 (d, 2H, J=8.1 Hz), 6.90 (t, 1H, J=7.5 Hz), 6.96 (d, 2H, J=8.4 Hz), 7.19~7.38 (m, 8H); EI-MS: m/e 573 (M+), 94 (100%).

Example 12

3-{4-{2-Amino-6-[4-(3-fluoro-benzyl)-piperazin-1-yl]-pyrimidin-4-yloxy}-phenyl}-2-methyl-2-phenoxy-propionic acid

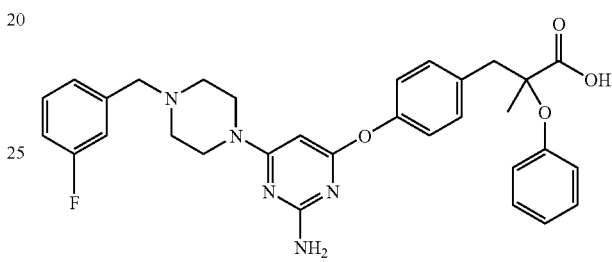

This compound was prepared by means of a procedure similar to that used for Example 2.

mp 113-115° C.; $^1$HNMR (300 MHz, CD$_3$OD): δ 1.40 (s, 3H), 2.58 (t, 4H), 3.15 (q, 2H), 3.53 (t, 4H), 3.65 (s, 2H), 5.15 (s, 1H), 6.92 (t, 3H), 7.00 (d, 2H), 7.18 (t, 2H), 7.35 (d, 2H), 7.60 (m, 4H).

EI-MS: m/e 557 (M+), 94 (100%).

Example 13

3-{4-{2-Amino-6-[4-(4-chloro-benzyl)-piperazin-1-yl]-pyrimidin-4-yloxy}-phenyl}-2-methyl-2-phenoxy-propionic acid

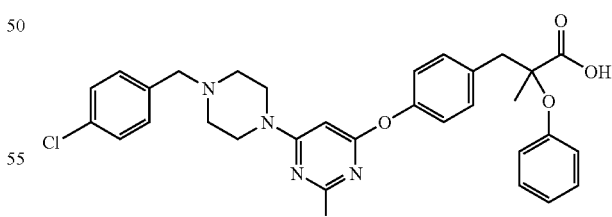

This compound was prepared by means of a procedure similar to that used for Example 2.

mp 103-105° C.; $^1$HNMR (400 MHz, CD$_3$OD): δ 1.40 (s, 3H), 2.95 (t, 4H, J=5.1 Hz), 3.20 (d, 1H, J=13.5 Hz), 3.38 (d, 1H, J=13.5 Hz), 3.70 (t, 4H, J=5.1 Hz), 4.05 (s, 2H), 5.38 (s, 1H), 6.82 (m, 1H), 6.93 (m, 2H), 7.03 (m, 2H), 7.18 (m, 2H), 7.27-7.38 (m, 6H); m/e 573 (M+), 94 (100%).

Example 14

3-{4-{2-Amino-6-[4-(4-tert-butyl-benzyl)-piperazin-1-yl]-pyrimidin-4-yloxy}-phenyl}-2-methyl-2-phenoxy-propionic acid

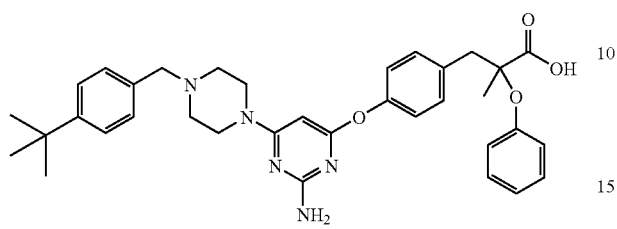

This compound was prepared by means of a procedure similar to that used for Example 2.

mp 96-97° C.; $^1$HNMR (300 MHz, d$_6$-DMSO): δ 1.26 (s, 9H), 1.33 (s, 3H), 2.36 (t, 4H, J=5.1 Hz), 3.18 (m, 2H), 3.26 (s, 2H), 3.44 (t, 4H, J=5.1 Hz), 5.45 (s, 1H), 6.83 (d, 2H, J=8.4 Hz), 6.93~6.99 (m, 3H), 7.21 (m, 5H), 7.35 (m, 3H); EI-MS: m/e 595 (M$^+$), 147 (100%).

Example 15

3-{4-{2-Amino-6-[4-(4-bromo-benzyl)-piperazin-1-yl]-pyrimidin-4-yloxy}-phenyl}-2-methyl-2-phenoxy-propionic acid

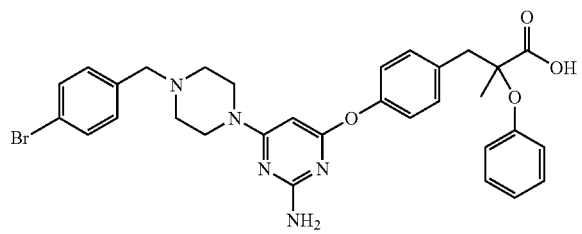 [SMILES: CC(Cc1ccc(Oc2cc(N3CCN(Cc4ccc(Br)cc4)CC3)nc(N)n2)cc1)(Oc1ccccc1)C(=O)O]

This compound was prepared by means of a procedure similar to that used for Example 2.

mp 112-114° C.; $^1$HNMR (300 MHz, CD$_3$OD): δ 1.40 (s, 3H), 2.84 (t, 4H, J=5.1 Hz), 3.17 (d, 1H, J=13.5 Hz), 3.35 (d, 1H, J=13.5 Hz), 3.63 (t, 4H, J=5.1 Hz), 3.91 (s, 2H), 5.38 (s, 1H), 6.90 (m, 3H), 7.01 (d, 2H, J=8.7 Hz), 7.22 (m, 2H), 7.36 (d, 2H, J=8.7 Hz), 7.58 (d, 2H, J=8.7 Hz), 7.62 (d, 2H, J=8.7 Hz); EI-MS: m/e 617 (M$^+$), 94 (100%).

Example 16

3-{4-{2-Amino-6-[4-(3-bromo-benzyl)-piperazin-1-yl]-pyrimidin-4-yloxy}-phenyl}-2-methyl-2-phenoxy-propionic acid

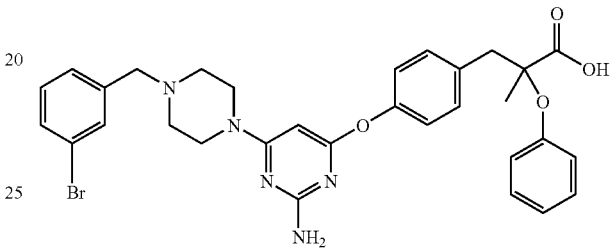

This compound was prepared by means of a procedure similar to that used for Example 2.

mp 119-120° C.; $^1$HNMR (300 MHz, d$_6$-DMSO): δ 1.40 (s, 3H), 3.25 (q, 2H, J=13.5 Hz), 3.53 (t, 4H, J=5.1 Hz), 3.63 (t, 4H, J=5.1 Hz), 5.52 (s, 1H), 6.69 (t, 1H, J=6.6 Hz), 6.80 (d, 1H, J=9.0 Hz), 6.90 (d, 2H, J=7.1 Hz), 6.96 (d, 1H, J=6.6 Hz), 7.04 (d, 1H, J=7.5 Hz), 7.23 (t, 2H, J=7.5 Hz), 7.36 (d, 2H, J=7.5 Hz), 7.57 (t, 1H, J=8.4 Hz), 8.07 (m, 1H); EI-MS: m/e 618 (M$^+$), 94 (100%).

Example 17

3-{4-{2-Amino-6-[4-(3-phenoxy-benzyl)-piperazin-1-yl]-pyrimidin-4-yloxy}-phenyl}-2-methyl-2-phenoxy-propionic acid

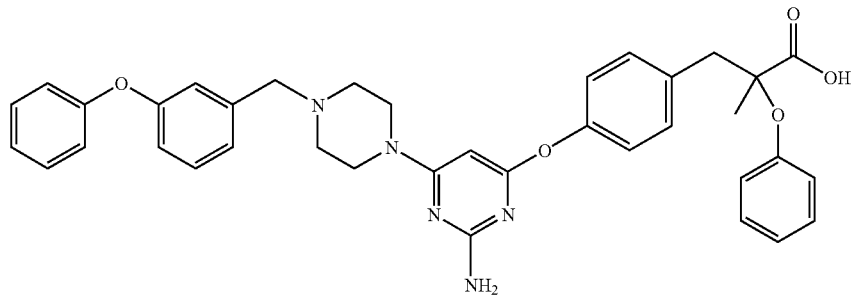 [SMILES: CC(Cc1ccc(Oc2cc(N3CCN(Cc4cccc(Oc5ccccc5)c4)CC3)nc(N)n2)cc1)(Oc1ccccc1)C(=O)O]

Example 18

3-{4-{2-Amino-6-[4-(2-oxo-2-phenyl-ethyl)-piperazin-1-yl]-pyrimidin-4-yloxy}-phenyl}-2-methyl-2-phenoxy-propionic acid

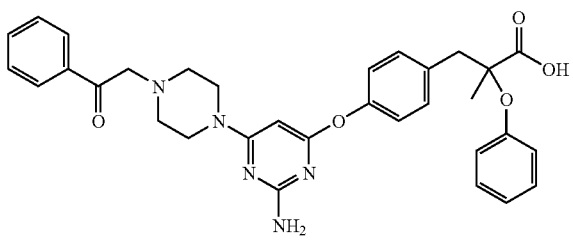 [SMILES: CC(Cc1ccc(Oc2cc(N3CCN(CC(=O)c4ccccc4)CC3)nc(N)n2)cc1)(Oc1ccccc1)C(=O)O]

This compound was prepared by means of a procedure similar to that used for Example 2.

Mp: 107-108° C.; $^1$HNMR (300 MHz, $d_6$-DMSO): δ 1.32 (s, 3H), 3.30~3.62 (m, 10H), 3.68 (s, 2H), 5.53 (s, 1H), 6.83~7.02 (m, 5H), 7.21~7.25 (m, 4H), 7.62 (d, 2H, J=7.2 Hz), 7.62 (t, 1H, J=7.5 Hz), 7.62 (d, 2H, J=8.4 Hz); EI-MS: m/e 567 (M$^+$)

Example 19

3-{4-[2-Amino-6-(4-pyridin-2-yl-piperazin-1-yl)-pyrimidin-4-yloxy]-phenyl}-2-methyl-2-phenoxy-propionic acid

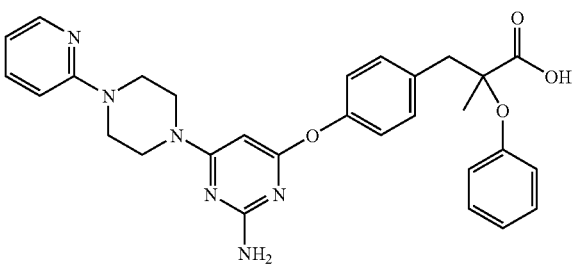 [SMILES: CC(Cc1ccc(Oc2cc(N3CCN(c4ncccn4)CC3)nc(N)n2)cc1)(Oc1ccccc1)C(=O)O]

This compound was prepared by means of a procedure similar to that used for Example 2.

mp 110-111° C.; $^1$HNMR (300 MHz, $d_6$-DMSO): δ 1.40 (s, 3H), 3.20 (d, 1H, J=13.5 Hz), 3.35 (d, 1H, J=13.5 Hz), 3.53 (t, 4H, J=5.1 Hz), 3.63 (t, 4H, J=5.1 Hz), 5.52 (s, 1H), 6.69 (t, 1H, J=6.6 Hz), 6.80 (d, 1H, J=9.0 Hz), 6.90 (d, 2H, J=7.1 Hz), 6.96 (d, 1H, J=6.6 Hz), 7.04 (d, 1H, J=7.5 Hz), 7.23 (t, 2H, J=7.5 Hz), 7.36 (d, 2H, J=7.5 Hz), 7.57 (t, 1H, J=8.4 Hz), 8.07 (m, 1H). EI-MS: m/e 526 (M$^+$), 94 (100%).

Example 20

3-{4-[2-Amino-6-(4-pyrimidin-2-yl-piperazin-1-yl)-pyrimidin-4-yloxy]-phenyl}-2-methyl-2-phenoxy-propionic acid

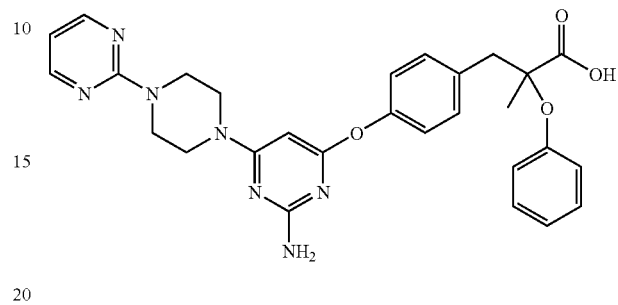

This compound was prepared by means of a procedure similar to that used for Example 2.

mp 136-137° C.; $^1$HNMR (300 MHz, $CD_3OD$): δ 1.40 (s, 3H), 3.10 (d, 1H, J=13.5 Hz), 3.38 (d, 1H, J=13.5 Hz), 3.25 (q, 2H, J=13.5 Hz), 3.60 (t, 4H, J=5.1 Hz), 3.81 (t, 4H, J=5.1 Hz), 5.35 (s, 1H), 6.60 (t, 1H, J=4.8 Hz), 6.90 (d, 2H, J=7.5 Hz), 6.96 (t, 1H, J=6.6 Hz), 7.04 (m, 2H), 7.24 (t, 2H, J=7.5 Hz), 7.36 (d, 2H, J=8.4 Hz), 8.33 (d, 2H, J=4.8 Hz); EI-MS: m/e 527 (M$^+$), 94 (100%).

Example 21

3-{4-[2-Amino-6-(4-benzoyl-piperazin-1-yl)-pyrimidin-4-yloxy]-phenyl}-2-methyl-2-phenoxy-propionic acid

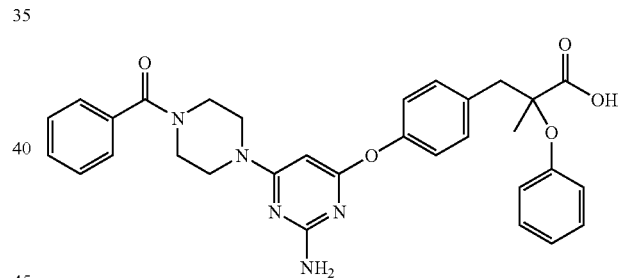

This compound was prepared by means of a procedure similar to that used for Example 2.
Mp:117-119° C.

Example 22

3-{4-[2-Amino-6-(4-phenyl-piperazin-1-yl)-pyrimidin-4-yloxy]-phenyl}-2-methyl-2-phenoxy-propionic acid

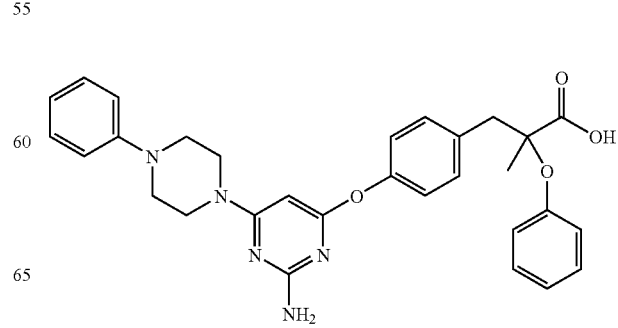

This compound was prepared by means of a procedure similar to that used for Example 2.

mp 150-151° C.; ¹HNMR (300 MHz, CD₃OD): δ 1.36 (s, 3H), 3.10~3.19 (m, 5H), 3.37 (d, 1H, J=13.5 Hz), 3.54 (t, 4H, J=5.1 Hz), 5.29 (s, 1H), 6.83 (t, 1H, J=7.2 Hz), 6.89~6.99 (m, 5H), 7.02 (d, 2H, J=8.7 Hz), 7.21 (q, 4H, J=7.8 Hz), 7.34 (d, 2H, J=8.1 Hz). EI-MS: m/e 525 (M⁺), 94 (100%).

Example 23

3-{4-{2-Amino-6-[4-(3-chloro-phenyl)-piperazin-1-yl]-pyrimidin-4-yloxy}-phenyl}-2-methyl-2-phenoxy-propionic acid

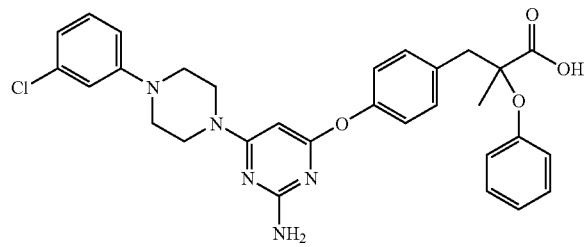 [SMILES: CC(Cc1ccc(Oc2cc(N3CCN(c4cccc(Cl)c4)CC3)nc(N)n2)cc1)(Oc1ccccc1)C(=O)O]

This compound was prepared by means of a procedure similar to that used for Example 2.

mp 212-214° C.; ¹HNMR (300 MHz, d₆-DMSO): δ 1.35 (s, 3H), 3.15 (d, 1H, J=13.5 Hz), 3.20~3.35 (m, 5H), 3.62 (t, 4H, J=5.1 Hz), 5.53 (s, 1H), 6.83~6.87 (m, 2H), 6.92 (m, 1H), 6.95~7.03 (m, 4H), 7.24~7.29 (m, 5H); EI-MS: m/e 559 (M⁺), 94 (100%).

Example 24

3-{4-{2-Amino-6-[4-(4-propyl-benzoyl)-piperazin-1-yl]-pyrimidin-4-yloxy}-phenyl}-2-methyl-2-phenoxy-propionic acid

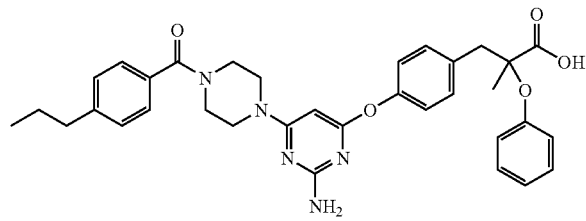 [SMILES: CCCc1ccc(C(=O)N2CCN(c3cc(Oc4ccc(CC(C)(Oc5ccccc5)C(=O)O)cc4)nc(N)n3)CC2)cc1]

This compound was prepared by means of a procedure similar to that used for Example 2.

Mp: 101-102° C.; ¹HNMR (300 MHz, d₆-DMSO): δ 0.88 (t, 3H, J=7.5 Hz), 1.33 (s, 3H), 1.60 (q, 2H, J=7.5 Hz), 2.59 (t, 2H, J=7.5 Hz), 3.17 (d, 1H, J=13.5 Hz), 3.35 (d, 1H, J=13.5 Hz), 3.48~3.55 (m, 8H), 5.50 (s, 1H), 6.83 (d, 2H, J=8.1 Hz), 6.96~7.00 (m, 3H), 7.23~7.36 (m, 7H), 7.35 (d, 1H, J=7.8 Hz); EI-MS: m/e 595 (M⁺), 94 (100%)

Example 25

3-{4-{2-Amino-6-[4-(2-methoxy-benzoyl)-piperazin-1-yl]-pyrimidin-4-yloxy}-phenyl}-2-methyl-2-phenoxy-propionic acid

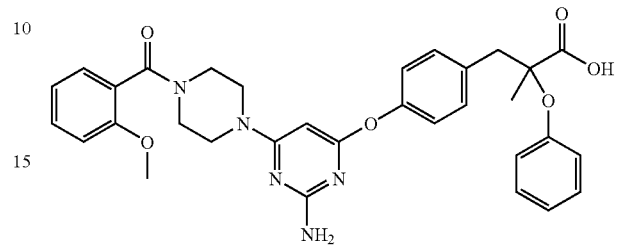

This compound was prepared by means of a procedure similar to that used for Example 2.

Mp: 108-109° C.; ¹HNMR (300 MHz, d₆-DMSO): δ 1.32 (s, 3H), 3.17 (d, 1H, J=13.5 Hz), 3.35 (d, 1H, J=13.5 Hz), 3.62 (m, 8H), 3.80 (s, 3H), 5.50 (s, 1H), 6.83 (d, 2H, J=7.8 Hz), 6.93~7.04 (m, 6H), 7.21~7.25 (m, 4H), 7.37 (m, 1H); EI-MS: m/e 583 (M⁺).

Example 26

3-{4-{2-Amino-6-[4-(3-cyano-benzyl)-piperazin-1-yl]-pyrimidin-4-yloxy}-phenyl}-2-methyl-2-phenoxy-propionic acid

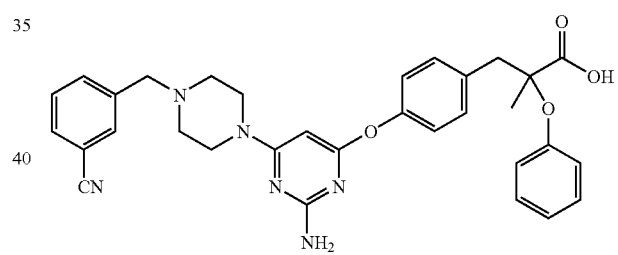

This compound was prepared by means of a procedure similar to that used for Example 2.

Mp: 171-172° C.; ¹HNMR (300 MHz, d₆-DMSO): δ 1.31 (s, 3H), 2.90 (t, 4H, J=5.1 Hz), 3.30 (m, 2H), 3.55 (t, 4H, J=5.1 Hz), 3.60 (s, 2H), 5.52 (s, 1H), 6.84~6.97 (m, 7H), 7.17~7.23 (m, 6H).

Example 27

3-{4-[2-Amino-6-(4-cyclohexylmethyl-piperazin-1-yl)-pyrimidin-4-yloxy]-phenyl}-2-methyl-2-phenoxy-propionic acid

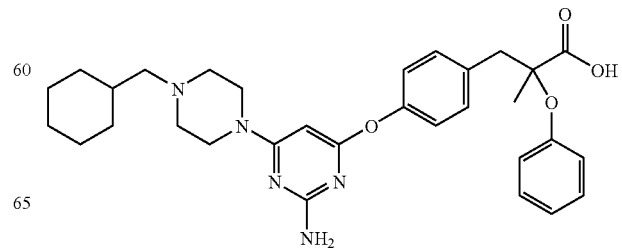

This compound was prepared by means of a procedure similar to that used for Example 2.

mp 180-182° C.; ¹HNMR (300 MHz, CD₃OD): δ 0.94 (m, 2H), 1.27~1.3 (m, 4H), 1.35 (s, 3H), 1.69~1.81 (m, 4H), 1.95 (s, 1H), 2.30 (d, 2H, J=6.9 Hz), 2.56 (t, 4H, J=6.0 Hz), 3.13 (d, 1H, J=13.8 Hz), 3.39 (d, 1H, J=13.8 Hz), 3.52 (t, 4H, J=6.0 Hz), 5.27 (s, 1H), 6.89~6.94 (m, 3H), 6.98 (d, 2H, J=8.7 Hz), 7.19 (t, 2H, J=7.2 Hz), 7.33 (d, 2H, J=8.7 Hz); EI-MS: m/e 545 (M⁺), 94 (100%).

Example 28

3-{4-[6-(4-benzyl-piperazin-1-yl)-pyrimidin-4-yloxy]-phenyl}-2-methyl-2-phenoxy-propionic acid

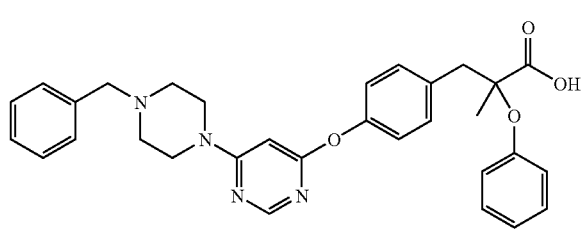 [SMILES: CC(Cc1ccc(Oc2cc(N3CCN(Cc4ccccc4)CC3)ncn2)cc1)(Oc1ccccc1)C(=O)O]

The title compound was the prepared using the procedure of Example 2 to provide a white solid.

mp 107-109° C.; ¹HNMR (300 MHz, CD₃OD): δ 1.38 (s, 3H), 2.71 (t, 4H, J=5.1 Hz), 3.17 (d, 1H, J=13.5 Hz), 3.35 (d, 1H, J=13.5 Hz), 3.64 (t, 4H, J=5.1 Hz), 3.78 (s, 2H), 5.99 (s, 1H), 6.80~6.91 (m, 3H), 7.01 (d, 2H, J=8.7 Hz), 7.18 (d, 2H, J=7.5 Hz), 7.34~7.37 (m, 7H), 8.15 (s, 1H); EI-MS: m/e 524 (M⁺), 159 (100%).

Example 29

3-{4-[2-Amino-6-(4-benzyl-piperazin-1-yl)-pyrimidin-4-yloxy]-phenyl}-2-(biphenyl-4-yloxy)-2-methyl-propionic acid

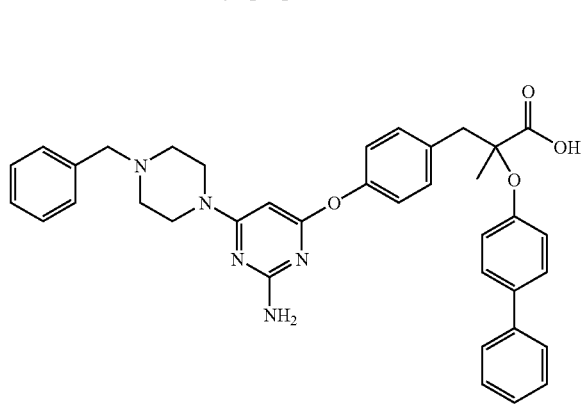 [SMILES: CC(Cc1ccc(Oc2cc(N3CCN(Cc4ccccc4)CC3)nc(N)n2)cc1)(Oc1ccc(-c2ccccc2)cc1)C(=O)O]

This compound was prepared by means of a procedure similar to that used for Example 2.

¹HNMR (300 MHz, CD₃OD): δ 1.38 (s, 3H), 2.47 (t, 4H, J=5.7 Hz), 3.15 (d, 1H, J=13.2 Hz), 3.40 (d, 1H, J=13.2 Hz), 3.50 (t, 4H, J=5.7 Hz), 3.57 (s, 2H), 5.25 (s, 1H), 6.97-7.12 (d, d, 4H, J=5.7, 3.0 Hz), 7.22~7.39 (m, 10H), 7.45 (d, 2H, J=15.0 Hz), 7.32 (d, 2H, J=6.3 Hz). EI-MS: m/e 615 (M⁺), 170 (100%).

Example 30

3-{4-[2-Amino-6-(4-benzyl-piperazin-1-yl)-pyrimidin-4-yloxy]-phenyl}-2-(4-methoxy-phenoxy)-2-methyl-propionic acid

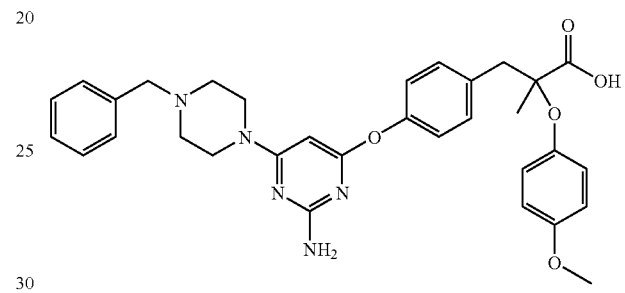

¹HNMR (300 MHz, CD₃OD): δ 1.30 (s, 3H), 2.51 (t, 4H, J=5.1 Hz), 3.15 (d, 1H, J=13.5 Hz), 3.40 (d, 1H, J=13.5 Hz), 3.50 (t, 4H, J=5.1 Hz), 3.60 (s, 2H), 3.70 (s, 3H), 5.31 (s, 1H), 6.74 (d, 2H, J=9.3 Hz), 6.87 (d, 2H, J=9.3 Hz), 6.99 (d, 2H, J=8.4 Hz), 7.29~7.37 (m, 7H). EI-MS: m/e 569 (M⁺), 124 (100%).

Example 31

3-{4-[2-Amino-6-(4-benzyl-piperazin-1-yl)-pyrimidin-4-yloxy]-phenyl}-2-methyl-2-p-tolyloxy-propionic acid

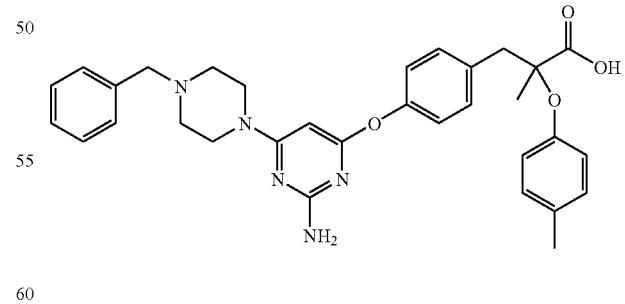

This compound was prepared by means of a procedure similar to that used for Example 2.

¹HNMR (300 MHz, CD₃OD): δ 1.33 (s, 3H), 2.23 (s, 3H), 2.71 (t, 4H, J=5.1 Hz), 3.15 (d, 1H, J=13.5 Hz), 3.40 (d, 1H, J=13.5 Hz), 3.56 (t, 4H, J=5.1 Hz), 3.80 (s, 2H), 3.70 (s, 3H), 5.29 (s, 1H), 6.74 (d, 2H, J=9.3 Hz), 6.87 (d, 2H, J=9.3 Hz), 6.99 (s, 2H, J=8.4 Hz), 7.29-7.37 (m, 7H). EI-MS: m/e 553 (M⁺), 107 (100%).

Example 32

3-{4-[2-Amino-6-(4-benzyl-piperazin-1-yl)-pyrimidin-4-yloxy]-phenyl}-2-methyl-2-(4-trifluoromethyl-phenoxy)-propionic acid

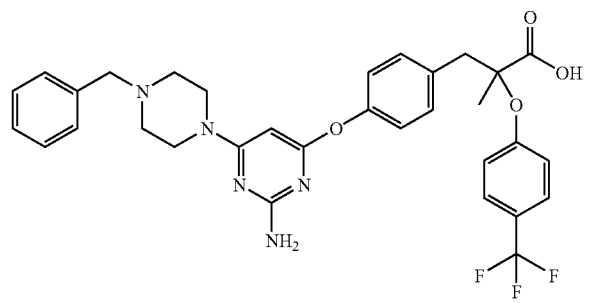 [SMILES: CC(Cc1ccc(Oc2cc(N3CCN(Cc4ccccc4)CC3)nc(N)n2)cc1)(Oc1ccc(C(F)(F)F)cc1)C(=O)O]

This compound was prepared by means of a procedure similar to that used for Example 2.

¹HNMR (300 MHz, CD₃OD): δ 1.47 (s, 3H), 2.64 (t, 4H, J=5.1 Hz), 3.15 (d, 1H, J=13.5 Hz), 3.55 (d, 1H, J=13.5 Hz), 3.50 (t, 4H, J=5.1 Hz), 3.60 (s, 2H), 3.70 (s, 3H), 5.31 (s, 1H), 6.93 (d, 2H, J=8.4 Hz), 7.03 (d, 2H, J=8.7 Hz), 7.29~7.37 (m, 7H), 7.47 (d, 2H, J=8.4 Hz). EI-MS: m/e 607 (M⁺), 161 (100%).

Example 33

3-{4-[6-(4-Benzyl-piperazin-1-yl)-2-phenyl-pyrimidin-4-yloxy]-phenyl}-2-methyl-2-phenoxy-propionic acid

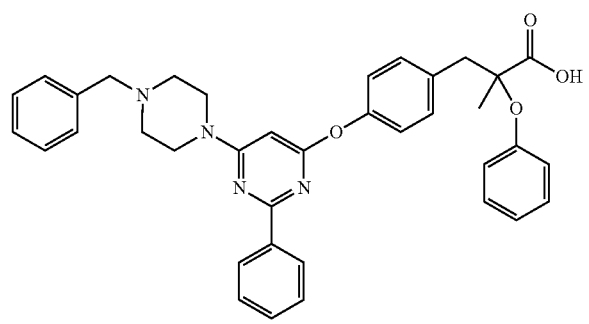 [SMILES: CC(Cc1ccc(Oc2cc(N3CCN(Cc4ccccc4)CC3)nc(-c3ccccc3)n2)cc1)(Oc1ccccc1)C(=O)O]

This compound was prepared by means of a procedure similar to that used for Example 2.

Example 34

3-{4-[6-(4-Benzyl-piperazin-1-yl)-2-methyl-pyrimidin-4-yloxy]-phenyl}-2-methyl-2-phenoxy-propionic acid

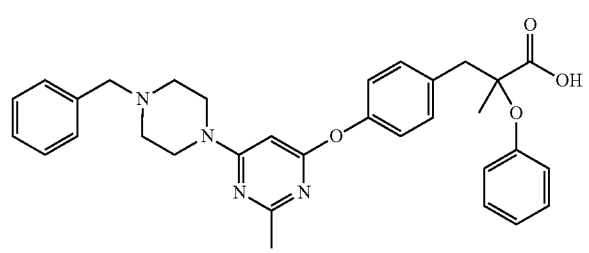 [SMILES: Cc1nc(Oc2ccc(CC(C)(Oc3ccccc3)C(=O)O)cc2)cc(N2CCN(Cc3ccccc3)CC2)n1]

This compound was prepared by means of a procedure similar to that used for Example 2.

Example 35

3-{4-[6-(4-Benzyl-piperazin-1-yl)-2-ethyl-pyrimidin-4-yloxy]-phenyl}-2-methyl-2-phenoxy-propionic acid

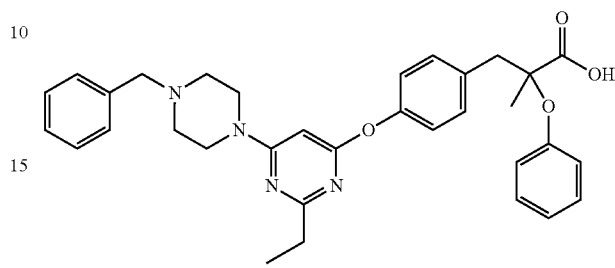

This compound was prepared by means of a procedure similar to that used for Example 2.

Example 36

3-{4-[2-Amino-6-(4-pyridin-2-ylmethyl-piperazin-1-yl)-pyrimidin-4-yloxy]-phenyl}-2-methyl-2-phenoxy-propionic acid

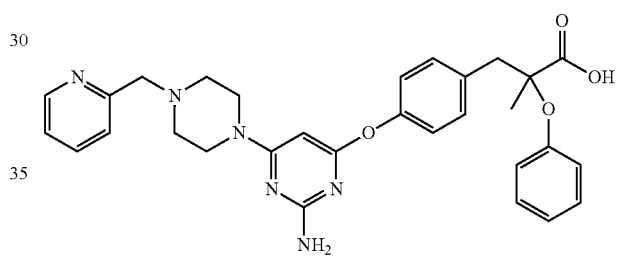

The tile compound, shown above, was made as described below.

Step A

3-[4-(2-Amino-6-piperazin-1-yl-pyrimidin-4-yloxy)-phenyl]-2-methyl-2-phenoxy-propionic acid ethyl ester

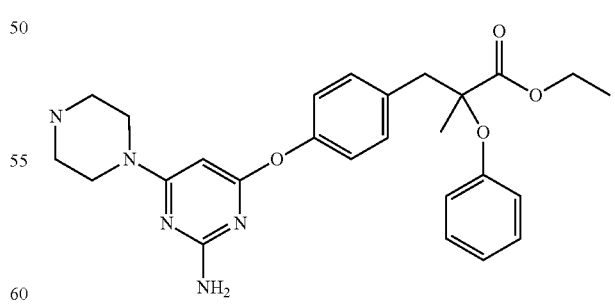

3-[4-(2-Amino-6-chloro-pyrimidin-4-yloxy)-phenyl]-2-methyl-2-phenoxy-propionic acid ethyl ester and piperazine were reacted, as described in Example 2, Step G, to provide 3-[4-(2-Amino-6-piperazin-1-yl-pyrimidin-4-yloxy)-phenyl]-2-methyl-2-phenoxy-propionic acid ethyl ester, shown below, as a yellow oil.

Step B

3-{4-[2-Amino-6-(4-pyridin-2-ylmethyl-piperazin-1-yl)-pyrimidin-4-yloxy]-phenyl}-2-methyl-2-phenoxy-propionic acid ethyl ester

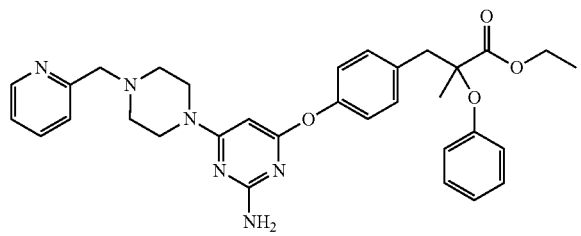 [SMILES: CCOC(=O)C(C)(Cc1ccc(Oc2cc(N3CCN(Cc4ccccn4)CC3)nc(N)n2)cc1)Oc1ccccc1]

To a stirring solution of 3-[4-(2-Amino-6-piperazin-1-yl-pyrimidin-4-yloxy)-phenyl]-2-methyl-2-phenoxy-propionic acid ethyl ester (1 mmol) in dry dichloromethane (20 ml) under $N_2$ was added pyridine-2-carbaldehyde (1.1 mmol). The reaction was stirred at room temperature for half an hour, then Sodium triacetoxyborohydride (1.3 mmol) was then added and stirred over night. Water (10 mL), the biphasic mixture was diluted with dichloromethane and partitioned, and the organic layer was washed with brine, dried over $MgSO_4$ and concentrated in vacuo. The residue was purified in silica to provide yellow solid.

$^1$HNMR (300 MHz, $CD_3OD$): δ1.15 (t, 3H, J=7.2 Hz), 1.38 (s, 3H), 2.53 (t, 4H, J=5.1 Hz), 3.15 (d, 1H, J=13.5 Hz), 3.37 (d, 1H, J=13.5 Hz), 3.51 (t, 4H, J=5.1 Hz), 3.56 (s, 2H), 4.12 (q, 2H, J=7.2 Hz), 5.17 (s, 1H), 6.63~6.89 (m, 3H), 6.95 (d, 2H, J=8.4 Hz), 7.14 (t, 2H, J=8.1 Hz), 7.29 (d, 2H, J=8.4 Hz), 7.32 (s, 1H), 7.49 (d, 1H, J=8.1 Hz), 7.79 (t, d, J=8.1, 1.5 Hz), 8.46 (d, 1H, J=4.8 Hz).

Step C

3-{4-[2-Amino-6-(4-pyridin-2-ylmethyl-piperazin-1-yl)-pyrimidin-4-yloxy]-phenyl}-2-methyl-2-phenoxy-propionic acid

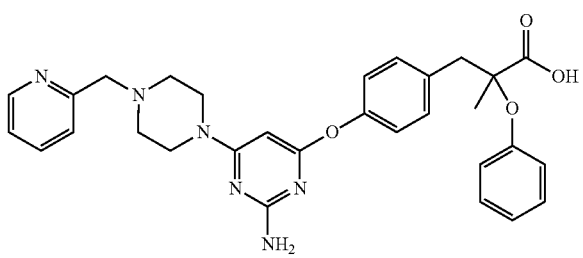 [SMILES: CC(Cc1ccc(Oc2cc(N3CCN(Cc4ccccn4)CC3)nc(N)n2)cc1)(Oc1ccccc1)C(=O)O]

The title compound was the prepared using the hydrolysis procedure of Example 2, Step H, to provide a white solid.

mp 138-139° C.; $^1$HNMR (300 MHz, $CD_3OD$): δ 1.38 (s, 3H), 2.61 (t, 4H, J=5.1 Hz), 3.15 (d, 1H, J=13.5 Hz), 3.37 (d, 1H, J=13.5 Hz), 3.56 (t, 4H, J=5.1 Hz), 3.71 (s, 2H), 5.22 (s, 1H), 6.68~6.94 (m, 3H), 7.00 (d, 2H, J=8.4 Hz), 7.19 (t, 2H, J=8.1 Hz), 7.34 (d, 2H, J=8.4 Hz), 7.37 (s, 1H), 7.54 (d, 1H, J=8.1 Hz), 7.84 (t, d, J=8.1 Hz, J=1.5 Hz), 8.51 (d, 1H, J=4.8 Hz). EI-MS: m/e 540 (M$^+$), 94 (100%).

Example 37

3-{4-[2-Amino-6-(4-furan-2-ylmethyl-piperazin-1-yl)-pyrimidin-4-yloxy]phenyl}-2-methyl-2-phenoxy-propionic acid

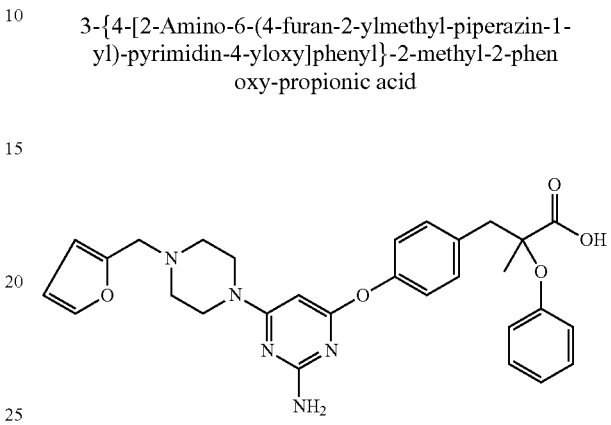

This compound was prepared by means of a procedure similar to that used for Example 36.

mp 142-143° C.; $^1$HNMR (300 MHz, $CD_3OD$): δ 1.38 (s, 3H), 2.59 (t, 4H, J=5.1 Hz), 3.14 (d, 1H, J=13.8 Hz), 3.37 (d, 1H, J=13.8 Hz), 3.54 (t, 4H, J=5.1 Hz), 3.71 (s, 2H), 5.26 (s, 1H), 6.38 (d, 2H, J=6.3 Hz), 6.78 (t, 2H, J=5.7 Hz), 6.96 (s, 1H), 7.02 (d, 2H, J=8.7 Hz), 7.21 (t, 3H, J=6.3 Hz), 7.33 (d, 2H, J=8.7 Hz), 7.49 (s, 1H). EI-MS: m/e 529 (M$^+$), 94 (100%).

Example 38

3-{4-{2-Amino-6-[4-(4-nitro-benzyl)-piperazin-1-yl]-pyrimidin-4-yloxy}-phenyl}-2-methyl-2-phenoxy-propionic acid

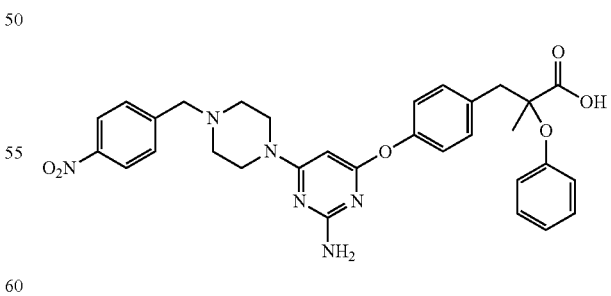

This compound was prepared by means of a procedure similar to that used for Example 36.

mp: 160-162° C.; $^1$HNMR (300 MHz, $d_6$-DMSO): δ 1.36 (s, 3H), 2.39 (t, 4H, J=5.1 Hz), 3.13 (d, 1H, J=13.5 Hz), 3.39 (d, 1H, J=13.5 Hz), 3.56 (t, 4H, J=5.1 Hz), 3.62 (s, 2H), 5.46 (s, 1H), 6.77 (d, 2H, J=7.8 Hz), 6.99 (d, 2H, J=7.8 Hz), 6.78

(t, 2H, J=8.4 Hz), 7.20~7.28 (m, 5H), 7.60 (d, 2H, J=8.4 Hz), 8.18 (d, 2H, J=8.4 Hz); EI-MS: m/e 584 (M+).

Example 39

3-{4-[2-Amino-6-(4-pyridin-3-ylmethyl-piperazin-1-yl)-pyrimidin-4-yloxy]-phenyl}-2-methyl-2-phenoxy-propionic acid

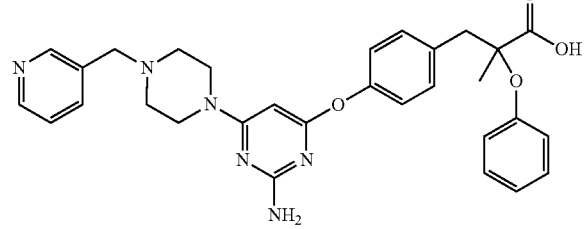

This compound was prepared by means of a procedure similar to that used for Example 36.

Mp: 141-143° C.; $^1$HNMR (300 MHz, CD$_3$OD): δ 1.39 (s, 3H), 2.46 (t, 4H, J=5.1 Hz), 3.17 (d, 1H, J=13.5 Hz), 3.35 (d, 1H, J=13.5 Hz), 3.50 (t, 4H, J=5.1 Hz), 3.65 (s, 2H), 5.22 (s, 1H), 6.87~6.94 (m, 3H), 7.01 (d, 2H, J=11.1 Hz), 7.20 (t, 2H, J=8.4 Hz), 7.32 (d, 2H, J=11.1 Hz), 7.42 (m, 1H), 7.87 (m, 1H), 8.51 (m, 2H); EI-MS: m/e 540 (M+).

Example 40

3-{4-[2-Amino-6-(4-pyridin-4-ylmethyl-piperazin-1-yl)-pyrimidin-4-yloxy]-phenyl}-2-methyl-2-phenoxy-propionic acid

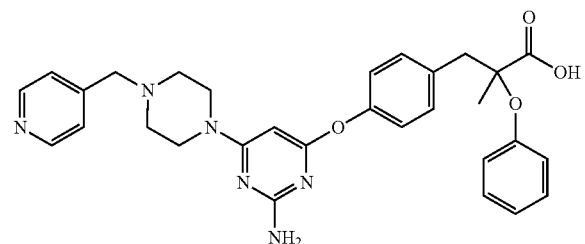 [SMILES: CC(Cc1ccc(Oc2cc(N3CCN(Cc4cccnc4)CC3)nc(N)n2)cc1)(Oc1ccccc1)C(=O)O]

This compound was prepared by means of a procedure similar to that used for Example 36.

Mp: 137-138° C.; $^1$HNMR (300 MHz, CD$_3$OD): δ 1.39 (s, 3H), 2.48 (t, 4H, J=5.7 Hz), 3.20 (d, 1H, J=13.5 Hz), 3.38 (d, 1H, J=13.5 Hz), 3.52 (t, 4H, J=5.7 Hz), 3.62 (s, 2H), 5.25 (s, 1H), 6.86~6.95 (m, 3H), 7.02 (d, 2H, J=8.7 Hz), 7.20 (t, 2H, J=6.3 Hz), 7.34 (d, 2H, J=8.7 Hz), 7.46 (d, 2H, J=6.0 Hz), 8.48 (d, 2H, J=6.0 Hz); EI-MS: m/e 540 (M+).

Example 41

3-{4-{2-Amino-6-[4-(2-iodo-benzyl)-piperazin-1-yl]-pyrimidin-4-yloxy}-phenyl}-2-methyl-2-phenoxy-propionic acid

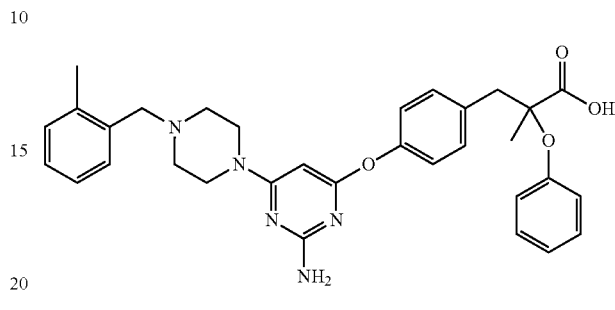

This compound was prepared by means of a procedure similar to that used for Example 36.

Example 42

3-{4-{2-Amino-6-[4-(2-methoxy-benzyl)-piperazin-1-yl]-pyrimidin-4-yloxy}-phenyl}-2-methyl-2-phenoxy-propionic acid

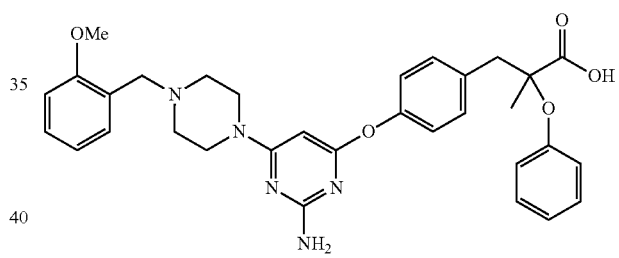

This compound was prepared by means of a procedure similar to that used for Example 36.

Example 43

3-{4-[6-(4-Benzyl-piperazin-1-yl)-2-phenoxy-pyrimidin-4-yloxy]-phenyl}-2-methyl-2-phenoxy-propionic acid

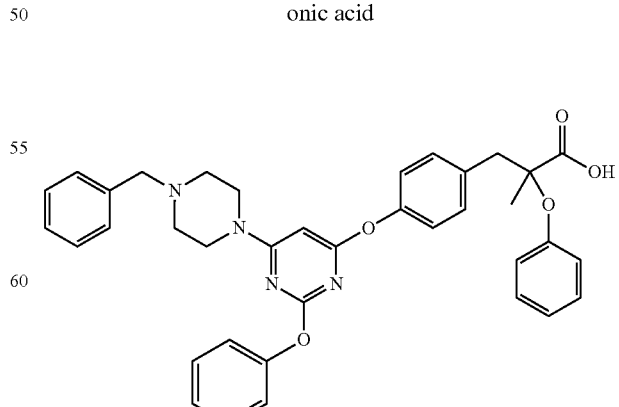

The title compound, shown above, was made as described below.

Step A 4,6-Dichloro-2-phenoxy-pyrimidine

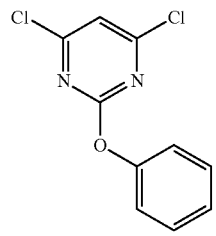 [SMILES: Clc1cc(Cl)nc(Oc2ccccc2)n1]

Phenol (0.94 g, 10 mmol) and sodium hydroxide (0.44 g, 11 mmol) in water (20 ml) were added to 2,4,6-trichloropyrimidine (1.83 g, 10 mmol) in acetone (20 ml) at 0° C. The mixture was stirred over night. The precipitate then filtered through celite, then the most of the acetone was removed in vacuo. The resulting aqueous solution was extracted with ethyl acetate, dried over sodium sulfate, and concentrated in vacuo. The residue was purified in silica to provide a colorless oil.

Step B 4-(4-Benzyl-piperazin-1-yl)-6-chloro-2-phenoxy-pyrimidine

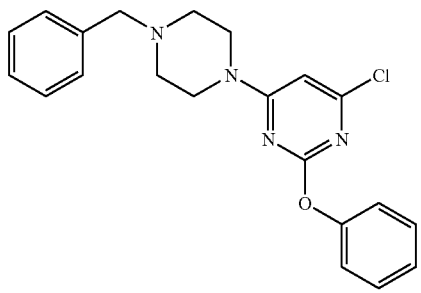 [SMILES: Clc1cc(N2CCN(Cc3ccccc3)CC2)nc(Oc2ccccc2)n1]

The title compound was the prepared using the hydrolysis procedure of Example 2, Step F, to provide a white solid.
$^1$HNMR (300 MHz, CDCl$_3$): δ 2.48 (t, 4H, J=8.1 Hz), 3.53~3.58 (m, 6H), 5.67 (s, 1H), 7.10~7.39 (m, 10H).

Step C

3-{4-[6-(4-Benzyl-piperazin-1-yl)-2-phenoxy-pyrimidin-4-yloxy]-phenyl}-2-methyl-2-phenoxy-propionic acid ethyl ester

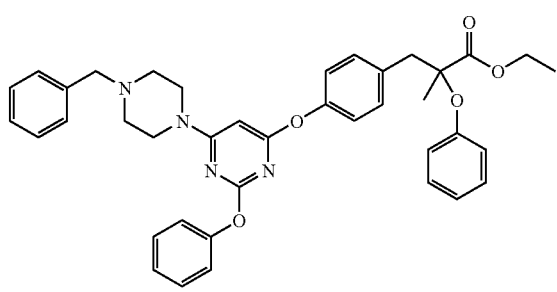 [SMILES: CCOC(=O)C(C)(Cc1ccc(Oc2cc(N3CCN(Cc4ccccc4)CC3)nc(Oc3ccccc3)n2)cc1)Oc1ccccc1]

The title compound was the prepared using the hydrolysis procedure of Example 2, Step F, to provide a white solid.
$^1$HNMR (300 MHz, d$_6$-DMSO): δ 1.10 (t, 3H, J=7.2 Hz), 1.33 (s, 3H), 2.23 (t, 4H, J=5.1 Hz), 3.13 (d, 1H, J=13.8 Hz), 3.39 (d, 1H, J=13.8 Hz), 3.17 (q, 2H, J=13.5 Hz), 3.40 (t, 4H, J=5.1 Hz), 3.42 (s, 2H), 4.10 (q, 2H, J=7.2 Hz), 5.36 (s, 1H), 6.73 (d, 2H, J=7.8 Hz), 6.92 (m, 1H), 7.07 (d, 2H), 7.14 (d, 2H, J=7.8 Hz), 7.18~7.30 (m, 9H), 7.39 (t, 3H, J=7.8 Hz).

Step D

3-{4-[6-(4-Benzyl-piperazin-1-yl)-2-phenoxy-pyrimidin-4-yloxy]-phenyl}-2-methyl-2-phenoxy-propionic acid

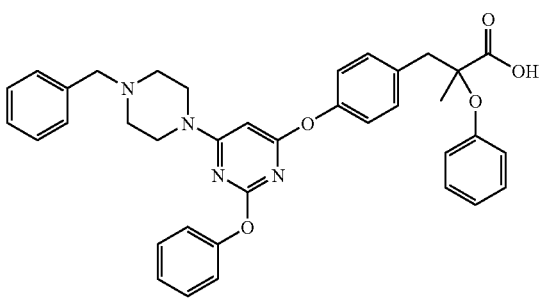 [SMILES: CC(Cc1ccc(Oc2cc(N3CCN(Cc4ccccc4)CC3)nc(Oc3ccccc3)n2)cc1)(Oc1ccccc1)C(=O)O]

The title compound was the prepared using the hydrolysis procedure of Example 2, Step H, to provide a white solid.
Mp: 126-128° C.; $^1$HNMR (300 MHz, CD$_3$OD): δ 1.35 (s, 3H), 2.94 (t, 4H, J=5.1 Hz), 3.20 (d, 1H, J=13.5 Hz), 3.35 (d, 1H, J=13.5 Hz), 3.67 (t, 4H, J=5.1 Hz), 4.01 (s, 2H), 5.54 (s, 1H), 6.87 (d, 2H, J=8.7 Hz), 6.94 (t, 1H, J=7.2 Hz), 7.01 (d, 2H, J=7.2 Hz), 7.11 (d, 2H, J=8.1 Hz), 7.21 (t, 3H, J=7.5 Hz), 7.31~7.38 (m, 4H), 7.40 (s, 5H); EI-MS: m/e 616 (M$^+$).

Example 44

3-{4-[2-(4-Benzyl-piperazin-1-yl)-6-phenoxy-pyrimidin-4-yloxy]-phenyl}-2-methyl-2-phenoxy-propionic acid

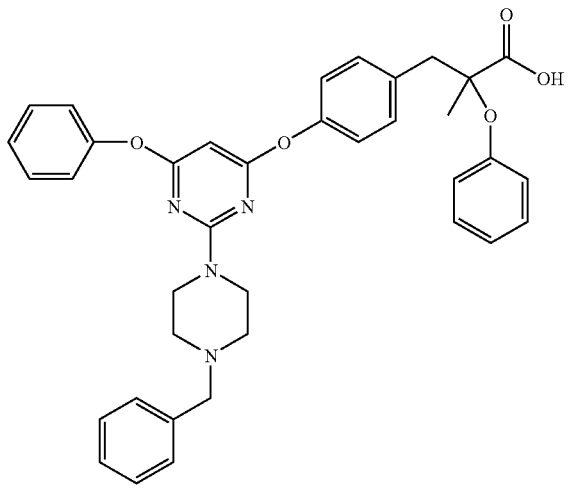 [SMILES: CC(Cc1ccc(Oc2cc(Oc3ccccc3)nc(N3CCN(Cc4ccccc4)CC3)n2)cc1)(Oc1ccccc1)C(=O)O]

The title compound was the prepared using the procedure of Example 43 to provide a white solid.
mp: 135-137° C.; $^1$HNMR (300 MHz, CD$_3$OD): δ 1.30 (s, 3H), 2.54 (t, 4H, J=5.1 Hz), 3.18 (q, 2H, J=13.5 Hz), 3.44 (t, 4H, J=5.1 Hz), 3.65 (s, 2H), 5.69 (s, 1H), 6.85-6.91 (m, 3H), 7.01 (d, 2H, J=7.8 Hz), 7.10 (d, 2H, J=9.0 Hz), 7.18 (t, 3H, J=8.1 Hz), 7.23-7.41 (m, 9H); EI-MS: m/e 616 (M$^+$).

Example 45

3-{4-[6-(4-Benzyl-piperazin-1-yl)-2-methoxy-pyrimidin-4-yloxy]-phenyl}-2-methyl-2-phenoxy-propionic acid

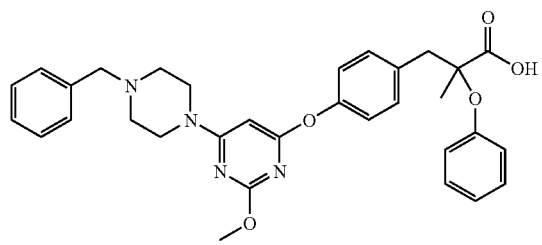 [SMILES: COc1nc(Oc2ccc(CC(C)(Oc3ccccc3)C(=O)O)cc2)cc(N2CCN(Cc3ccccc3)CC2)n1]

The title compound was the prepared using the procedure of Example 43 to provide a white solid.

Example 46

3-{4-[6-(4-Benzyl-piperazin-1-yl)-2-ethoxy-pyrimidin-4-yloxy]-phenyl}-2-methyl-2-phenoxy-propionic acid

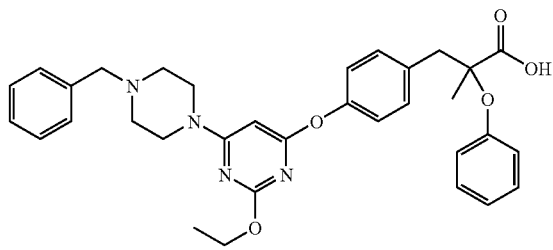 [SMILES: CCOc1nc(Oc2ccc(CC(C)(Oc3ccccc3)C(=O)O)cc2)cc(N2CCN(Cc3ccccc3)CC2)n1]

The title compound was the prepared using the procedure of Example 43 to provide a white solid.

Example 47

3-{4-[2-Benzylamino-6-(4-benzyl-piperazin-1-yl)-pyrimidin-4-yloxy]-phenyl}-2-methyl-2-phenoxy-propionic acid

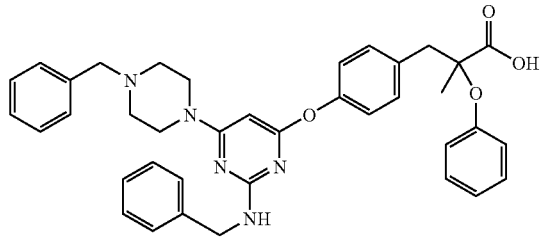 [SMILES: CC(Cc1ccc(Oc2cc(N3CCN(Cc4ccccc4)CC3)nc(NCc3ccccc3)n2)cc1)(Oc1ccccc1)C(=O)O]

The tile compound, shown above, was made as described below.

Step A

Benzyl-(4,6-dichloro-pyrimidin-2-yl)-amine

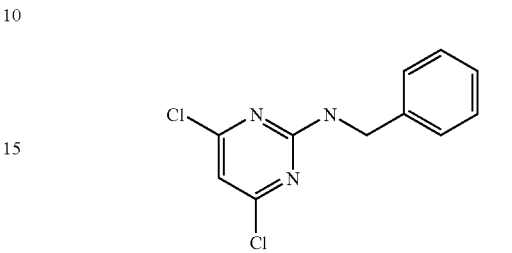

Benzylamine (0.53 g, 0.54 ml, 5 mmol) and triethylamine (0.50 g, 0.69 ml, 5 mmol) in tetrahydrofuran (20 ml) were added to 2,4,6-trichloropyrimidine (0.917 g, 5 mmol) in tetrahydrofuran (20 ml) at 0° C. The mixture was stirred for several hours. The precipitate then filtered through celite, then the most of the methanol was removed in vacuo. The residue was purified in silica to provide a colorless oil.

$^1$HNMR (300 MHz, CDCl$_3$): δ 4.63 (d, 2H, J=5.7 Hz), 6.64 (s, 1H), 7.27~7.39 (m, 5H).

Step B

3-[4-(2-Benzylamino-6-chloro-pyrimidin-4-yloxy)-phenyl]-2-methyl-2-phenoxy-propionic acid ethyl ester

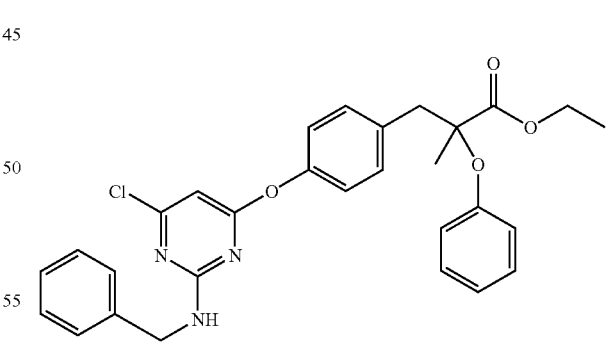

3-(4-Hydroxyphenyl)-2-methyl-2-phenoxypropionic acid ethyl ester (60 mg, 0.2 mmol), benzyl-(4,6-dichloro-pyrimidin-2-yl)-amine (50 mg, 0.2 mmol) and Cs$_2$CO$_3$ (76 mg, 0.22 mmol) were combined in anhydrous N,N-dimethylformamide (DMF) (5 mL) and stirred at 90° C. in dry atmosphere for 5 h. The DMF was removed in vacuo, the residue was purified in silica to provide a white oil.

Step C

3-{4-[2-Benzylamino-6-(4-benzyl-piperazin-1-yl)-pyrimidin-4-yloxy]-phenyl}-2-methyl-2-phenoxy-propionic acid ethyl ester

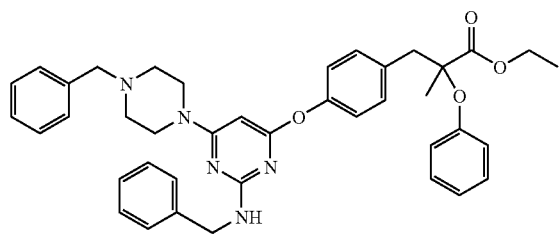 [SMILES: CCOC(=O)C(C)(Cc1ccc(Oc2cc(N3CCN(Cc4ccccc4)CC3)nc(NCc3ccccc3)n2)cc1)Oc1ccccc1]

3-[4-(2-Benzylamino-6-chloro-pyrimidin-4-yloxy)-phenyl]-2-methyl-2-phenoxy-propionic acid ethyl ester (60 mg, 0.1 mmol), 1-Benzyl-piperazine (25 mg, 0.25 ml, 0.15 mmol) and $Cs_2CO_3$ (35 mg, 0.11 mmol) were combined in anhydrous N,N-dimethylformamide (DMF) (5 mL) and stirred at 90° C. in dry atmosphere overnight. The DMF was removed in vacuo, the residue was purified in silica to provide a white oil.

Step D

3-{4-[2-Benzylamino-6-(4-benzyl-piperazin-1-yl)-pyrimidin-4-yloxy]-phenyl}-2-methyl-2-phenoxy-propionic acid

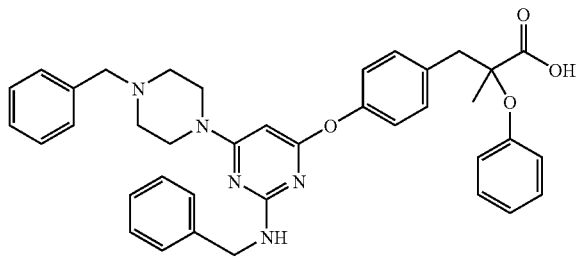 [SMILES: CC(Cc1ccc(Oc2cc(N3CCN(Cc4ccccc4)CC3)nc(NCc3ccccc3)n2)cc1)(Oc1ccccc1)C(=O)O]

The title compound was the prepared using the hydrolysis procedure of Example 2, Step H, to provide a white solid.

mp 104-106° C.; $^1$HNMR (300 MHz, $CD_3OD$): δ 1.36 (s, 3H), 2.73 (t, 4H, J=4.8 Hz), 3.17 (d, 1H, J=13.5 Hz), 3.35 (d, 1H, J=13.5 Hz), 3.36~3.50 (m, 6H), 4.41 (s, 2H), 5.24 (s, 1H), 6.88~7.04 (m, 5H), 7.16~7.32 (m, 9H), 7.38~7.41 (m, 5H), EI-MS: m/e 629 ($M^+$), 94 (100%).

Example 48

3-{4-[6-(4-Benzyl-piperazin-1-yl)-2-methylamino-pyrimidin-4-yloxy]-phenyl}-2-methyl-2-phenoxy-propionic acid

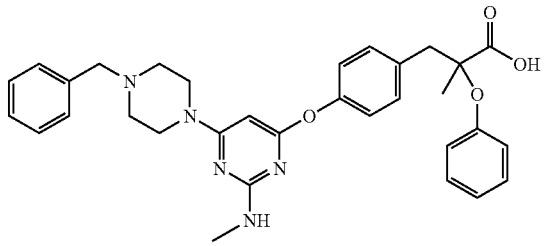 [SMILES: CNc1nc(Oc2ccc(CC(C)(Oc3ccccc3)C(=O)O)cc2)cc(N2CCN(Cc3ccccc3)CC2)n1]

This compound was prepared by means of a procedure similar to that used for Example 47.

Example 49

3-{4-[6-(4-Benzyl-piperazin-1-yl)-2-dimethylamino-pyrimidin-4-yloxy]-phenyl}-2-methyl-2-phenoxy-propionic acid

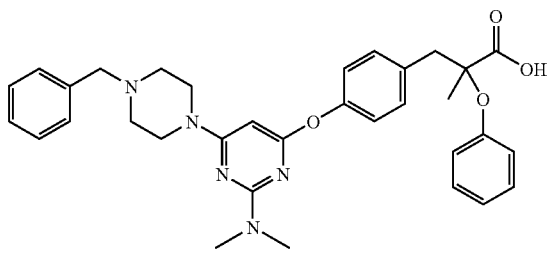 [SMILES: CN(C)c1nc(Oc2ccc(CC(C)(Oc3ccccc3)C(=O)O)cc2)cc(N2CCN(Cc3ccccc3)CC2)n1]

This compound was prepared by means of a procedure similar to that used for Example 47.

mp 136-138° C.; $^1$HNMR (300 MHz, $CD_3OD$): δ 1.37 (s, 3H), 2.82 (t, 4H, J=5.7 Hz), 3.00 (s, 6H), 3.19 (d, 1H, J=13.5 Hz), 3.32 (d, 1H, J=13.5 Hz), 3.61 (t, 4H, J=5.7 Hz), 3.93 (s, 2H), 5.11 (s, 1H), 6.87~6.92 (m, 3H), 7.01 (d, 2H, J=8.1 Hz), 7.20 (t, 2H, J=8.1 Hz), 7.31 (d, 2H, J=8.7 Hz), 7.37~7.43 (m, 5H), EI-MS: m/e 567 ($M^+$), 107 (100%).

Example 50

3-{4-[6-(4-Benzyl-piperazin-1-yl)-2-ethylamino-pyrimidin-4-yloxy]-phenyl}-2-methyl-2-phenoxy-propionic acid

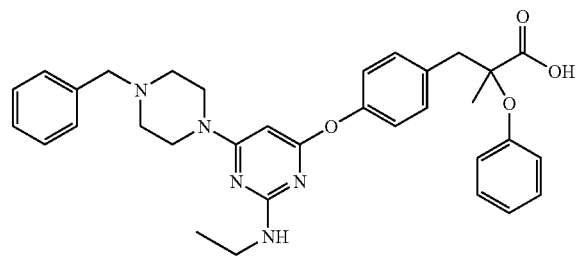

This compound was prepared by means of a procedure similar to that used for Example 47.

mp 106-107° C.; $^1$HNMR (300 MHz, $CD_3OD$): δ 1.09 (t, 3H, J=7.2 Hz), 1.40 (s, 3H), 3.00 (t, 4H, J=5.7 Hz), 3.13 (d, 1H, J=13.5 Hz), 3.30~3.35 (m, 3H), 3.72 (t, 4H, J=5.7 Hz), 4.01 (s, 1H), 5.18 (s, 1H), 6.82~6.96 (m, 3H), 7.02 (d, 2H, J=8.7 Hz), 7.21 (t, 2H, J=8.7 Hz), 7.31 (d, 2H, J=8.4 Hz), 7.18~7.23 (m, 5H), EI-MS: m/e 567 ($M^+$), 107 (100%).

Example 51

3-{4-[6-(4-Benzyl-piperazin-1-yl)-2-diethylamino-pyrimidin-4-yloxy]-phenyl}-2-methyl-2-phenoxy-propionic acid

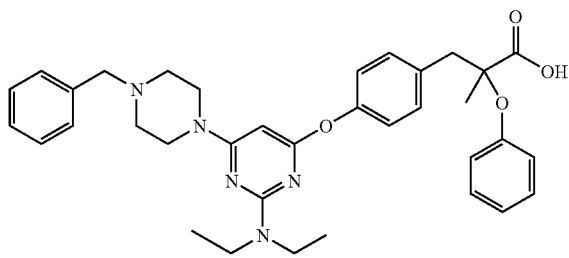 [SMILES: CCN(CC)c1nc(Oc2ccc(CC(C)(Oc3ccccc3)C(=O)O)cc2)cc(N2CCN(Cc3ccccc3)CC2)n1]

This compound was prepared by means of a procedure similar to that used for Example 47.

mp 120-121° C.; ¹HNMR (300 MHz, CD₃OD): δ 1.03 (t, 6H, J=7.2 Hz), 1.35 (s, 3H), 2.82 (t, 4H, J=5.7 Hz), 3.17 (d, 1H, J=13.5 Hz), 3.32 (d, 1H, J=13.5 Hz), 3.42 (d, 4H, J=7.2 Hz), 3.61 (t, 4H, J=5.7 Hz), 3.88 (s, 2H), 5.13 (s, 1H), 6.88~6.94 (m, 3H), 6.96 (d, 2H, J=8.4 Hz), 7.19 (t, 2H, J=8.1 Hz), 7.30 (d, 2H, J=8.7 Hz), 7.36~7.41 (m, 5H); EI-MS: m/e 595 (M⁺), 94 (100%).

Example 52

3-{4-[6-(4-Benzyl-piperazin-1-yl)-2-piperidin-1-yl-pyrimidin-4-yloxy]-phenyl}-2-methyl-2-phenoxy-propionic acid

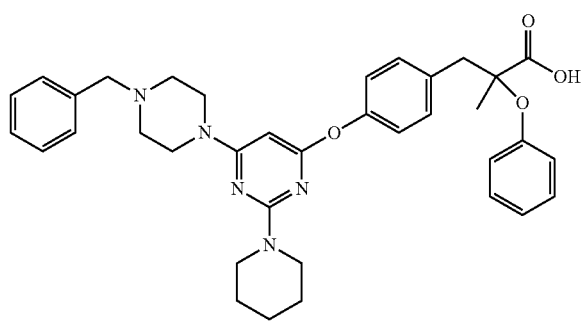 [SMILES: CC(Cc1ccc(Oc2cc(N3CCN(Cc4ccccc4)CC3)nc(N3CCCCC3)n2)cc1)(Oc1ccccc1)C(=O)O]

This compound was prepared by means of a procedure similar to that used for Example 47.

mp 125-126° C.; ¹HNMR (300 MHz, CD₃OD): δ 1.32 (s, 3H), 1.47 (m, 4H), 1.61 (m, 2H), 2.60 (t, 4H J=5.7 Hz), 3.15 (d, 1H, J=13.5 Hz), 3.33 (d, 1H, J=13.5 Hz), 3.54 (m, 4H), 3.59 (m, 4H), 3.70 (s, 2H), 5.11 (s, 1H), 6.88-6.91 (m, 3H), 6.98 (d, 2H, J=7.8 Hz), 7.17 (t, 2H, J=7.5 Hz), 7.31 (d, 2H, J=8.4 Hz), 7.35~7.48 (m, 5H); EI-MS: m/e 607 (M⁺), 94 (100%).

Example 53

3-{4-[6-(4-Benzyl-piperazin-1-yl)-2-morpholin-4-yl-pyrimidin-4-yloxy]-phenyl}-2-methyl-2-phenoxy-propionic acid

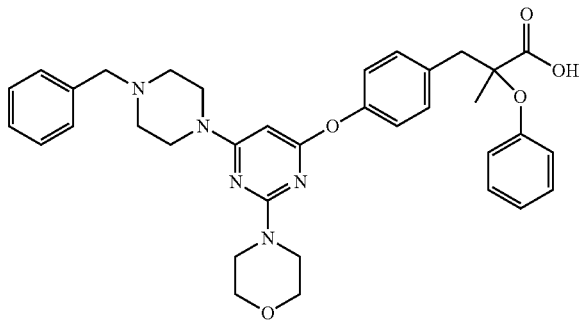 [SMILES: CC(Cc1ccc(Oc2cc(N3CCN(Cc4ccccc4)CC3)nc(N3CCOCC3)n2)cc1)(Oc1ccccc1)C(=O)O]

This compound was prepared by means of a procedure similar to that used for Example 47.

mp 127-129° C.; ¹HNMR (300 MHz, CD₃OD): δ1.38 (s, 3H), 2.78 (t, 4H, J=5.7 Hz), 3.15 (d, 1H, J=13.8 Hz), 3.33 (d, 1H, J=13.8 Hz), 3.52~3.60 (m, 12H), 3.89 (s, 2H), 5.29 (s, 1H), 6.82~6.96 (m, 3H), 7.06 (d, 2H, J=8.7 Hz), 7.20 (t, 2H, J=8.7 Hz), 7.31 (d, 2H, J=8.4 Hz), 7.18~7.23 (m, 5H); EI-MS: m/e 609 (M⁺), 94 (100%).

Example 54

3-{4-[6-(4-Benzyl-piperazin-1-yl)-2-pyrrolidin-1-yl-pyrimidin-4-yloxy]-phenyl}-2-methyl-2-phenoxy-propionic acid

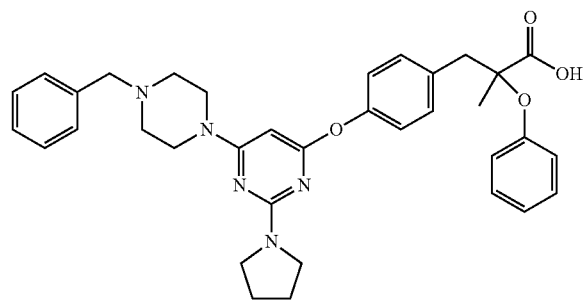 [SMILES: CC(Cc1ccc(Oc2cc(N3CCN(Cc4ccccc4)CC3)nc(N3CCCC3)n2)cc1)(Oc1ccccc1)C(=O)O]

This compound was prepared by means of a procedure similar to that used for Example 47.

mp 126-127° C.; $^1$HNMR (300 MHz, CD$_3$OD): δ 1.40 (s, 3H), 1.91 (m, 4H), 2.78 (m, 4H), 3.15 (d, 1H, J=13.5 Hz), 3.33 (d, 1H, J=13.5 Hz), 3.41 (m, 4H), 3.62 (m, 4H), 3.87 (s, 2H), 5.09 (s, 1H), 6.87~6.93 (m, 3H), 7.02 (d, 2H, J=8.4 Hz), 7.18 (t, 2H, J=8.4 Hz), 7.32 (d, 2H, J=8.4 Hz), 7.37~7.41 (m, 5H); EI-MS: m/e 593 (M$^+$), 94 (100%).

Example 55

3-{4-[2-phenylamino-6-(4-benzyl-piperazin-1-yl)-pyrimidin-4-yloxy]-phenyl}-2-methyl-2-phenoxy-propionic acid

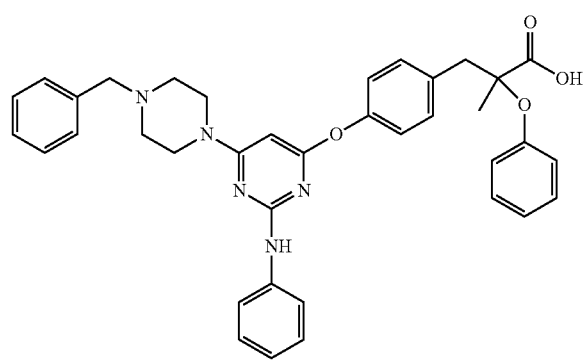 [SMILES: CC(Cc1ccc(Oc2cc(N3CCN(Cc4ccccc4)CC3)nc(Nc3ccccc3)n2)cc1)(Oc1ccccc1)C(=O)O]

This compound was prepared by means of a procedure similar to that used for Example 47.

Example 56

3-{4-[6-(4-Benzyl-piperazin-1-yl)-2-piperazin-1-yl-pyrimidin-4-yloxy]-phenyl}-2-methyl-2-phenoxy-propionic acid

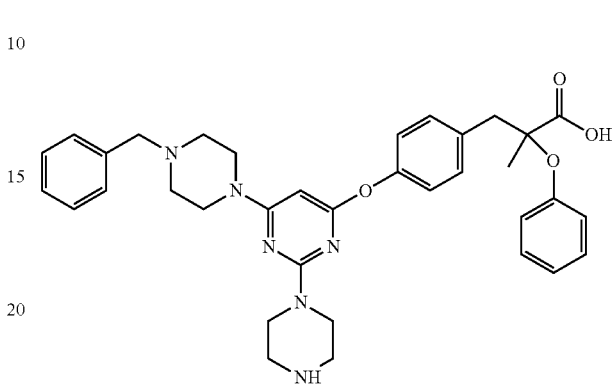

This compound was prepared by means of a procedure similar to that used for Example 47.

Example 57

3-{4-[2,6-Bis-(4-benzyl-piperazin-1-yl)-pyrimidin-4-yloxy]-phenyl}-2-methyl-2-phenoxy-propionic acid

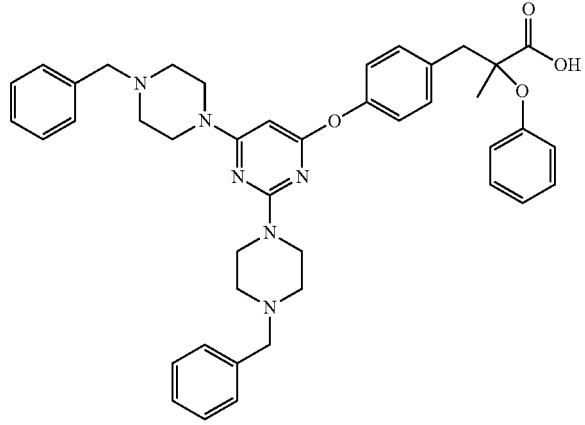 [SMILES: CC(Cc1ccc(Oc2cc(N3CCN(Cc4ccccc4)CC3)nc(N3CCN(Cc4ccccc4)CC3)n2)cc1)(Oc1ccccc1)C(=O)O]

This compound was prepared by means of a procedure similar to that used for Example 47.

The substituents in the compounds of Examples are listed in the following Tables:

| Example No. | Compound No. | $R_2$ | $R_4$ | $R_5$ | $R_6$ | $R_{10}$ | $R_{11}$ | $R_{12}$ |
|---|---|---|---|---|---|---|---|---|
| 1 | 1 | NH$_2$ | H | C$_2$H$_5$ | H | H | H | H |
| 2 | 2 | NH$_2$ | CH$_3$ | Ph | H | H | H | H |
| 3 | 3 | NH$_2$ | CH$_3$ | Ph | H | H | H | H |
| 4 | 4 | NH$_2$ | CH$_3$ | Ph | H | H | H | H |
| 7 | 7 | NH$_2$ | CH$_3$ | Ph | H | H | H | F |
| 8 | 8 | NH$_2$ | CH$_3$ | Ph | H | H | H | CF$_3$ |
| 9 | 9 | NH$_2$ | CH$_3$ | Ph | H | H | CH$_3$ | H |

-continued

| Example No. | Compound No. | R₂ | R₄ | R₅ | R₆ | R₁₀ | R₁₁ | R₁₂ |
|---|---|---|---|---|---|---|---|---|
| 10 | 10 | NH₂ | CH₃ | Ph | H | H | CF₃ | H |
| 11 | 11 | NH₂ | CH₃ | Ph | H | H | Cl | H |
| 12 | 12 | NH₂ | CH₃ | Ph | H | H | F | H |
| 13 | 13 | NH₂ | CH₃ | Ph | H | H | H | Cl |
| 14 | 14 | NH₂ | CH₃ | Ph | H | H | H | (CH₃)₃ |
| 15 | 15 | NH₂ | CH₃ | Ph | H | H | H | Br |
| 16 | 16 | NH₂ | CH₃ | Ph | H | H | Br | H |
| 17 | 17 | NH₂ | CH₃ | Ph | H | H | OPh | H |
| 26 | 26 | NH₂ | CH₃ | Ph | H | H | CN | H |
| 28 | 28 | H | CH₃ | Ph | H | H | H | H |
| 29 | 29 | NH₂ | CH₃ | Biphenyl | H | H | H | H |
| 30 | 30 | NH₂ | CH₃ | 4-OCH₃—Ph | H | H | H | H |
| 31 | 31 | NH₂ | CH₃ | 4-CH₃—Ph | H | H | H | H |
| 32 | 32 | NH₂ | CH₃ | 4-CF₃—Ph | H | H | H | H |
| 33 | 33 | Ph | CH₃ | Ph | H | H | H | H |
| 34 | 34 | CH₃ | CH₃ | Ph | H | H | H | H |
| 35 | 35 | NH₂ | CH₃ | Ph | H | H | H | H |
| 38 | 38 | NH₂ | CH₃ | Ph | H | H | H | NO₂ |
| 41 | 41 | NH₂ | CH₃ | Ph | H | I | H | H |
| 42 | 42 | NH₂ | CH₃ | Ph | H | OCH₃ | H | H |
| 43 | 43 | OPh | CH₃ | Ph | H | H | H | H |
| 45 | 45 | OCH₃ | CH₃ | Ph | H | H | H | H |
| 46 | 46 | OC₂H₅ | CH₃ | Ph | H | H | H | H |
| 47 | 47 | NHBn | CH₃ | Ph | H | H | H | H |
| 48 | 48 | NHCH₃ | CH₃ | Ph | H | H | H | H |
| 49 | 49 | N(CH₃)₂ | CH₃ | Ph | H | H | H | H |
| 50 | 50 | NHC₂H₅ | CH₃ | Ph | H | H | H | H |
| 51 | 51 | N(C₂H₅)₂ | CH₃ | Ph | H | H | H | H |
| 52 | 52 | piperidinyl | CH₃ | Ph | H | H | H | H |
| 53 | 53 | morpholinyl | CH₃ | Ph | H | H | H | H |
| 54 | 54 | pyrrolidinyl | CH₃ | Ph | H | H | H | H |
| 55 | 55 | NHPh | CH₃ | Ph | H | H | H | H |
| 56 | 56 | piperazinyl | CH₃ | Ph | H | H | H | H |
| 57 | 57 | 4-benzyl-piperazin-1-yl | CH₃ | Ph | H | H | H | H |

| Example No. | Compound No. | R₂ | R₄ | R₅ | R₆ | R₈ |
|---|---|---|---|---|---|---|
| 5 | 5 | NH2 | CH3 | Ph | H | 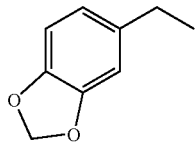 |
| 6 | 6 | NH2 | CH3 | Ph | H | 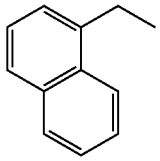 |
| 18 | 18 | NH2 | CH3 | Ph | H | 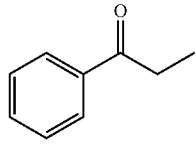 |
| 19 | 19 | NH2 | CH3 | Ph | H | 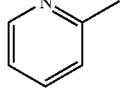 |

-continued

| Example No. | Compound No. | R₂ | R₄ | R₅ | R₆ | R₈ |
|---|---|---|---|---|---|---|
| 20 | 20 | NH2 | CH3 | Ph | H | 2-methylpyrimidin-yl-methyl |
| 21 | 21 | NH2 | CH3 | Ph | H | phenacyl (2-oxo-2-phenylethyl) |
| 22 | 22 | NH2 | CH3 | Ph | H | benzyl |
| 23 | 23 | NH2 | CH3 | Ph | H | 3-chlorobenzyl |
| 24 | 24 | NH2 | CH3 | Ph | H | 2-(4-propylphenyl)-2-oxoethyl |
| 25 | 25 | NH2 | CH3 | Ph | H | 2-(2-methoxyphenyl)-2-oxoethyl |
| 27 | 27 | NH2 | CH3 | Ph | H | 2-cyclohexylethyl |
| 36 | 36 | NH2 | CH3 | Ph | H | 2-(pyridin-2-yl)ethyl |
| 37 | 37 | NH2 | CH3 | Ph | H | 2-(furan-2-yl)ethyl |
| 39 | 39 | NH2 | CH3 | Ph | H | 2-(pyridin-3-yl)ethyl |
| 40 | 40 | NH2 | CH3 | Ph | H | 2-(pyridin-4-yl)ethyl |

-continued

| Example No. | Compound No. | R₂ | R₄ | R₅ | R₆ | R₈ |
|---|---|---|---|---|---|---|
| 44 | 44 | 4-benzylpiperazin-1-yl-methylpiperazine | CH₃ | Ph | H | methoxyphenyl |

Example 58

Transient Transfection and Transcription Assay cDNAs for Human RXR, PPAR were obtained by RTPCR from the human liver or adipose tissues. Amplified cDNAs were cloned into pcDNA3.1 expression vector and the inserts were confirmed by sequencing. U2OS cells were cultured in McCoy's 5A with 10% heat-inactivated fetal bovine serum in a humidified 5% $CO_2$ atmosphere at 37° C. Cells were seeded in 96-well plates the day before transfection to give a confluence of 50-80% at transfection. A total of 60 ng of DNA containing 10 ng of hRXR, 10 ng of pCMV Gal, 10 ng of nuclear receptor expression vectors and 30 ng of the corresponding reporters were cotransfected per well using FuGene6 transfection reagent according to the manufacturer's instructions. Following 24 h after transfection, cells were incubated with 10% charcoal-stripped FBS DMEM and were treated with the individual compound dissolved in DMSO. The final concentration of DMSO in culture medium was 0.1%. Cells were treated with compound for 24 h, and then collected with Cell Culture Lysis buffer. Luciferase activity was monitored using the luciferase assay kit according to the manufacturers instructions. Light emission was read in a Labsystems Ascent Fluoroskan reader. To measure galactosidase activity to normalize the luciferase data, 50 IL of supernatant from each transfection lysate was transferred to a new microplate. Galactosidase assays were performed in the microwell plates using a kit from Promega and read in a microplate reader. Compounds were tested in five concentrations ranging from 0.01 to 10 μM. Cells were treated with compound for 24 h followed by luciferase assay. $EC_{50}$ values were calculated via nonlinear regression using GraphPad PRISM 3.02 (GraphPad Software, San Diego, Calif.). The results were expressed as means (SD).

TABLE 1

| No | $EC_{50}$ (μM) |
|---|---|
| 2 | 6.76 |
| 3 | 3.31 |
| 4 | 5.75 |
| 5 | 6.46 |
| 6 | 3.39 |
| 9 | 4.17 |
| 10 | 4.27 |
| 11 | 5.13 |
| 12 | 6.46 |
| 14 | 6.03 |
| 15 | 5.89 |
| 16 | 6.31 |
| 18 | 6.46 |
| 19 | 6.31 |
| 20 | 5.89 |
| 22 | 4.68 |
| 23 | 4.37 |
| 27 | 5.37 |
| 28 | 4.68 |
| 29 | 2.57 |
| 30 | 5.75 |
| 31 | 3.80 |
| 32 | 2.24 |
| 37 | 3.89 |
| 43 | 1.62 |
| 44 | 4.68 |
| 47 | 6.31 |
| 49 | 2.95 |
| 50 | 6.03 |
| 51 | 7.08 |
| 52 | 4.68 |
| 53 | 3.98 |
| 54 | 3.80 |

Example 59

The Effect of Compound 2 in the Han:Sprd Rat Model of Adpkd

We examined the renal protection, potential side effects of compound 2 and its effect on life span in the Han:SPRD rat model of ADPKD.

1. Animals and Materials

Han: SPRD rats were obtained from our own breeding colony that is derived from animals that were kindly provided to us by Mayo Clinic (Rochester Minn.), All animal procedures and care were taken at the SPF-level Laboratory Animal Center of the Second Military Medical University (Shanghai, Calif.). Carboxymethyl cellulose sodium (CMC-Na) was purchased from Shanghai Chemical Reagent Company. Automatic clinical chemistry analyzer (Hitachi Clinical Analyzer 7080).

2. Methods 2.1 Experimental protocol: A total of 48 Han:SPRD rats (about ⅔ rats were Cy/+, ⅓ were +/+, homozygote rats −/− die within 3 weeks), all at 3 weeks of age, were randomized into 2 groups: negative control group and treatment groups (10 mg/kg.d compound 2). The rats of negative control group were given 1% CMC-Na, while the rats of treatment group were given 10 mg/kg.d compound 2 (suspended in 1% CMC-Na) by daily gavage from 3 weeks through 11 weeks of age, removal +/+ rats in both groups, then general animal feeds were given to rats in control group, the rats of treatment group were given animal feeds added by 0.03% of compound 2 (approximately 10 mg/kg. d), both groups were maintained with free access to water. Long-term observation of the rats until they died, record the length of their life span.

2.2 Physiological and biochemical indexes: since the day of treatment, general state and body weight of rats were examined and recorded every month, Blood (2 ml) was obtained from the rat orbital venous plexus using a glass capillary tube, then centrifuged for 10 minutes at 4000 rpm to collect serum for biochemical analysis including blood urea nitrogen (BUN), ALT, AST, serum lipids et. Urine was collected using Metabolic Cage for 24-hour urine protein analysis.

3. Results 3.1 Blood urea nitrogen (BUN): After 2 months of treatment, the average BUN level was lower in the treatment group compared with control group (P<0.001), indicating that compound 2 treatment delayed the progression of renal failure.

TABLE 2

Blood urea nitrogen (BUN) levels

| Intervention time | Blood urea nitrogen (BUN) levels (mmol/L) | |
|---|---|---|
| | Negative Control Group | Treatment Group |
| baseline | 4.79 ± 0.66 | 4.97 ± 0.67 |
| 1 month | 11.54 ± 0.81 | 11.55 ± 0.57 |
| 2 month | 13.80 ± 1.63 | 12.36 ± 0.77* |
| 3 month | 15.07 ± 1.60 | 12.58 ± 1.35** |
| 4 month | 15.44 ± 0.90 | 12.79 ± 1.41*** |
| 5 month | 15.55 ± 1.11 | 13.10 ± 1.64*** |
| 6 month | 16.34 ± 1.47 | 13.26 ± 1.05*** |
| 7 month | 17.32 ± 1.02 | 12.60 ± 1.40*** |
| 8 month | 18.62 ± 1.93 | 13.16 ± 1.73*** |
| 9 month | 21.97 ± 2.94 | 12.87 ± 2.72*** |
| 10 month | 27.87 ± 1.36 | 13.17 ± 3.70*** |

*P < 0.05;
**P < 0.01

3.2 24-hour urine protein: After 2 months of treatment, the average 24-hour urine protein level was lower in the treatment group compared with the negative control group (P<0.001), revealing a significant renal protection after the use of the compound 2.

TABLE 3

24-hour urine protein level

| Intervention time | 24-hour urine protein level (mg/24 h) | |
|---|---|---|
| | Negative Control Group | Treatment Group |
| baseline | Non-detected | Non-detected |
| 1 month | 65.0 ± 3.1 | 62.3 ± 6.3 |
| 2 month | 73.9 ± 8.9 | 64.1 ± 5.0* |
| 3 month | 69.8 ± 25.6 | 67.1 ± 4.9 |
| 4 month | 80.5 ± 11.1 | 66.3 ± 4.6*** |
| 5 month | 75.4 ± 8.0 | 67.1 ± 3.6* |
| 6 month | 80.3 ± 9.3 | 66.0 ± 8.6** |
| 7 month | 80.0 ± 9.1 | 64.4 ± 2.8*** |
| 8 month | 82.6 ± 6.1 | 70.4 ± 8.8** |
| 9 month | 88.3 ± 7.0 | 67.8 ± 3.2*** |
| 10 month | 88.1 ± 10.9 | 70.0 ± 5.9*** |

*P < 0.05;
**P < 0.01

3.3 Comparison of long-term survival: The average survival time of the control group is 389.3 days; the average survival time of treatment group is 451.1+ days with 2 rats still alive. Detail in Attached Table.

3.4 after compound 2 treatment, no statistically significant change in body weight was noted, the values of serum ALT, AST and serum lipids were still within the normal range.

The result of the above experiments clearly indicates that compound 2, at suitable dose, can delay the progression of renal failure, attenuate albuminuria, prolong the life span of Han:SPRD rats without any obvious poisonous and side effects during the intervention time (See FIG. 1).

Example 60

Anticancer Effects of Peroxisome Proliferator-Activated Receptor γ Agonists

The growth inhibition was evaluated by the modified MTT assay. Briefly, the cells were seeded at 1×104 cells/well in 96-well plates (Falcon, Calif., USA), and incubated for 24 h in 100 mL culture media with 10% FCS. The media were then replaced by serum-free medium. After 24 h, the media were placed in triplicate with grade concentrations of compounds. As controls, the cells were cultivated in DMEM/F12 only. The cells were then treated by MTT (Sigma, USA) assay, 10 mL (5 g/L) for 4 h. After the removal of the supernatant, the purple-blue sediment was dissolved in 100 μL/well DMSO, and the optical densities were read on the multi-well scanning spectrophotometer (Labsystems Dragon, Finland) at 492 nm (A492). The growth inhibition rate (GIR) of the treated cells was calculated using Equation:

$$GIR(\%) = \{1 - [A490/A490(\text{control})]\} \times 100\%$$

The results were also converted to IC50 (the compound concentration required for 50% growth inhibition of tumor cells), which were calculated by using the sigmoidal fitting model by the Origin 7.0 software (OriginLab, Northampton, Mass., USA). The mean IC50 was determined from the results of 3 independent tests.

TABLE 4

| | IC50 | | | |
|---|---|---|---|---|
| Compound | SPC-A1 | T24 | HepG2 | MCF-7 |
| Rosiglitazone | 59.8 μM | 69.0 μM | 80.2 μM | 45.6 μM |
| 2 | 65.5 μM | 72.0 μM | 80.6 μM | 55.0 μM |
| 5 | >50 μM | >50 μM | >50 μM | >50 μM |
| 6 | 49.8 μM | 36.3 μM | 24.8 μM | 42.2 μM |
| 7 | >50 μM | >50 μM | >50 μM | >50 μM |
| 8 | 42.5 μM | 36.2 μM | >50 μM | 28.5 μM |
| 9 | 48.9 μM | >50 μM | >50 μM | 38.0 μM |
| 10 | 25.1 μM | 29.1 μM | 38.1 μM | 15.1 μM |
| 11 | 47.6 μM | >50 μM | >50 μM | 40.6 μM |
| 12 | >50 μM | >50 μM | >50 μM | >50 μM |
| 13 | >50 μM | 45.6 μM | >50 μM | 48.9 μM |
| 14 | 8.6 μM | 12.5 μM | 26.5 μM | 7.9 μM |
| 15 | 45.3 μM | >50 μM | >50 μM | 42.2 μM |
| 16 | 37.0 μM | 41.0 μM | 48.0 μM | 30.0 μM |
| 18 | >50 μM | >50 μM | >50 μM | >50 μM |
| 19 | 42.5 μM | 30.8 μM | 49.5 μM | >50 μM |
| 20 | 29.1 μM | 20.1 μM | 32.6 μM | 35.7 μM |
| 21 | >50 μM | >50 μM | >50 μM | >50 μM |
| 22 | 32.5 μM | 22.6 μM | 29.7 μM | 15.5.6 μM |
| 23 | 12.0 μM | 15.2 μM | 20.0 μM | 11.8 μM |
| 24 | 43.7 μM | 39.4 μM | >50 μM | 38.2 μM |
| 25 | >50 μM | >50 μM | >50 μM | >50 μM |
| 26 | 37.7 μM | 38.8 μM | 35.6 μM | 23.3 μM |
| 27 | >50 μM | >50 μM | 44.5 μM | >50 μM |
| 28 | 28.6 μM | 19.6 μM | 29.3 μM | 14.6 μM |
| 29 | 34.1 μM | 40.0 μM | >50 μM | >50 μM |
| 30 | 38.9 μM | >50 μM | >50 μM | 42.8 μM |
| 31 | 35.3 μM | 40.8 μM | 45.5 μM | 29.3 μM |
| 32 | 28.0 μM | 37.7 μM | 30.0 μM | 34.2 μM |
| 36 | >50 μM | >50 μM | >50 μM | >50 μM |
| 37 | 37.6 μM | 40.6 μM | >50 μM | 47.6 μM |
| 38 | >50 μM | 40.3 μM | >50 μM | 45.3 μM |
| 39 | 43.5 μM | >50 μM | >50 μM | 38.8 μM |
| 40 | 46.5 μM | >50 μM | >50 μM | 45.2 μM |

TABLE 4-continued

| Compound | IC50 | | | |
| --- | --- | --- | --- | --- |
| | SPC-A1 | T24 | HepG2 | MCF-7 |
| 43 | 32.5 μM | >50 μM | >50 μM | 33.5 μM |
| 44 | 14.1 μM | 11.1 μM | 35.2 μM | 15.4 μM |
| 47 | 31.5 μM | >50 μM | >50 μM | 22.8 μM |
| 49 | >50 μM | >50 μM | >50 μM | >50 μM |
| 50 | 46.6 μM | >50 μM | >50 μM | 33.7 μM |
| 51 | 36.6 μM | 21.9 μM | 37.5 μM | 27.6 μM |
| 52 | 7.8 μM | 12.4 μM | 17.9 μM | 17.6 μM |
| 53 | 22.4 μM | 15.8 μM | 22.2 μM | 12.5 μM |
| 54 | >50 μM | >50 μM | >50 μM | >50 μM |

The results indicate that most of the synthesized compounds demonstrated moderate anti-proliferatory effects on SPC-A1, T24, HepG2, MCF-7 cell lines, especially some of them showed inhibitory capability approximately several times higher than that of the rosiglitazone.

The invention claimed is:

1. A compound represented by Structural Formula I, or pharmaceutically acceptable salts thereof:

Structural Formula I

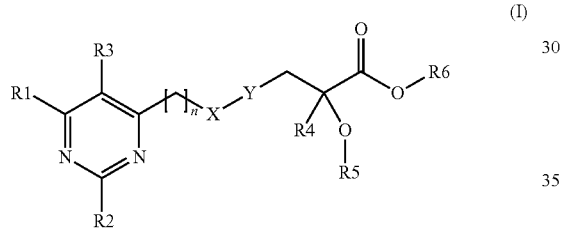

wherein:

X is $CH_2$, $CH(OH)$, $C(O)O$, $NH$, $S$, or $SO_2$;

Y is an unsubstituted or substituted phenyl, wherein the substituted phenyl is substituted by one or more of the following groups: $C_1$-$C_6$ straight-chain or branched-chain alkyl, halogen, $C_1$-$C_6$ haloalkyl, amino, mercapto, cyano, nitro, hydroxyl, trifluoromethyl, and trifluoromethoxy;

n is 0, 2, 3, or 4;

$R_1$ is a hydro, or $C_1$-$C_6$ alkyl, $C_1$-$C_8$ alkoxyl, mercapto, cyano, nitro, hydroxyl, trifluoromethyl, trifluoromethoxy, phenoxy, unsubstituted $C_3$-$C_6$ heterocycloalkyl or substituted $C_3$-$C_6$ heterocycloalkyl, wherein the substituted $C_3$-$C_6$ heterocycloalkyl is substituted by one or more of the following groups:

$C_1$-$C_8$ alkyl, halogen, $C_3$-$C_6$ cycloalkyl, ($C_3$-$C_6$)cycloalkyl($C_1$-$C_6$)alkyl, $C_1$-$C_6$ haloalkyl, amino, mercapto, cyano, nitro, hydroxyl, trifluoromethyl, trifluoromethoxy; unsubstituted or substituted $C_6$-$C_{12}$ heteroaryl containing one or two oxygen or nitrogen, unsubstituted or substituted $C_3$-$C_6$ heterocycloalkyl containing one or two oxygen or nitrogen, unsubstituted or substituted ($C_6$-$C_{12}$)heterocycloalkyl($C_1$-$C_6$) alkyl containing one or two oxygen or nitrogen, unsubstituted or substituted phenyl, unsubstituted or substituted ($C_5$-$C_{12}$)aryl($C_1$-$C_6$)alkyl, unsubstituted or substituted phenoxy, and unsubstituted or substituted carbobenzoxy, wherein the substituted groups are independently substituted by one or more of the following groups:

halogen, oxo, $C_1$-$C_6$ alkyl, $C_1$-$C_8$ alkoxyl, $C_1$-$C_6$ haloalkyl, amino, mercapto, cyano, nitro, hydroxyl, trifluoromethyl, trifluoromethoxy; and unsubstituted or substituted phenyl or phenoxy, wherein the substituted phenyl or phenoxy is independently substituted by one or more substituents selected from:

halogen, $C_1$-$C_6$ haloalkyl, amino, mercapto, cyano, nitro, hydroxyl, trifluoromethyl, and trifluoromethoxy;

$R_2$ is H, phenyl, $C_1$-$C_6$ alkyl, $C_1$-$C_8$ alkoxyl, amino, mercapto, cyano, nitro, hydroxyl, trifluoromethyl, trifluoromethoxy, or unsubstituted or substituted amino, wherein the substituted groups are independently substituted by one or more of the following groups:

$C_1$-$C_6$ alkyl, $C_3$-$C_7$ carbocyclyl, phenyl, benzyl, aralkyl, sulfanilamino, pyridyl, $C_1$-$C_4$ acyl; unsubstituted or substituted $C_3$-$C_6$ heterocycloalkyl containing one or two oxygen or nitrogen, and unsubstituted or substituted phenoxy, wherein the substituted amino group is substituted by one or more of the following groups:

halogen, $C_1$-$C_6$ haloalkyl, amino, mercapto, cyano, nitro, hydroxyl, trifluoromethyl, trifluoromethoxy, and benzyl;

$R_3$ is H, $C_1$-$C_8$ alkoxyl, halogen, mercapto, cyano, nitro, hydroxyl, trifluoromethyl, trifluoromethoxy, $C_1$-$C_6$ straight-chain or branched-chain alkyl, phenyl, aralkyl, thioureido, or unsubstituted or substituted amino, wherein the substituted amino group is substituted by one or more of the following groups: $C_1$-$C_6$ straight-chain or branched-chain alkyl, $C_3$-$C_6$ heterocycloalkyl, phenyl, aralkyl, sulfanilamino, pyridyl, and $C_1$-$C_4$ acyl;

$R_4$ is H, $C_1$-$C_6$ straight-chain or branched-chain alkyl, $C_1$-$C_8$ alkoxyl, mercapto, hydroxyl, trifluoromethyl, trifluoromethoxy, or unsubstituted or substituted phenoxy, wherein the substituted phenoxy is substituted by one or more of the following groups: halogen, $C_1$-$C_6$ haloalkyl, amino, mercapto, hydroxyl, trifluoromethyl, and trifluoromethoxy;

$R_5$ is H, $C_1$-$C_6$ straight-chain or branched-chain alkyl, or unsubstituted or substituted phenyl, wherein the substituted phenoxy is substituted by one or more of the following groups:

halogen, $C_1$-$C_6$ haloalkyl, $C_1$-$C_6$ straight-chain or branched-chain alkyl, $C_1$-$C_8$ alkoxyl, amino, mercapto, cyano, hydroxyl, trifluoromethyl, trifluoromethoxy, and unsubstituted or substituted phenyl, wherein the substituted phenoxy group is substituted by one or more of the following groups:

halogen, $C_1$-$C_4$ haloalkyl, amino, mercapto, hydroxyl, trifluoromethyl, and trifluoromethoxy;

$R_6$ is H, $C_1$-$C_6$ straight-chain or branched-chain alkyl.

2. The compound or pharmaceutically acceptable salts thereof of claim 1, wherein the compound has a structure represented by Structural Formula II:

Structural Formula II

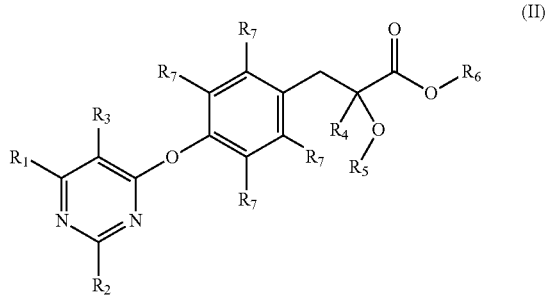

wherein:
$R_1$, $R_2$, $R_3$, $R_4$, $R_5$ and $R_6$ is as defined for Structural Formula I;
$R_7$ are each, independently, H, $C_1$-$C_6$ straight-chain or branched-chain alkyl, halo, $C_1$-$C_6$ haloalkyl, amino, mercapto, cyano, nitro, hydroxyl, trifluoromethyl, or trifluoromethoxy.

3. The compound or pharmaceutically acceptable salts thereof of claim 2, wherein the compound has a structure represented by Structural Formula III:

Structural Formula III

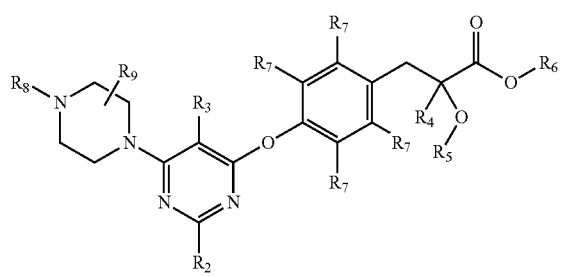

wherein:
$R_2$, $R_3$, $R_4$, $R_5$, $R_6$ and $R_7$ are as defined for Structural Formula II;
$R_9$ are each, independently, H, $C_1$-$C_6$ straight-chain or branched-chain alkyl, $C_3$-$C_6$ cycloalkyl, $C_1$-$C_6$ haloalkyl; unsubstituted or substituted $C_6$-$C_{12}$ heteroaryl containing one or two oxygen or nitrogen, unsubstituted or substituted $C_3$-$C_6$ heterocycloalkyl containing one or two oxygen or nitrogen, unsubstituted or substituted ($C_6$-$C_{12}$)heterocycloalkyl($C_1$-$C_6$)alkyl containing one or two oxygen or nitrogen, unsubstituted or substituted phenyl, unsubstituted or substituted ($C_5$-$C_{12}$)aryl($C_1$-$C_6$)alkyl, unsubstituted or substituted phenoxy, unsubstituted or substituted carbobenzoxy, wherein the substituted groups are independently substituted by one or more of the following groups:
halogen, $C_1$-$C_6$haloalkyl, $C_1$-$C_6$ alkyl, $C_1$-$C_8$ alkoxyl, amino, mercapto, cyano, nitro, hydroxyl, trifluoromethyl, trifluoromethoxy, unsubstituted or substituted phenyl or phenoxy, wherein the substituted phenyl or phenoxy is independently substituted by one or more of the following groups:
halogen, $C_1$-$C_6$ haloalkyl, amino, mercapto, cyano, hydroxyl, trifluoromethyl, and trifluoromethoxy;

$R_9$ is H, $C_1$-$C_8$ straight-chain or branched-chain alkyl, halogen, $C_1$-$C_4$ haloalkyl, amino, mercapto, cyano, hydroxyl, trifluoromethyl, or trifluoromethoxy.

4. The compound or pharmaceutically acceptable salts thereof of claim 3, wherein the compound has a structure represented by Structural Formula IV:

Structural Formula IV

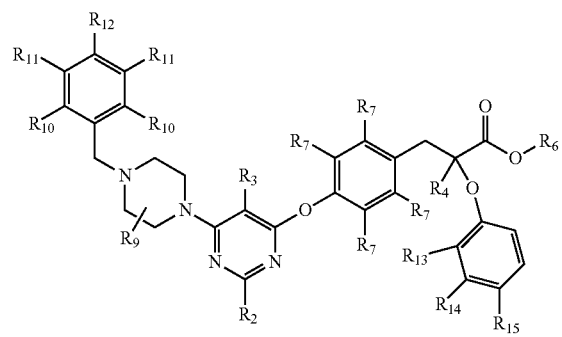

wherein:
$R_2$, $R_3$, $R_4$, $R_6$, $R_7$ and $R_9$ are as defined for Structural Formula III;
$R_{10}$, $R_{11}$, and $R_{12}$ are H, halogen, $C_1$-$C_6$ haloalkyl, $C_1$-$C_6$ straight-chain or branched-chain alkyl, $C_1$-$C_8$ alkoxyl, amino, mercapto, cyano, nitro, hydroxyl, trifluoromethyl, trifluoromethoxy, unsubstituted or substituted phenyl or phenoxy, wherein the substituted phenyl or phenoxy is independently substituted by one or more of the following groups:
halogen, $C_1$-$C_6$ haloalkyl, amino, mercapto, cyano, hydroxyl, trifluoromethyl, and trifluoromethoxy;
$R_{13}$, $R_{14}$, and $R_{15}$ are independently halogen, $C_1$-$C_6$ haloalkyl, amino, mercapto, cyano, hydroxyl, trifluoromethyl, trifluoromethoxy, and unsubstituted or substituted phenyl, wherein the substituted phenyl is substituted by one or more of the following groups:
halogen, $C_1$-$C_6$ haloalkyl, amino, mercapto, hydroxyl, trifluoromethyl, and trifluoromethoxy.

5. The compound or pharmaceutically acceptable salts thereof claim 4, wherein the compound has a structure represented by Structural Formula V:

Structural Formula V

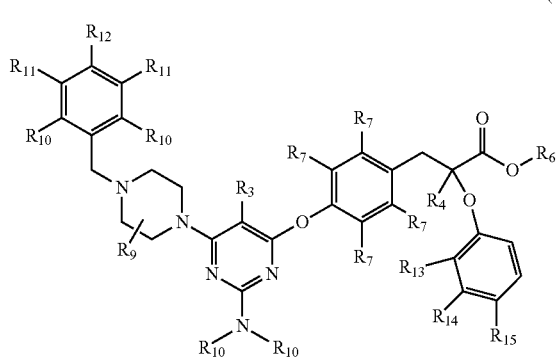

wherein:

$R_3$, $R_4$, $R_6$, $R_7$, $R_9$, $R_{10}$, $R_{11}$, $R_{12}$, $R_{13}$, $R_{14}$, and $R_{15}$ are as defined for Structural Formula IV;

$R_{16}$ optionally and independently substituted one or two times with $C_1$-$C_6$ straight-chain or branched-chain alkyl, $C_3$-$C_7$ cycloalkyl, phenyl, aralkyl, sulfanilamino, pyridyl, $C_1$-$C_4$ acyl; unsubstituted or substituted $C_3$-$C_6$ heterocycloalkyl, wherein the substituted $C_3$-$C_6$ heterocycloalkyl is substituted by one or more of the following groups:

halogen, $C_1$-$C_6$ haloalkyl, amino, mercapto, cyano, hydroxyl, trifluoromethyl, and trifluoromethoxy.

6. A process for preparing a compound represented by Structural Formula I

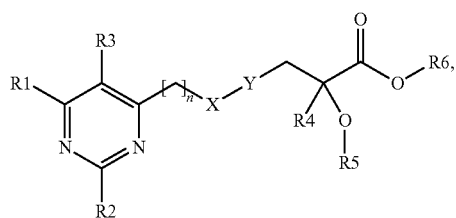

(I)

or pharmaceutically acceptable salts thereof, which comprises the step of:

treating compound

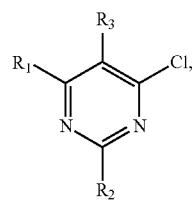

(Ia)

in the presence of cesium carbonate, with compound

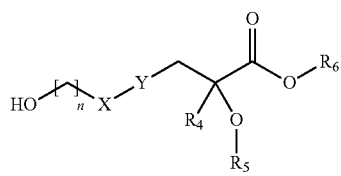

(Ib)

in a polar solvent at a temperature of about 60° C. to about 100° C. to form compound

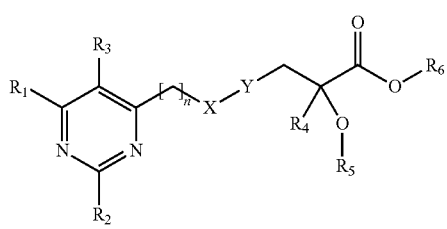

(I)

wherein:

X is $CH_2$, CH(OH), C(O)O, NH, S, or $SO_2$;

Y is an unsubstituted or substituted phenyl, wherein the substituted phenyl is substituted by one or more of the following groups: $C_1$-$C_6$ straight-chain or branched-chain alkyl, halogen, $C_1$-$C_6$ haloalkyl, amino, mercapto, cyano, nitro, hydroxyl, trifluoromethyl, and trifluoromethoxy;

n is 0, 2, 3, or 4;

$R_1$ is a hydro, or $C_1$-$C_6$ alkyl, $C_1$-$C_8$ alkoxyl, mercapto, cyano, nitro, hydroxyl, trifluoromethyl, trifluoromethoxy, phenoxy, unsubstituted $C_3$-$C_6$ heterocycloalkyl or substituted $C_3$-$C_6$ heterocycloalkyl, wherein the substituted $C_3$-$C_6$ heterocycloalkyl is substituted by one or more of the following groups:

$C_1$-$C_8$ alkyl, halogen, $C_3$-$C_6$ cycloalkyl, ($C_3$-$C_6$)cycloalkyl($C_1$-$C_6$)alkyl, $C_1$-$C_6$ haloalkyl, amino, mercapto, cyano, nitro, hydroxyl, trifluoromethyl, trifluoromethoxy; unsubstituted or substituted $C_6$-$C_{12}$ heteroaryl containing one or two oxygen or nitrogen, unsubstituted or substituted $C_3$-$C_6$ heterocycloalkyl containing one or two oxygen or nitrogen, unsubstituted or substituted ($C_6$-$C_{12}$)heterocycloalkyl($C_1$-$C_6$) alkyl containing one or two oxygen or nitrogen, unsubstituted or substituted phenyl, unsubstituted or substituted ($C_5$-$C_{12}$)aryl($C_1$-$C_6$)alkyl, unsubstituted or substituted phenoxy, and unsubstituted or substituted carbobenzoxy, wherein the substituted groups are independently substituted by one or more of the following groups:

halogen, oxo, $C_1$-$C_6$ alkyl, $C_1$-$C_8$ alkoxyl, $C_1$-$C_6$ haloalkyl, amino, mercapto, cyano, nitro, hydroxyl, trifluoromethyl, trifluoromethoxy; and unsubstituted or substituted phenyl or phenoxy, wherein the substituted phenyl or phenoxy is independently substituted by one or more substituents selected from:

halogen, $C_1$-$C_6$ haloalkyl, amino, mercapto, cyano, nitro, hydroxyl, trifluoromethyl, and trifluoromethoxy;

$R_2$ is H, phenyl, $C_1$-$C_6$ alkyl, $C_1$-$C_8$ alkoxyl, amino, mercapto, cyano, nitro, hydroxyl, trifluoromethyl, trifluoromethoxy, or unsubstituted or substituted amino, wherein the substituted amino group is substituted by one or more of the following groups:

$C_1$-$C_6$ alkyl, $C_3$-$C_7$ carbocyclyl, phenyl, benzyl, aralkyl, sulfanilamino, pyridyl, $C_1$-$C_4$ acyl; unsubstituted or substituted $C_3$-$C_6$ heterocycloalkyl containing one or two oxygen or nitrogen, and unsubstituted or substituted phenoxy, wherein the substituted groups are independently substituted by one or more of the following groups:

halogen, $C_1$-$C_6$ haloalkyl, amino, mercapto, cyano, nitro, hydroxyl, trifluoromethyl, trifluoromethoxy, and benzyl;

$R_3$ is H, $C_1$-$C_8$ alkoxyl, halogen, mercapto, cyano, nitro, hydroxyl, trifluoromethyl, trifluoromethoxy, $C_1$-$C_6$ straight-chain or branched-chain alkyl, phenyl, aralkyl, thioureido, or unsubstituted or substituted amino, wherein the substituted amino group is substituted by one or more of the following groups: $C_1$-$C_6$ straight-chain or branched-chain alkyl, $C_3$-$C_6$ heterocycloalkyl, phenyl, aralkyl, sulfanilamino, pyridyl, and $C_1$-$C_4$ acyl;

$R_4$ is H, $C_1$-$C_6$ straight-chain or branched-chain alkyl, $C_1$-$C_8$ alkoxyl, mercapto, hydroxyl, trifluoromethyl, trifluoromethoxy, or unsubstituted or substituted phenoxy, wherein the substituted phenoxy is substituted by one or more of the following groups: halogen, $C_1$-$C_6$ haloalkyl, amino, mercapto, hydroxyl, trifluoromethyl, and trifluoromethoxy;

$R_5$ is H, $C_1$-$C_6$ straight-chain or branched-chain alkyl, or unsubstituted or substituted phenyl, wherein the substituted phenyl group is substituted by one or more of the following groups:

halogen, $C_1$-$C_6$ haloalkyl, $C_1$-$C_6$ straight-chain or branched-chain alkyl, $C_1$-$C_8$ alkoxyl, amino, mercapto, cyano, hydroxyl, trifluoromethyl, trifluoromethoxy, and unsubstituted or substituted phenyl, wherein the substituted phenyl group is substituted by one or more of the following groups:

halogen, $C_1$-$C_4$ haloalkyl, amino, mercapto, hydroxyl, trifluoromethyl, and trifluoromethoxy; and $R_6$ is H, $C_1$-$C_6$ straight-chain or branched-chain alkyl.

7. A process for preparing a compound of Structural Formula II

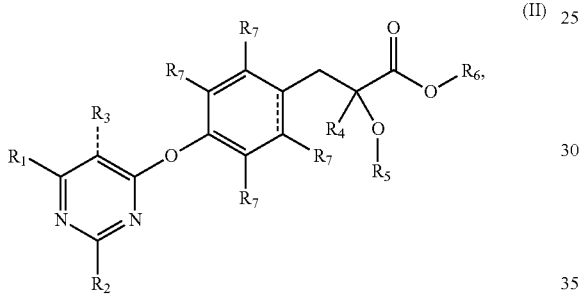

or pharmaceutically acceptable salts thereof, which comprises the step of:

treating compound

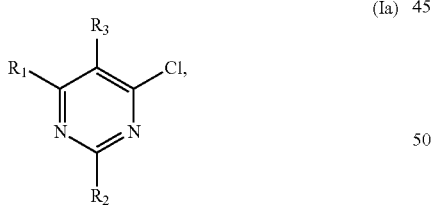

in the presence of cesium carbonate, with compound

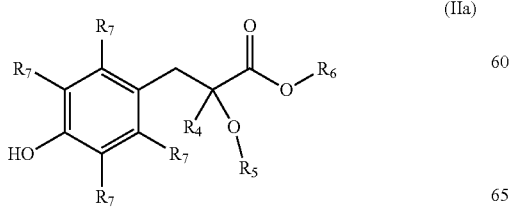

in a polar solvent at a temperature of about 60° C. to about 100° C., to form compound

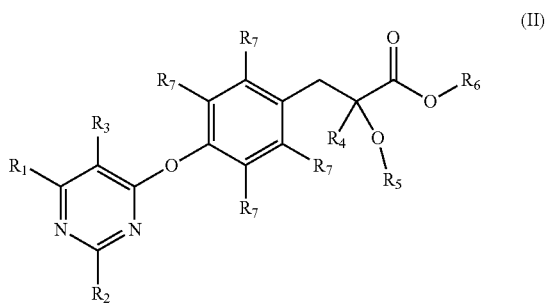

wherein:

$R_1$ is a hydro, or $C_1$-$C_6$ alkyl, $C_1$-$C_8$ alkoxyl, mercapto, cyano, nitro, hydroxyl, trifluoromethyl, trifluoromethoxy, phenoxy, unsubstituted $C_3$-$C_6$ heterocycloalkyl or substituted $C_3$-$C_6$ heterocycloalkyl, wherein the substituted $C_3$-$C_6$ heterocycloalkyl is substituted by one or more of the following groups:

$C_1$-$C_8$ alkyl, halogen, $C_3$-$C_6$ cycloalkyl, ($C_3$-$C_6$)cycloalkyl($C_1$-$C_6$)alkyl, $C_1$-$C_6$ haloalkyl, amino, mercapto, cyano, nitro, hydroxyl, trifluoromethyl, trifluoromethoxy; unsubstituted or substituted $C_6$-$C_{12}$ heteroaryl containing one or two oxygen or nitrogen, unsubstituted or substituted $C_3$-$C_6$ heterocycloalkyl containing one or two oxygen or nitrogen, unsubstituted or substituted ($C_6$-$C_{12}$)heterocycloalkyl($C_1$-$C_6$) alkyl containing one or two oxygen or nitrogen, unsubstituted or substituted phenyl, unsubstituted or substituted ($C_5$-$C_{12}$)aryl($C_1$-$C_6$)alkyl unsubstituted or substituted phenoxy, unsubstituted or substituted carbobenzoxy, wherein the substituted groups are independently substituted by one or more of the following groups:

halogen, oxo, $C_1$-$C_6$ alkyl, $C_1$-$C_8$ alkoxyl, $C_1$-$C_6$ haloalkyl, amino, mercapto, cyano, nitro, hydroxyl, trifluoromethyl, trifluoromethoxy; unsubstituted or substituted phenyl or phenoxy, wherein the substituted phenyl or phenoxy is independently substituted by one or more substituents selected from:

halogen, $C_1$-$C_6$ haloalkyl, amino, mercapto, cyano, nitro, hydroxyl, trifluoromethyl, or trifluoromethoxy;

$R_2$ is H, phenyl, $C_1$-$C_6$ alkyl, $C_1$-$C_8$ alkoxyl, amino, mercapto, cyano, nitro, hydroxyl, trifluoromethyl, trifluoromethoxy, unsubstituted or substituted amino wherein the substituted amino group is substituted by one or more of the following groups:

$C_1$-$C_6$ alkyl, $C_3$-$C_7$ carbocyclyl, phenyl, benzyl, aralkyl, sulfanilamino, pyridyl, $C_1$-$C_4$ acyl; unsubstituted or substituted $C_3$-$C_6$ heterocycloalkyl containing one or two oxygen or nitrogen, and unsubstituted or substituted phenoxy, wherein the substituted groups are independently substituted by one or more of the following groups:

halogen, $C_1$-$C_6$ haloalkyl, amino, mercapto, cyano, nitro, hydroxyl, trifluoromethyl, trifluoromethoxy, or benzyl;

$R_3$ is H, $C_1$-$C_8$ alkoxyl, halogen, mercapto, cyano, nitro, hydroxyl, trifluoromethyl, trifluoromethoxy, $C_1$-$C_6$ straight-chain or branched-chain alkyl, phenyl, aralkyl, thioureido, unsubstituted or substituted amino, wherein the substituted amino group is substituted by one or more of the following groups: $C_1$-$C_6$ straight-chain or branched-chain alkyl, $C_3$-$C_6$ heterocycloalkyl, phenyl, aralkyl, sulfanilamino, pyridyl, and $C_1$-$C_4$ acyl;

$R_4$ is H, $C_1$-$C_6$ straight-chain or branched-chain alkyl, $C_1$-$C_8$ alkoxyl, mercapto, hydroxyl, trifluoromethyl, trifluoromethoxy, unsubstituted or substituted phenoxy, wherein the substituted phenoxy is substituted by one or more of the following groups: halogen, $C_1$-$C_6$ haloalkyl, amino, mercapto, hydroxyl, trifluoromethyl, and trifluoromethoxy;

$R_5$ is H, $C_1$-$C_6$ straight-chain or branched-chain alkyl, unsubstituted or substituted phenyl, wherein the substituted phenyl group is substituted by one or more of the following groups:

halogen, $C_1$-$C_6$ haloalkyl, $C_1$-$C_6$ straight-chain or branched-chain alkyl, $C_1$-$C_8$ alkoxyl, amino, mercapto, cyano, hydroxyl, trifluoromethyl, trifluoromethoxy, unsubstituted or substituted phenyl, wherein the substituted phenyl group is substituted by one or more of the following groups:

halogen, $C_1$-$C_4$ haloalkyl, amino, mercapto, hydroxyl, trifluoromethyl, and trifluoromethoxy;

$R_6$ is H, $C_1$-$C_6$ straight-chain or branched-chain alkyl; and $R_7$ are each, independently, H, $C_1$-$C_6$ straight-chain or branched-chain alkyl, halo, $C_1$-$C_6$ haloalkyl, amino, mercapto, cyano, nitro, hydroxyl, trifluoromethyl, or trifluoromethoxy.

8. The process of claim 7, wherein when $R_4$ is H, the process comprises the steps of:

a) synthesizing α-substituted phenylpropionate ester by reacting

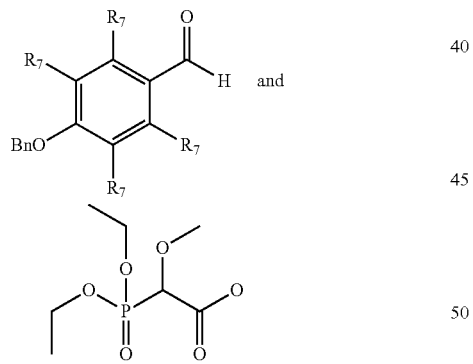

in the presence of tertiary butyl (t-Bu)OK and t-BuOH to form:

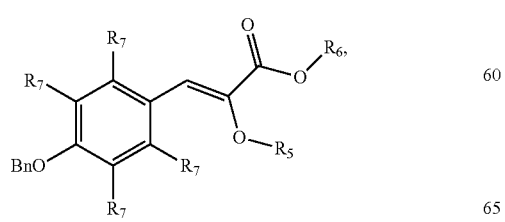

which is reacted in the presence of $H_2Pd/C$ and $C_2H_5OH$ to form:

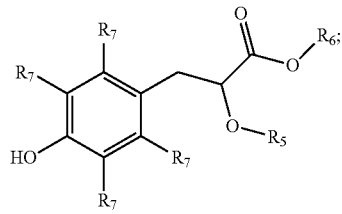

b) preparing substituted or unsubstituted pyridine using a condensation reaction in which

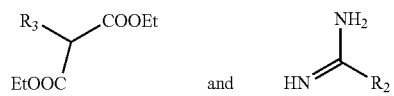

are reacted in the presence of ethanol (Et)ONa/EtOH to form

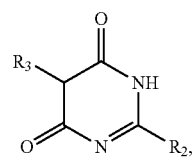

which is reacted in the presence of $POCl_3$ to form which is reacted in the presence of $R_1H$, and dimethylformamide $DMF/Cs_2CO_3$ to form or, when $R_2$ is a substituted amino, $R_3$ is H, and $R_{16}$ is optionally and independently substituted one or two times with $C_1$-$C_6$ straight-chain or branched-chain alkyl, $C_3$-$C_7$ cycloalkyl, phenyl, aralkyl, sulfanilamino, pyridyl, $C_1$-$C_4$ acyl; unsubstituted or substituted $C_3$-$C_6$ heterocycloalkyl, wherein the substituted $C_3$-$C_6$ heterocycloalkyl is substituted by one or more of the following groups: halogen, $C_1$-$C_6$ haloalkyl, amino, mercapto, cyano, hydroxyl, trifluoromethyl, and trifluoromethoxy, by reacting

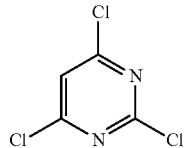

in the presence of acetone and $NHR_{16}R_{16}$ to form

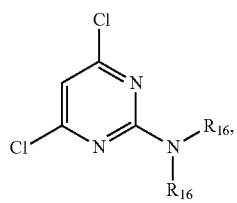

which is reacted in the presence of $R_1H$ and $DMF/Cs_2CO_3$ to form

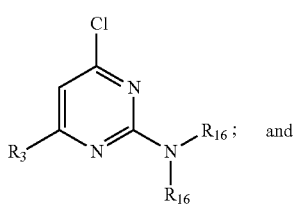

c) preparing 4-(pyrimidinyl-oxy)-phenylpropionate ester by reacting

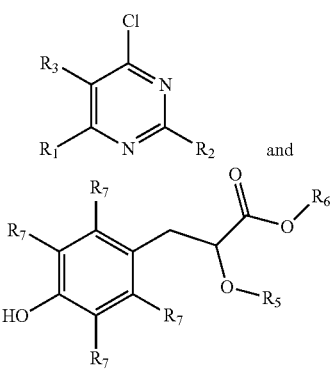

in the presence of $DMF/Cs_2CO_3$ to form

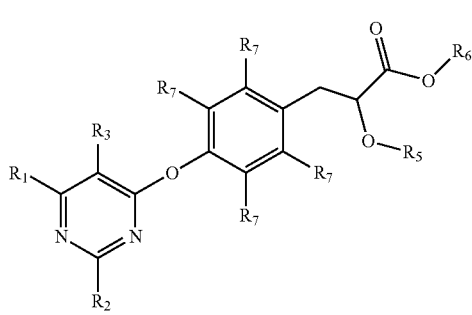

wherein all the substitutes in the reaction are defined for Structural Formulas I-V in any of claims 1-6 above other than $R_4$.

9. The process of claim 7, wherein when $R_4$ is methyl, the process comprises the steps of:

a) preparing the α,α-substituted phenylpropionate ester by reacting

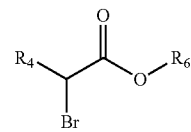

and $R_5OH$ in the presence of $K_2CO_3$ and acetone to form

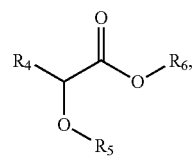

which is then reacted in the presence of LDA/THF and

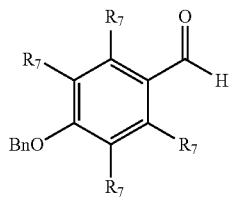

to form

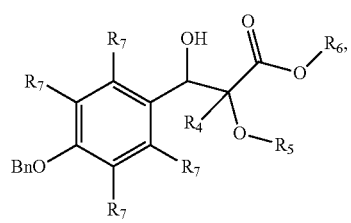

which is then reacted in the presence of $Et_3SiH/BF_3$—$Et_2O$ and $CH_2Cl_2$ to form

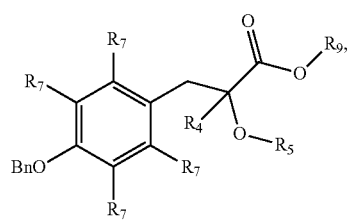

which is reacted in the presence of $H_2Pd/C$ and $C_2H_5OH$ to form

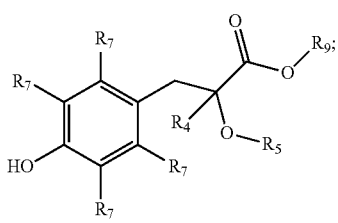

b) preparing substituted or unsubstituted pyridine by reacting

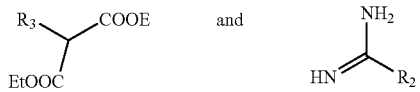

in the presence of EtONa/EtOH to form

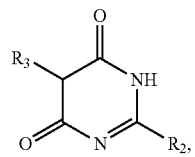

which is then reacted in the presence of $POCl_3$ to form

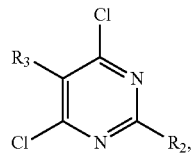

which is then reacted in the presence of $R_1H$ and DMF/$Cs_2CO_3$ to form

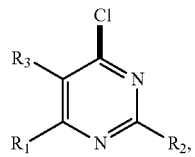

or, when $R_2$ is a substituted amino, $R_3$ is H, and $R_{16}$ is as defined in Structural Formula V by reacting

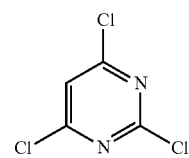

in the presence of acetone and $NHR_{16}R_{16}$ for form

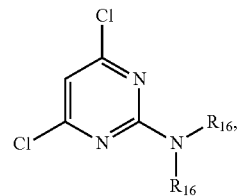

which is reacted in the presence of $R_1H$ and DMF/$Cs_2CO_3$ to form

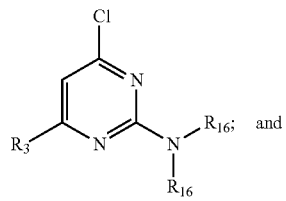

c) preparing 4-(pyrimidinyl-oxy)-phenylpropionate ester by reacting

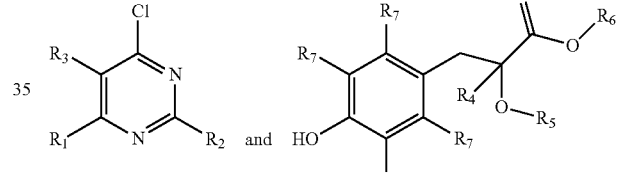

in the presence of DMF and $Cs_2CO_3$ to form

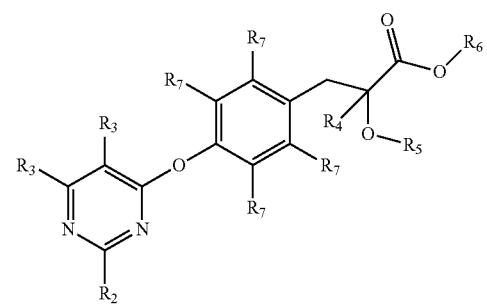

wherein all the substitutes in the reaction are defined for Structural Formulas I-V in any of claims 1-6 above.

10. A pharmaceutical composition comprising:
(i) at least one compound selected from the compounds of Structural Formula I, or the pharmaceutically acceptable salts thereof, Structural Formula I

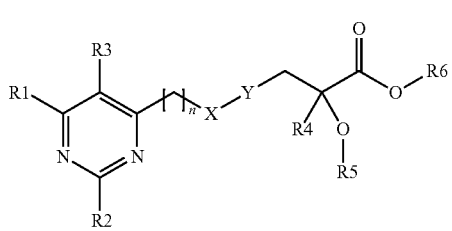

wherein:

X is $CH_2$, $CH(OH)$, $C(O)O$, $NH$, $S$, or $SO_2$;

Y is an unsubstituted or substituted phenyl, wherein the substituted phenyl is substituted by one or more of the following groups: $C_1$-$C_6$ straight-chain or branched-chain alkyl, halogen, $C_1$-$C_6$ haloalkyl, amino, mercapto, cyano, nitro, hydroxyl, trifluoromethyl, and trifluoromethoxy;

n is 0, 2, 3, or 4;

$R_1$ is a hydro, or $C_1$-$C_6$ alkyl, $C_1$-$C_8$ alkoxyl, mercapto, cyano, nitro, hydroxyl, trifluoromethyl, trifluoromethoxy, phenoxy, unsubstituted $C_3$-$C_6$ heterocycloalkyl or substituted $C_3$-$C_6$ heterocycloalkyl, wherein the substituted $C_3$-$C_6$ heterocycloalkyl is substituted by one or more of the following groups:

$C_1$-$C_8$ alkyl, halogen, $C_3$-$C_6$ cycloalkyl, ($C_3$-$C_6$)cycloalkyl($C_1$-$C_6$)alkyl, $C_1$-$C_6$ haloalkyl, amino, mercapto, cyano, nitro, hydroxyl, trifluoromethyl, trifluoromethoxy; unsubstituted or substituted $C_6$-$C_{12}$ heteroaryl containing one or two oxygen or nitrogen, unsubstituted or substituted $C_3$-$C_6$ heterocycloalkyl containing one or two oxygen or nitrogen, unsubstituted or substituted ($C_6$-$C_{12}$)heterocycloalkyl($C_1$-$C_6$) alkyl containing one or two oxygen or nitrogen, unsubstituted or substituted phenyl, unsubstituted or substituted ($C_5$-$C_{12}$)aryl($C_1$-$C_6$)alkyl, unsubstituted or substituted phenoxy, and unsubstituted or substituted carbobenzoxy, wherein the substituted groups are independently substituted by one or more of the following groups:

halogen, oxo, $C_1$-$C_6$ alkyl, $C_1$-$C_8$ alkoxyl, $C_1$-$C_6$ haloalkyl, amino, mercapto, cyano, nitro, hydroxyl, trifluoromethyl, trifluoromethoxy; and unsubstituted or substituted phenyl or phenoxy, wherein the substituted phenyl or phenoxy is independently substituted by one or more substituents selected from:

halogen, $C_1$-$C_6$ haloalkyl, amino, mercapto, cyano, nitro, hydroxyl, trifluoromethyl, and trifluoromethoxy;

$R_2$ is H, phenyl, $C_1$-$C_6$ alkyl, $C_1$-$C_8$ alkoxyl, amino, mercapto, cyano, nitro, hydroxyl, trifluoromethyl, trifluoromethoxy, or unsubstituted or substituted amino, wherein the substituted amino group is substituted by one or more of the following groups:

$C_1$-$C_6$ alkyl, $C_3$-$C_7$ carbocyclyl, phenyl, benzyl, aralkyl, sulfanilamino, pyridyl, $C_1$-$C_4$ acyl; unsubstituted or substituted $C_3$-$C_6$ heterocycloalkyl containing one or two oxygen or nitrogen, and unsubstituted or substituted phenoxy, wherein the substituted groups are independently substituted by one or more of the following groups:

halogen, $C_1$-$C_6$ haloalkyl, amino, mercapto, cyano, nitro, hydroxyl, trifluoromethyl, trifluoromethoxy, and benzyl;

$R_3$ is H, $C_1$-$C_8$ alkoxyl, halogen, mercapto, cyano, nitro, hydroxyl, trifluoromethyl, trifluoromethoxy, $C_1$-$C_6$ straight-chain or branched-chain alkyl, phenyl, aralkyl, thioureido, or unsubstituted or substituted amino, wherein the substituted amino group is substituted by one or more of the following groups: $C_1$-$C_6$ straight-chain or branched-chain alkyl, $C_3$-$C_6$ heterocycloalkyl, phenyl, aralkyl, sulfanilamino, pyridyl, and $C_1$-$C_4$ acyl;

$R_4$ is H, $C_1$-$C_6$ straight-chain or branched-chain alkyl, $C_1$-$C_8$ alkoxyl, mercapto, hydroxyl, trifluoromethyl, trifluoromethoxy, or unsubstituted or substituted phenoxy, wherein the substituted phenoxy is substituted by one or more of the following groups: halogen, $C_1$-$C_6$ haloalkyl, amino, mercapto, hydroxyl, trifluoromethyl, and trifluoromethoxy;

$R_5$ is H, $C_1$-$C_6$ straight-chain or branched-chain alkyl, or unsubstituted or substituted phenyl, wherein the substituted phenyl group is substituted by one or more of the following groups:

halogen, $C_1$-$C_6$ haloalkyl, $C_1$-$C_6$ straight-chain or branched-chain alkyl, $C_1$-$C_8$ alkoxyl, amino, mercapto, cyano, hydroxyl, trifluoromethyl, trifluoromethoxy, and unsubstituted or substituted phenyl, wherein the substituted phenyl group is substituted by one or more of the following groups:

halogen, $C_1$-$C_4$ haloalkyl, amino, mercapto, hydroxyl, trifluoromethyl, and trifluoromethoxy;

$R_6$ is H, $C_1$-$C_6$ straight-chain or branched-chain alkyl; and (ii) pharmaceutically acceptable carrier, excipient or retarder.

11. The pharmaceutical composition of claim 10, wherein said pharmaceutical composition is in the form of troche, capsule, powder, syrup, solution, suspending agent or aerosol.

12. The pharmaceutical composition of claim 10, wherein said pharmaceutical composition is formulated in unit dose form.

13. The pharmaceutical composition of claim 10, wherein the amount of component (i) is in the range from 0.05 to 500 mg.

14. The pharmaceutical composition of claim 10, wherein the amount of component (i) is 0.001-99.9 weight percent based on the total weight of the pharmaceutical composition.

15. The pharmaceutical composition of claim 10 further comprising one or more other medicine in the treatment and prevention of polycystic kidney disease.

16. A method for the treatment of the subject suffering from polycystic kidney disease comprising administrating an effective amount of at least one compound selected from the compounds of Structural Formula I, or the pharmaceutically acceptable salts thereof to the subject in need of such treatment Structural Formula I

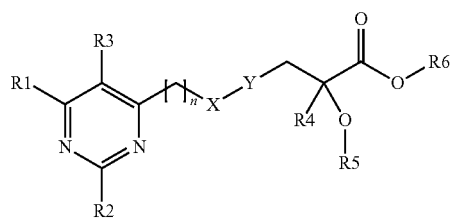

wherein:
X is $CH_2$, $CH(OH)$, $C(O)O$, $NH$, $S$, or $SO_2$;
Y is an unsubstituted or substituted phenyl, wherein the substituted phenyl is substituted by one or more of the following groups: $C_1$-$C_6$ straight-chain or branched-chain alkyl, halogen, $C_1$-$C_6$ haloalkyl, amino, mercapto, cyano, nitro, hydroxyl, trifluoromethyl, and trifluoromethoxy;
n is 0, 2, 3, or 4;
$R_1$ is a hydro, or $C_1$-$C_6$ alkyl, $C_1$-$C_8$ alkoxyl, mercapto, cyano, nitro, hydroxyl, trifluoromethyl, trifluoromethoxy, phenoxy, unsubstituted $C_3$-$C_6$ heterocycloalkyl or substituted $C_3$-$C_6$ heterocycloalkyl, wherein the substituted $C_3$-$C_6$ heterocycloalkyl is substituted by one or more of the following groups:
$C_1$-$C_8$ alkyl, halogen, $C_3$-$C_6$ cycloalkyl, $(C_3$-$C_6)$cycloalkyl$(C_1$-$C_6)$alkyl, $C_1$-$C_6$ haloalkyl, amino, mercapto, cyano, nitro, hydroxyl, trifluoromethyl, trifluoromethoxy; unsubstituted or substituted $C_6$-$C_{12}$ heteroaryl containing one or two oxygen or nitrogen, unsubstituted or substituted $C_3$-$C_6$ heterocycloalkyl containing one or two oxygen or nitrogen, unsubstituted or substituted $(C_6$-$C_{12})$heterocycloalkyl$(C_1$-$C_6)$ alkyl containing one or two oxygen or nitrogen, unsubstituted or substituted phenyl, unsubstituted or substituted $(C_5$-$C_{12})$aryl$(C_1$-$C_6)$alkyl unsubstituted or substituted phenoxy, and unsubstituted or substituted carbobenzoxy, wherein the substituted groups are independently substituted by one or more of the following groups:
halogen, oxo, $C_1$-$C_6$ alkyl, $C_1$-$C_8$ alkoxyl, $C_1$-$C_6$ haloalkyl, amino, mercapto, cyano, nitro, hydroxyl, trifluoromethyl, trifluoromethoxy; and unsubstituted or substituted phenyl or phenoxy, wherein the substituted phenyl or phenoxy is independently substituted by one or more substituents selected from:
halogen, $C_1$-$C_6$ haloalkyl, amino, mercapto, cyano, nitro, hydroxyl, trifluoromethyl, and trifluoromethoxy;
$R_2$ is H, phenyl, $C_1$-$C_6$ alkyl, $C_1$-$C_8$ alkoxyl, amino, mercapto, cyano, nitro, hydroxyl, trifluoromethyl, trifluoromethoxy, or unsubstituted or substituted amino, wherein the substituted amino group is substituted by one or more of the following groups:
$C_1$-$C_6$ alkyl, $C_3$-$C_7$ carbocyclyl, phenyl, benzyl, aralkyl, sulfanilamino, pyridyl, $C_1$-$C_4$ acyl; unsubstituted or substituted $C_3$-$C_6$ heterocycloalkyl containing one or two oxygen or nitrogen, and unsubstituted or substituted phenoxy, wherein the substituted groups are independently substituted by one or more of the following groups:
halogen, $C_1$-$C_6$ haloalkyl, amino, mercapto, cyano, nitro, hydroxyl, trifluoromethyl, trifluoromethoxy, and benzyl;
$R_3$ is H, $C_1$-$C_8$ alkoxyl, halogen, mercapto, cyano, nitro, hydroxyl, trifluoromethyl, trifluoromethoxy, $C_1$-$C_6$ straight-chain or branched-chain alkyl, phenyl, aralkyl, thioureido, or unsubstituted or substituted amino, wherein the substituted amino group is substituted by one or more of the following groups: $C_1$-$C_6$ straight-chain or branched-chain alkyl, $C_3$-$C_6$ heterocycloalkyl, phenyl, aralkyl, sulfanilamino, pyridyl, and $C_1$-$C_4$ acyl;
$R_4$ is H, $C_1$-$C_6$ straight-chain or branched-chain alkyl, $C_1$-$C_8$ alkoxyl, mercapto, hydroxyl, trifluoromethyl, trifluoromethoxy, or unsubstituted or substituted phenoxy, wherein the substituted phenoxy is substituted by one or more of the following groups: halogen, $C_1$-$C_6$ haloalkyl, amino, mercapto, hydroxyl, trifluoromethyl, and trifluoromethoxy;
$R_5$ is H, $C_1$-$C_6$ straight-chain or branched-chain alkyl, or unsubstituted or substituted phenyl, wherein the substituted phenyl group is substituted by one or more of the following groups:
halogen, $C_1$-$C_6$ haloalkyl, $C_1$-$C_6$ straight-chain or branched-chain alkyl, $C_1$-$C_8$ alkoxyl, amino, mercapto, cyano, hydroxyl, trifluoromethyl, trifluoromethoxy, and unsubstituted or substituted phenyl, wherein the substituted phenyl group is substituted by one or more of the following groups:
halogen, $C_1$-$C_4$ haloalkyl, amino, mercapto, hydroxyl, trifluoromethyl, and trifluoromethoxy;
$R_6$ is H, $C_1$-$C_6$ straight-chain or branched-chain alkyl.

17. The method of claim 16, wherein said polycystic kidney disease is selected from autosomal recessive polycystic kidney disease or autosomal dominant pattern polycystic kidney disease.

18. The compound of claim 1, wherein the unsubstituted or substituted $(C_5$-$C_{12})$aryl$(C_1$-$C_6)$alkyl is benzyl, phenethyl, or naphthalen-1-ylmethyl.

19. The compound or pharmaceutically acceptable salts thereof of claim 3, wherein the unsubstituted or substituted $(C_5$-$C_{12})$aryl$(C_1$-$C_6)$alkyl is benzyl, phenethyl, or naphthalen-1-ylmethyl.

20. The process of claim 6, wherein the unsubstituted or substituted $(C_5$-$C_{12})$aryl$(C_1$-$C_6)$alkyl is benzyl, phenethyl, or naphthalen-1-ylmethyl.

21. The process of claim 7, wherein the unsubstituted or substituted $(C_5$-$C_{12})$aryl$(C_1$-$C_6)$alkyl is benzyl, phenethyl, or naphthalen-1-ylmethyl.

22. The pharmaceutical composition of claim 10, wherein the unsubstituted or substituted $(C_5$-$C_{12})$aryl$(C_1$-$C_6)$alkyl is benzyl, phenethyl, or naphthalen-1-ylmethyl.

23. The method of claim 16, wherein the unsubstituted or substituted $(C_5$-$C_{12})$aryl$(C_1$-$C_6)$alkyl is benzyl, phenethyl, or naphthalen-1-ylmethyl.

24. The pharmaceutical composition of claim 15 further comprising one or more other medicine in the treatment and prevention of polycystic kidney disease selected from an ACE inhibitor and a PPAR-γ agonist.

25. The pharmaceutical composition of claim 15 further comprising one or more other medicine in the treatment and prevention of polycystic kidney disease selected from Enalapril, Benazepril, and Rosiglitazone.

* * * * *